US005670335A

United States Patent [19]
Jan et al.

[11] Patent Number: 5,670,335
[45] Date of Patent: *Sep. 23, 1997

[54] MAMMALIAN INWARD RECTIFIER POTASSSIUM CHANNEL CDNAS, HOST CELLS EXPRESSING THEM, AND SCREENING ASSAYS USING SUCH CELLS

[75] Inventors: Lily Y. Jan; Yuh Nung Jan, both of San Francisco, Calif.; Yoshihiro Kubo, Tokyo, Japan; Eithan Reuveny; Paul A. Slesinger, both of San Francisco, Calif.

[73] Assignee: The Regents of the University of California, Oakland, Calif.

[*] Notice: The term of this patent shall not extend beyond the expiration date of Pat. No. 5,492,825.

[21] Appl. No.: 461,690

[22] Filed: Jun. 5, 1995

Related U.S. Application Data

[63] Continuation of Ser. No. 103,445, Aug. 6, 1993, Pat. No. 5,492,825.
[51] Int. Cl.$^6$ .................... C12N 15/12; C07K 14/705
[52] U.S. Cl. .................. 435/29; 536/23.5; 435/320.1; 435/240.2; 435/252.3; 435/254.11; 435/69.1; 435/7.21; 435/4; 530/350
[58] Field of Search .................. 536/23.5; 435/320.1, 435/240.1, 240.2, 252.3, 254.11, 69.1, 7.21, 29, 4; 530/350

[56] References Cited

U.S. PATENT DOCUMENTS 5,492,825  2/1996  Jan et al. .................... 435/240.2

OTHER PUBLICATIONS

Breitwieser, G. E., et al., "Uncoupling of cardiac muscarinic and β–adrenergic receptors from ion channels by a guanine nucleotide analogue", *Nature* 317:538–540 (1985).
Logothetis, D. E., et al., "The βγ subunits of GTP–binding proteins activate the muscarinic K$^+$ channel in heart", *Nature* 325(6102):321–326 (1987).
Yatani, A., et al., "The G protein–gated atrial K$^+$ channel is stimulated by three distinct G$_i$α–subunits", *Nature* 336:680–682 (1988).
Brown, A. M., et al., "Ionic Channels and Their Regulation by G Protein Subunits", *Annu. Rev. Physiol.* 52:197–213 (1990).
Kurachi, Y., et al., "G Protein Activation of Cardiac Muscarinic K$^+$ Channels", *Progress in Neurobiology* 39:229–246 (1992).
Nelson, M. T., et al., "Arterial dilations in response to calcitonin gene–related peptide involve activation of K$^+$ channels", *Nature* 344:770–773 (1990).
Rorsman, P., et al., "Activation by adrenaline of a low–conductance G protein–dependent K$^+$ channel in mouse pancreatic B cells", *Nature* 349:77–79 (1991).
Stanfield, P. R., et al., "Substance P raises neuronal membrane excitability by reducing inward rectification", *Nature* 315:498–501 (1985).

Williams, J. T., et al., "Voltage– and Ligand–Activated Inwardly Rectifying Currents in Dorsal Raphe Neurons in vitro", *The Journal of Neuroscience* 8(9):3499–3506 (1988).
Wang, W., et al., "Renal Potassium Channels and Their Regulation", *Annu Rev. Physiol.* 54:81–96 (1992).
Papazian, D. M., et al., "Cloning of Genomic and Complementary DNA from Shaker, a Putative Potassium Channel Gene from Drosophila", *Science* 237:749–753 (1987).
Tempel, B. L., et al., "Sequence of a Probable Potassium Channel Component Encoded at Shaker Locus of Drosophila", *Science* 237:770–775 (1987).
Baumann, A., et al., "Molecular organization of the maternal effect region of the Shaker complex of Drosophila: characterization of an I$_A$ channel transcript with homology to vertebrate Na$^+$ channel", *The EMBO Journal* 6(11):3419–3429 (1987).
Wei, A., et al., "K$^+$ Current Diversity Is Produced by an Extended Gene Family Conserved in Drosophila and Mouse", *Science* 248:599–603 (1990).
Tempel, B. L., et al., "Cloning of a probable potassium channel gene from mouse brain", *Nature* 332:837–839 (1988).
Baumann, A., et al., "Structure of the voltage–dependent potassium channel is highly conserved from Drosophila to vertebrate central nervous systems", *The EMBO Journal* 7(8):2457–2463 (1988).
Frech, G. C., et al., "A novel potassium channel with delayed rectifier properties isolated from rat brain by expression cloning", *Nature* 340:642–645 (1989).
Yokoyama, S., et al., "Potassium channels from NG108–15 neuroblastoma–glioma hybrid cells", *FEBS Letters* 259(1):37–42 (1989).
Christie, M. J., et al., "Expression of a Cloned Rat Brain Potassium Channel in Xenopus Oocytes", *Science* 244:221–224 (1989).
Stühmer, W., et al., "Molecular basis of functional diversity of voltage–gated potassium channels in mammalian brain", *The EMBO Journal* 8(11):3235–3244 (1989).
Swanson, R., et al., "Cloning and Expression of cDNA and Genomic Clones Encoding Three Delayed Rectifier Potassium Channels in Rat Brain", *Neuron* 4:929–939 (1990).
Luneau, C. J., et al., "Alternative splicing contributes to K$^+$ channel diversity in the mammalian central nervous system", *Proc. Natl. Acad. Sci. USA* 88:3932–3936 (1991).

(List continued on next page.)

*Primary Examiner*—David L. Fitzgerald
*Attorney, Agent, or Firm*—Flehr, Hohbach, Test, Albritton and Herbert

[57] ABSTRACT

This disclosure relates to two separate and distinct inward rectifier K$^+$ channel expression products and the the genes which encode each expression product. The IRK1 gene (SEQ ID NO:1) encodes an inward rectifier K$^+$ channel and the GIRK1 gene (SEQ ID NO:3) encodes a G protein coupled muscarinic K$^+$ channel. The disclosure relates to the uses of these expression products, particularly in combination with identifying physiological processes mediated by these channels, such as regulation of heartbeat and insulin release and materials modulating or blocking same.

16 Claims, 29 Drawing Sheets

OTHER PUBLICATIONS

Jan, L. Y., et al., "Tracing the Roots of Ion Channels", *Cell* 69:715–718 (1992).

Jan, L. Y., et al., "A superfamily of ion channels", *Nature* 345:672 (1990).

Takumi, T., et al., "Cloning of a Membrane Protein That Induces a Slow Voltage–Gated Potassium Current", *Science* 242:1042–1045 (1988).

Ho, K., et al., "Cloning and expression of an inwardly rectifying ATP–regulated potassium channel", *Nature* 362:31–38 (1993).

Katz, B., "Les Constantes Électriques De La Membrane Du Muscle", *Archives Des Sciences Physiologiques* III(2):285–300 (1949).

Standen, N. B., et al., "A Potential– and Time–Dependent Blockade of Inward Rectification in Frog Skeletal Muscle Fibres by Barium and Strontium Ions", *J. Physiol.* 280:169–191 (1978).

Sakmann, B., et al., "Conductance Properties of Single Inwardly Rectifying Potassium Channels in Ventricular Cells from Guinea–Pig Heart", *J. Physiol.* 347:641–657 (1984).

Hagiwara, S., et al., "Potassium Current and the Effect of Cesium on this Current during Anomalous Rectification of the Egg Cell Membrane of a Starfish", *The Journal of General Physiology* 67:621–638 (1976).

Okamoto, H., et al., "Membrane Currents of the Tunicate Egg under the Voltage–Clamp Condition", *J. Physiol.* 254:607–638 (1976).

Mayer, M. L., et al., "A Voltage–Clamp Analysis of Inward (Anomalous) Rectification in Mouse Spinal Sensory Ganglion Neurones", *J. Physiol.* 340:19–45 (1983).

Mihara, S., et al., "Somatostatin Increases an Inwardly Rectifying Potassium Conductance in Guinea–Pig Submucous Plexus Neurones", *J. Physiol.* 390:335–355 (1987).

Inoue, M., et al., "Somatostatin Induces an Inward Rectification in Rat Locus Coeruleus Neurones Through a Pertussis Toxin–Sensitive Mechanism", *Journal of Physiology* 407:177–198 (1988).

Barres, B. A., "Glial ion channels", *Neurobiology* 1:354–359 (1991).

McKinney, L. C., et al., "Inwardly Rectifying Whole–Cell and Single–Channel K Currents in the Murine Macrophage Cell Line J774.1", *J. Membrane Biol.* 103 41–53 (1988).

Lewis, D. L., et al., "Expression of an inwardly rectifying $K^+$ channel rat basophilic leukemia cell mRNA in *Xenopus* oocytes", *FEBS Letters* 290(1.2):17–21 (1991).

Silver, M. R., et al., "Intrinsic Gating of Inward Rectifier in Bovine Pulmonary Artery Endothelial Cells in the Presence or Absence of Internal $Mg^{2+}$", *Gen. Physiol.* 96:109–133 (1990).

Hagiwara, S., et al., "Electrical Properties of Egg Cell Membranes", *Ann. Rev. Biophys. Bioeng.* 8:385–416 (1979).

Noma, A., et al., "Acetylcholine–Induced Potassium Current Fluctuations in the Rabbit Sino–Atrial Node", *Pflügers Arch.* 381:255–262 (1979).

Matsuda, H., et al., "Ohmic conductance through the inwardly rectifying K channel and blocking by internal $Mg^{2+}$", *Nature* 325:157–159 (1987).

Vandenberg, C. A., "Inward rectification of a potassium channel in cardiac ventricular cells depends on internal magnesium ions", *Proc. Natl. Acad. Sci. USA* 84:2560–2564 (1987).

Matsuda, H., "Open–State Substructure of Inwardly Rectifying Potassium Channels Revealed by Magnesium Block in Guinea–Pig Heart Cells", *Journal of Physiology* 397:237–258 (1988).

Hagiwara, S., et al., "Anomalous Permeabilities of the Egg Cell Membrane of a Starfish in $K^+$–$Tl^+$ Mixtures", *The Journal of General Physiology* 70:269–281 (1977).

Ohmori, H., "Dual Effects of K Ions upon the Inactivation of the Anomalous Rectifier of the Tunicate Egg Cell Membrane", *J. Membrane Biol.* 53:143–156 (1980).

Trautwein, W., et al., "Zum Mechanismus der Membranwirkung des Acetylcholin an der Herzmuskelfaser", *Pflügers Archiv. Bd.* 266:324–334 (1958).

Sakmann, B., et al., "Acetylcholine activation of single muscarinic $K^+$ channels in isolated pacemaker cells of the mammalian heart", *Nature* 303:250–253 (1983).

Soejima, M., et al., "Mode of regulation of the ACh–sensitive K–channel by the muscarinic receptor in rabbit atrial cells", *Pflüger Arch.* 400:424–431 (1984).

Yatani, A., et al., "Direct Activation of Mammalian Atrial Muscarinic Potassium Channels by GTP Regulatory Protein $G_k$", *Science* 235:207–211 (1987).

Kubo, Y., et al., "Primary structure and functional expression of a mouse inward rectifier potassium channel," *Nature* 362:127–133 (March 1993).

Dascal, N., et al., "Expression of an atrial G–protein–activated potassium channel in *Xenopus oocytes*," *Proc. Natl. Acad. Sci. USA* 90:6596–6600 (Jul. 1993).

Dascal, N., et al., "Atrial G–protein–activated $K^+$ channel: Expression cloning and molecular properties," *Proc. Natl. Acad. Sci. USA* 90:10235–10239 (Nov. 1993).

Aldrich, R., "Potassium channels. Advent of a new family," *Nature* 362:107–108 (Mar. 1993).

Kubo, Y., et al., "Primary structure and functional expression of a rat G–protein–coupled muscarinic potassium channel," *Nature* 364:802–803 (Aug. 1993).

Masu, Y., et al., "cDNA cloning of bovine substance–K receptor through oocyte expression system," *Nature* 329:836–838 (Oct. 1987).

FIG. 4a(1)

```
                                                                                                                                  -266
5'...TTGCTTCGGCTCATTCTCTTTCACAAAACCACTGGATC TTACATGCTTCTGTAATCCCCACTTCCACTCCATGTCCCC
ATGATCCTGTACCAGCAACAGGACAAGGTTCTCTGGATGTGTCAGCTGAGTTACTAAGGTAACTTTGCTGGTCAAAAGAACCCCAAGGTTCTCGGAAGC ATCCATCTCCTCATTAATAATATATAT   -133
TAATTATATATATATAATTTTTTGGTGTGTCTTCACCGAACATTCAAAACTGTTTTCTTCTAAGGGTTTTGCAAAACTCAGAAACACTGGCGTCCCCAGCGGAAGC A                      -1
                                                                                                                                    30
Met Gly Ser Val Arg Thr Asn Arg Tyr Ser Ile Val Ser Ser Glu Glu Asp Gly Met Lys Leu Ala Thr Met Ala Val Ala Asn Gly Phe
ATG GGC AGT GTG AGA ACC AAC CGC TAC AGC ATC GTC TCT TCG GAG GAA GAT GGC ATG AAG CTG GCC ACT ATG GCA GTT GCC AAT GGC TTT             90
                20                                           40                                            60
Gly Asn Gly Lys Ser Lys Val His Thr Arg Gln Cys Arg Ser Arg Phe Val Lys Lys Asp Gly His Cys Asn Val Gln Phe Ile Asn
GGG AAT GGC AAG AGT AAA GTC CAT ACC CGA CAA CAG TGC AGG AGC CGC TTT GTG AAG AAA GAT CAT TGC AAT GTT CAG TTT ATC AAC                180
                                              70                                          90
Val Gly Glu Lys Gly Gln Arg Tyr Leu Ala Asp Ile Phe Thr Thr Cys Val Asp Ile Arg Trp Arg Trp Met Leu Val Ile Phe Cys Leu
GTG GGT GAG AAG GGA CAG AGG TAC CTG GCA GAC ATC TTT ACT ACC TGT GTC GAC ATC CGC TGG AGG TGG ATG CTG GTT ATC TTC TGT CTT            270
                                            100                                          120
Ala Phe Leu Ser Trp Leu Phe Phe Gly Cys Val Phe Trp Leu Ile Ala Leu Leu His Gly Asp Leu Asp Thr Ser Lys Val Ser Lys
GCC TTC CTC TCC TGG CTC CTG TTT GGC TGT GTG TTT TGG TTG ATA GCC CTG CTC CAT GGG GAT CTA GAT ACT TCT AAA GTG AGC AAA                 360
                    M1                              130                                    150
                                                                                                                H5
Ala Cys Val Ser Glu Val Asn Ser Phe Thr Ala Ala Phe Leu Phe Thr Ile Glu Thr Gln Thr Thr Ile Gly Tyr Gly Phe Arg Cys Val
GCA TGC GTG TCG GAG GTC AAC AGC TTC ACG GCT GCC TTC CTC TTC ACC ATC GAG ACC CAG ACA ACC ATT GGC TAT GGT TTC AGG TGT GTG             450
```

FIG. 4a(2)

```
                                                              M2          170                         180
       160
Thr Asp Glu Cys Pro Ile Ala Val Phe Met Val Val Phe Gln Ser Ile Val Gly Cys Ile Ile Asp Ala Phe Ile Ile Gly Ala Val Met
ACA GAC GAG TGC CCA ATT GCT GTC TTC ATG GTG GTA TTC CAG TCA ATT GTA GGC TGC ATC ATT GAC GCC TTC ATT GGT GCA GTC ATG  540
                 190                         200                         210
Ala Lys Met Ala Lys Pro Lys Lys Asn Glu Thr Leu Val Phe Ser His Asn Ala Val Ile Ala Met Arg Asp Gly Lys Leu Cys Leu
GCG AAG ATG GCA AAG CCA AAG AAG AAT GAG ACT CTT GTC TTC AGT CAC AAT GCT GTG ATT GCC ATG AGG GAT GGC AAA CTC TGC TTG  630
                 220                         230                         240
Met Trp Arg Val Gly Asn Leu Arg Lys Ser His Leu Val Glu Ala His Val Arg Ala Gln Leu Leu Lys Ser Arg Ile Thr Ser Glu Gly
ATG TGG AGA GTG GGT AAC CTT CGA AAG AGC CAC CTT GTG GAA GCT CAT GTC CGG GCA CAG CTT CTC AAA TCT AGG ATC ACT TCA GAA GGG  720
                 250                         260                         270
Glu Tyr Ile Pro Leu Asp Gln Ile Asp Ile Asn Val Gly Phe Asp Ser Gly Phe Asp Arg Ile Phe Leu Val Ser Pro Ile Thr Ile Val
GAG TAT ATC CCT TTG GAC CAG ATA GAC ATC AAT GTT GGT TTT GAT AGT GGA ATT GAC CGC ATA TTT CTA GTG TCC CCC ATC ACT ATC GTT  810
                 280                         290                         300
His Glu Ile Asp Glu Asp Ser Pro Leu Tyr Asp Leu Ser Lys Gln Asp Ile Asp Asn Ala Asp Phe Glu Ile Val Val Ile Leu Glu Gly
CAC GAA ATA GAT GAA GAC AGC CCT TTA TAT GAC TTG AGT AAG CAG GAC ATT GAC AAT GCA GAC TTT GAA ATT GTC GTC ATC CTG GAA GGC  900
                 310                         320                         330
Met Val Glu Ala Thr Ala Met Thr Thr Gln Cys Arg Ser Ser Tyr Leu Ala Asn Glu Ile Leu Trp Gly His Arg Tyr Glu Pro Val Leu
ATG GTG GAG GCG ACT GCC ATG ACA ACT CAA TGC CGG AGT TCG TAT CTG GCC AAT GAA ATT CTC TGG GGT CAC CGC TAT GAG CCA GTG CTC  990
```

Figure 4A:
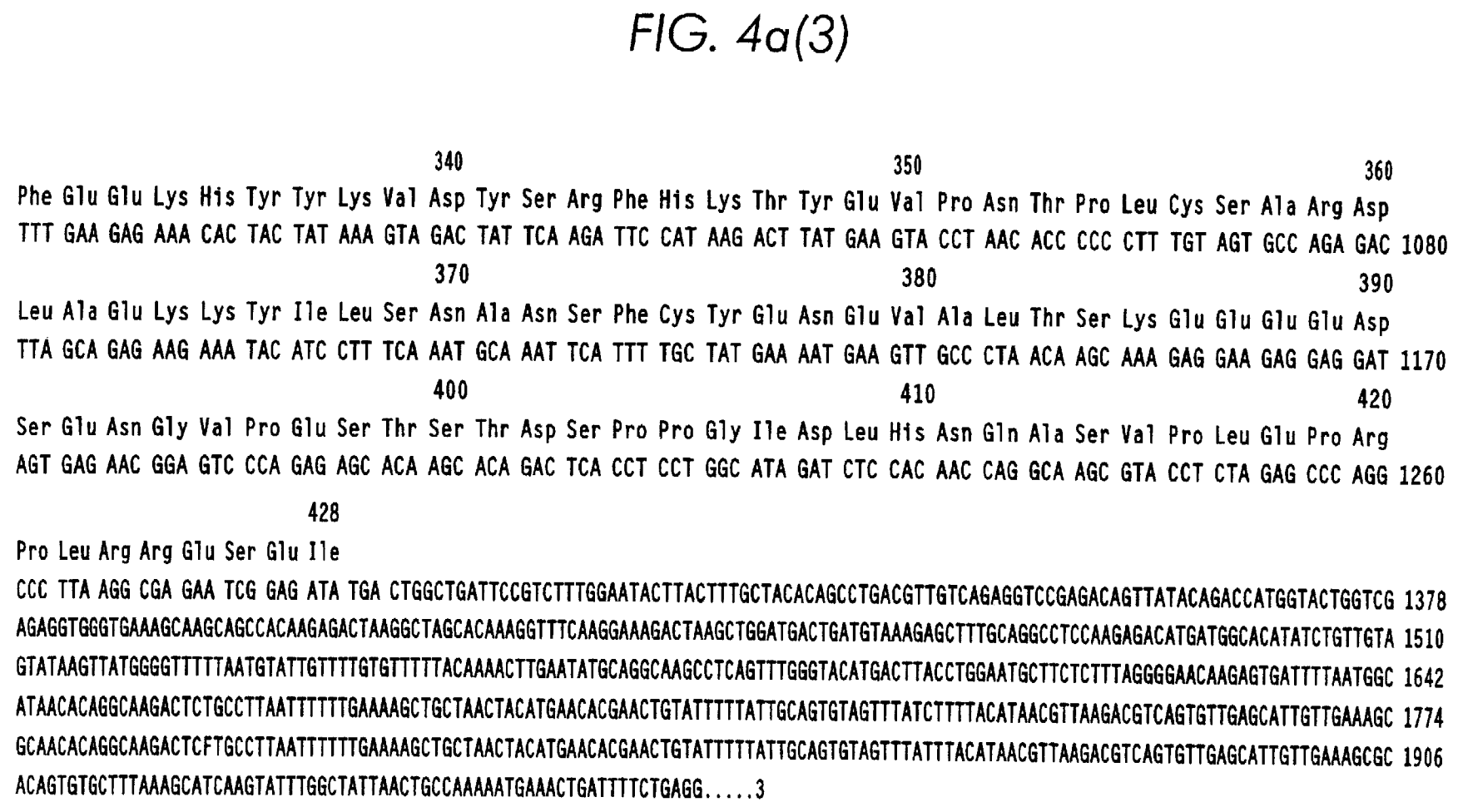

FIG. 4a(3)

```
                                        350                                        360
     Phe Glu Lys His Tyr Tyr Lys Val Asp Tyr Ser Arg Phe His Lys Thr Tyr Glu Val Pro Asn Thr Pro Leu Cys Ser Ala Arg Asp
     TTT GAA GAG AAA CAC TAC TAT AAA GTA GAC TAT TCA AGA TTC CAT AAG ACT TAT GAA GTA CCT AAC ACC CCC CTT TGT AGT GCC AGA GAC 1080
                          370                                        380                                        390
     Leu Ala Glu Lys Lys Tyr Ile Leu Ser Asn Ala Asn Ser Phe Cys Tyr Glu Asn Val Ala Leu Thr Ser Lys Glu Glu Glu Asp
     TTA GCA GAG AAG AAA TAC ATC CTT TCA AAT GCA AAT TCA TTT TGC TAT GAA AAT GTT GCC CTA ACA AGC AAA GAG GAA GAG GAT 1170
                                        400                                        410                                        420
     Ser Glu Asn Gly Val Pro Glu Ser Thr Asp Ser Pro Pro Gly Ile Asp Leu His Asn Gln Ala Ser Val Pro Leu Glu Pro Arg
     AGT GAG AAC GGA GTC CCA GAG AGC ACA GAC TCA CCT CCT GGC ATA GAT CTC CAC AAC CAG GCA AGC GTA CCT CTA GAG CCC AGG 1260
             428
     Pro Leu Arg Arg Glu Ser Glu Ile
     CCC TTA AGG CGA GAA TCG GAG ATA TGA CTGGCTGATTCCGTCTCTTTGGAATACTTACTTTGCTACACAGCCTGACGTTGTCAGAGGTCCGAGACAGTATACAGACCATGGTACTGGTCG 1378
     AGAGGTGGGTGAAAGCAAGCAGCCACAGAGACTAAGGCTAGTGTTTCAAGGAAAGACTAAGCTGGATGACTGAAAGACTTGCAGGCCTCCAAGAGACATGATGACTTAGGGAACAAGAGTGATTTAATGGC 1510
     GTATAAGTTATGGGGTTTTAATGTATTGTCCTTAATTGTGTTTGTACAAAACTTGAATATATGCAGGCAAGACTTACCTGGTACATAGTTTATTGCAGTAGTTATCTTTTACATAACGTTAAGACGTCAGT 1642
     ATAACACAGGCAAGACTCTGCCTTAATTTTTGAAAAAGCTGCTAACTACACATGAACACAGAACTGTATTTTATCTTTTTGAAAAAGTCTAAGACGTTAAGACGTTGAGGCATTGTTGAAAAGC 1774
     GCAACACAGGCAAGACTCTGCCTTAATTTTTGAAAAAGCTGCTAACATGAACACAGAACTGTAGTTTATTGCAGTGTAGTTTATTACATAACGTTAAGACGTTAAGACGTCAGTGTTGAGCATTGTTGAAAGCGC 1906
     ACAGTGTGCTTAAAGCATCAAGTATTTGGCTATTAACTGCCAAAAATGAAACTGATTTTCTGAGG....3
```

FIG. 4b

```
IRK1   MGSVRTNRYSIVSSEEDGMKLATMAVANGFGNGKSKVH----------- 38
       ||.                                      .|
ROMK1  MGA---------------------------SERSVFRVLIRALTERMFK 22

IRK1   ------------TRQQCRSRFVKKDGRCNVQFINVGEKGQ-RYLADIFT 75
                   .||  |.| | |-.|||.  | ||       .  ||.|
ROMK1  HLRRWFITHIFGRSRQ--RARLVSKEGRCNIEFGNVDAQSRFIFFVDIWT 70

M1
IRK1   TCVDIRWRWMLV│IFCLAFVLSWLFFGCVFWLIAL│LHGDL-------DTSK 117
       | .|..||. .  .|  ||. ||  ||  .....|  .  ||              .
ROMK1  TVLDLKWRYKMT│VFITAFLGSWFLFGLLWYVVAY│VHKDLPEFYPPDNRT- 119

H5                       M2
IRK1   VSKACVSEVNSFTA│AFLFSIETQTTIGYGFR│CVTDECPI│AVFMVVFQSIV 167
       ||  .|  |.│|||||.||| |||||||| ||. |  │|.|...|||│.
ROMK1  ---PCVENINGMTS│AFLFSLETQVTIGYGFR│FVTEQCAT│AIFLLIFQSIL 166

IRK1   │GCIIDAFIIGA│VMAKMAKPKKRNETLVFSHNAVIAMRDGKLCLMWRVGNL 217
        | ||  .|  ||  ..||...||||  |. ||  ||||. |  |||||. || ||
ROMK1  │GVIINSFMCGA│ILAKISRPKKRAKTITFSKNAVISKRGGKLCLLIRVANL 216

IRK1   RKSHLVEAHVRAQLLKSRITSEGEYIPLDQIDINVGFDSGIDRIFLVSPI 267
       ||| |. .|.   |||.  ||  ||||  | |||   ||    |.|  . |  .||.
ROMK1  RKSLLIGSHIYGKLLKTTITPEGETIILDQTNINFVVDAGNENLFFISPL 266

IRK1   TIVHEIDEDSPLYDLSKQDIDNADFEIVVILEGMVEATAMTTQCRSSYLA 317
       || |  ||       |  .. . . |||.||  |.|    ||.|. | | |.||.
ROMK1  TIYHIIDHNSPFFHMAAETLSQQDFELVVFLDGTVESTSATCQVRTSYVP 316

IRK1   NEILWGHRYEPVLF---EEKHYYKVDYSRFHKTYEV------------- 350
       |.|||  |. |..      ||  |.||.   |  ||   ||
ROMK1  EEVLWGYRFVPIVSKTKEGK--YRVDFHNFGKTVEVETPHCAMCLYNEKD 364

IRK1   ----------PNTPLCSARDLAEKKYILSNANSFCYENEVALTSKEEEE 389
                 ||                           |.  .|  .
ROMK1  ARARMKRGYDNPN---------------------------FVLSEVDETD 387

IRK1   DSENGVPESTSTDSPPGIDLHNQASVPLEPRPLRRESEI 428
       |.
ROMK1  DTQM 391
```

FIG. 4c

|      | H5 |   |   |   |   |   |   |   |   |   |   | H5 |
|------|----|---|---|---|---|---|---|---|---|---|---|----|
| IRK1 | A | L | F | S | I | E | T | Q | T | T | I | G | Y | G | F | R |
| Kv1.1 | A | F | W | W | A | V | V | S | M | T | T | V | G | Y | G | D | M |
| Kv2.1 | S | F | W | W | A | T | I | T | M | T | T | V | G | Y | G | D | I |
| Kv3.1 | G | F | W | W | A | V | V | T | M | T | T | L | G | Y | G | D | M |
| kv4.1 | A | V | Y | W | T | I | V | T | M | T | T | L | G | Y | G | D | M |
| *S10* | C | Y | F | L | I | V | T | M | S | T | V | G | Y | G | D | V |
| KAT1 | A | L | Y | W | S | I | T | T | L | T | T | T | G | Y | G | D | F |

FIG. 4d

|      | M1 |   |   |   |   |   |   |   |   |   |   |   | S5/H4 |
|------|----|---|---|---|---|---|---|---|---|---|---|---|---|
| IRK1 | I | F | C | L | S | W | L | F | F | G | C | V | F | W | L | I | A | L |
| Kv1.1 | L | G | L | L | I | F | F | L | F | I | G | V | I | L | F | S | S | A | V | Y | F | A |
| Kv2.1 | L | G | L | L | I | F | F | L | F | I | G | V | I | L | F | S | S | A | V | Y | F | A |
| Kv3.1 | F | L | L | L | I | I | F | L | A | L | G | V | L | I | F | A | T | M | I | Y | Y | A |
| Kv4.1 | L | G | F | L | L | F | S | L | T | M | A | I | I | I | F | A | T | V | M | F | Y | A |
| S70 | L | A | Q | L | V | S | I | F | I | S | V | W | L | T | A | A | G | I | I | H | L | L |
| KAT1 | C | T | K | L | I | S | V | T | L | F | A | I | H | C | A | G | C | F | N | Y | L | I |

FIG. 4e

```
            M2                                              S6/H5
IRK1   P I A V F M V V F Q S I V G C I I D A F I I G A
Kv1.1  G K I V G S L C A I A G V L T I A L P V P V I V
Kv2.1  G K I V G G L C C I A G V L T I A L P I P I I V
Kv3.1  G M L V G A L C A L A G V L T I A M P V P V I V
Kv4.1  G K I F G S I C S L S G V L V I A L P V P V I V
S1o    G R T F L V F F L L V G L A M F A S S I P E I I
KAT1   D I F F M M F N L G L T A Y L I G N M T N L V V
```

FIG. 7a(1)

```
                                                                                                                          -1
5'....CAGGGCTTGGCTCCTGCGGCCTCCGCTTCGTGTTGAATCTGGATCTCCCCTCGTATT
                             10                  20                  30
Met Ser Ala Leu Arg Arg Lys Phe Gly Asp Asp Tyr Gln Val Val Thr Thr Ser Ser Gly Ser Gly Leu Gln Pro Gly
ATG TCT GCA CTC CGA AGG AAA TTT GGG GAC GAT TAC CAG GTA GTG ACC ACT TCG TCC AGC GGT TCG CAG CCC CAG GGG CCA GGA         90
                             40                  50                  60
Gln Gly Pro Gln Gln Leu Val Pro Lys Lys Arg Gln Arg Phe Val Asp Lys Asn Gly Arg Cys Asn Val Gln His Gly Asn Leu
CAG GGG CCA CAG CAG CAG CTT GTA CCC AAG AAG AAA CGG CAG CGG TTC GTG GAC AAG AAC GGT CGG TGC AAT GTG CAG CAC GGC AAC CTG  180
                             70                  80                  90
Gly Ser Glu Thr Ser Arg Tyr Leu Ser Asp Leu Phe Thr Thr Leu Val Asp Leu Lys Trp Arg Trp Asn Leu Phe Ile Phe Ile Leu Thr
GGC AGT GAG ACC AGT CGC TAC CTT TCC GAC CTC TTC ACT ACC CTG GTG GAT CTC AAG TGG CGT TGG AAC CTC TTT ATC TTC ATC CTC ACC  270
                             H1                 100                 110                                         120
Tyr Thr Val Ala Trp Leu Phe Met Ala Ser Met Trp Trp Val Ile Ala Tyr Thr Arg Gly Asp Leu Asn Lys Ala His Val Gly Asn Tyr
TAC ACC GTG GCC TGG CTC TTC ATG GCG TCC ATG TGG TGG GTG ATC GCT TAT ACC CGG GGC GAC CTG AAC AAA GCC CAT GTC GGC AAC TAC  360
                            130                 140                 H5                                         150
Thr Pro Cys Val Ala Asn Val Tyr Asn Phe Pro Ser Ala Phe Leu Phe Phe Ile Glu Thr Glu Ala Thr Ile Gly Tyr Gly Tyr Arg Tyr
ACT CCC TGT GTG GCC AAT GTC TAT AAC TTC CCC TCT TCT GCC TTC CTT TTC TTC ATC GAG ACC GAG GCC ACC ATC GGC TAT GGC TAC CGC TAC 450
                            160                 H2                  170                                         180
Ile Thr Asp Lys Cys Pro Glu Gly Ile Ile Leu Phe Leu Phe Gln Ser Ile Leu Gly Ser Ile Val Asp Ala Phe Leu Ile Gly Cys Met
ATC ACC GAC AAG TGC CCC GAG GGC ATC ATC CTT TTC CTT TTC CAG TCC ATC CTT GGC TCC ATC GTG GAC GCT TTC CTC ATC GGC TGC ATG  540
                            190                 200                                         210
Phe Ile Lys Met Ser Gln Pro Lys Lys Arg Ala Glu Thr Leu Met Phe Ser Glu His Ala Val Ile Ser Met Arg Asp Gly Lys Leu Thr
TTC ATC AAG ATG TCC CAG CCC AAA AAG CGC GCC GAG ACC CTC ATG TTT AGC GAG CAT GCG GTT ATT TCC ATG AGG GAC GGA AAA CTC ACT  630
                            220                 230                                         240
Leu Met Phe Arg Val Gly Asn Leu Arg Asn Ser His Met Val Ser Ala Gln Ile Arg Cys Lys Leu Leu Lys Ser Arg Gln Thr Pro Glu
CTC ATG TTC CGG GTG GGC AAC CTG CGC AAC AGC CAC ATG GTC TCC GCG CAG ATC CGC TGC AAG CTG CTC AAA TCT CGG CAG ACA CCT GAG  720
```

FIG. 7a(2)

```
                              250                         260                         270
Gly Glu Phe Leu Pro Leu Asp Gln Leu Glu Leu Asp Val Gly Ala Asp Gln Leu Phe Leu Val Ser Pro Leu Thr Ile
GGT GAG TTT CTA CCC CTT GAC CAA CTT GAA CTG GAT GTA GGT GCA GAT CAA CTT TTT CTT GTG TCC CCT CTC ACC ATT   810
                                                280                         290                         300
Cys His Val Ile Asp Ala Lys Ser Pro Phe Tyr Asp Leu Ser Gln Arg Ser Met Gln Phe Glu Gln Thr Glu Val Val Ile Leu Glu
TGC CAC GTG ATT GAT GCC AAA AGC CCC TTT TAT GAC CTA TCC CAG AGC ATG CAA TTC GAG CAG ACT GAA GTG GTC ATC CTG GAA   900
                310                         320                         330
Gly Ile Val Glu Thr Thr Gly Met Thr Cys Gln Ala Arg Thr Cys Gln Ala Thr Val Leu Trp Gly His Arg Phe Phe Pro Val
GGC ATC GTG GAA ACC ACA GGG ATG ACT TGT CAA GCT CGA ACA TCA TAC ACC GAA GAT GAA GTT CTT TGG GGT CAT CGT TTT TTC CCT GTA   990
                    340                         350                         360
Ile Ser Leu Glu Gly Phe Phe Lys Val Asp Tyr Ser Gln Phe His Ala Thr Phe Glu Val Pro Thr Pro Pro Tyr Ser Val Lys Glu
ATT TCT TTA GAA GGA TTC TTT AAA GTC GAT TAC TCC CAG TTC CAT GCA ACC TTT GAA GTC CCC ACC CCT CCG TAC AGT GTG AAA GAG   1080
                        370                         380                         390
Gln Glu Met Leu Leu Met Ser Pro Leu Ile Ala Pro Ala Ile Thr Asn Ser Lys Glu Arg His Asn Ser Val Glu Cys Leu Asp
CAG GAA GAA ATG CTT CTC ATG TCT CCC CTT ATA ATA GCA CCA GCC ATA ACC AAC AGC AAA GAA AGA CAC AAT TCT GTG GAG TGC TTA GAT   1170
                            400                         410                         420
Gly Leu Asp Ile Ser Thr Lys Leu Pro Ser Leu Gly Asp Leu Gln Arg Ile Thr Gly Arg Glu Asp Phe Pro Lys Lys Leu Leu Arg Met Ser
GGA CTA GAT ATT AGC ACT AAA CTT CCA TCG AAG CTG CAG AAA ATT ACG GGG AGA GAA GAC TTT CCC AAA AAA CTC CTG AGG ATG AGT   1260
                                430                         440                         450
Ser Thr Thr Ser Glu Lys Ala Tyr Ser Leu Lys Met Leu Ser Asp Pro Met Ser Gln Ser Val Ala Asp Leu Pro Gly Asn Ser Glu Glu Lys
TCT ACA ACT TCA GAA AAA GCC TAT AGT TTG AAG ATG TTG TCC GAT CCC ATG AGC CAG TCT GTG GCC GAT CTT CCA GGC AAC TCT GAA GAA AAA   1350
                                    460                         470                         480
Leu Val Ser Lys Thr Thr Thr Lys Met Glu Asn Leu Ser Asn Pro Ala Lys Leu Pro Ala Lys Leu Pro Pro Lys Leu Gln Lys Met Ala Gly Gly
CTG GTA TCT AAA ACC AAG ATG GAA AAT CTT TCA AAC CCC GCC AAG CTT CCA CCG AAG CTT CAA AAG ATG GCT GGA GGA   1440
                                        490                         501
Pro Thr Arg Met Glu Gly Asn Leu Pro Ala Lys Leu Arg Lys Met Asn Ser Asp Arg Phe Thr
CCT ACC AGG ATG GAA GGG AAT CTT CCA GCC AAA CTA AGA AAA ATG AAC TCT GAC CGC TTC ACA TAG CAAAACACCCCATTAGGCATTATTTCATGTTTG   1540
ATTTAGTTTTAGTCCAATATTTGGCTGATAAGATAATCTCTCCCGGGAAATCTGAGAGGTCTATCCCAGTCTGGCAAATTCATCATGAAGTGTTGTTACTGTGTTGAACATGAGTT   1660
ACAAAGGGAGGACATCATAAGAAAGCTAATAGTTGGCATGTATTATCACATCAAGCATGCATGCAAATTTTGCAAATTTTGCATTTAGTTTTCTGGCATGATT....3'
```

FIG. 7b

```
GIRK1   MSALRRKFGDDYQVVTTSSSGSGLQ-------PQGPGQGPQQQLVPKKKR      43
IRK1    :GSV:---TNR:SI:SSEED:MK:ATMA---VAN:F:N:KSKVHTRQQC:      44
ROMK1   :G:SE:SV---FR:LIRALTERMFKHLRRWFITHIF:RSR:--------:      39

GIRK1   QRFVDKNGRCNVQHGNLGSETS-RYLSDLFTTLVDLKWRWNLF IFILTYT     92
IRK1    S:::K:D:H::::FI:V:EKGQ-:::A:I:::C::IR:::M:V  :C:AFV    93
ROMK1   A:L:S:E::::IEF::VDAQSRFIFFV:IW::VL:::::YKMT V::TAFL    89
                    M1                                 H5
GIRK1   VAWLFMASMWWVIAY TRGDLNKA-HVGNYTPCVANVYNFPS AFLFFIETE   141
IRK1    LS:::FGCVF:L::L LH:::DTS-K:SK--A::SE:NS:TA ::::S:::Q   140
ROMK1   GS:FLFGLL:Y:V:: VHK::PEFYPPD:R::::E:INGMT: ::::SL::Q   139
                                      M2
GIRK1   ATIGYGYR YITDKCPE GIILFLFQSILGSIVDAFLIGC MFIKMSQPKKRA  191
IRK1    T:::::F: CV::E::I AVFMVV::::V:C:I:::I::A VMA::AK::::N  190
ROMK1   V:::::F: FV:EQ:AT A:F:LI:::::V:INS:MC:A ILA:I:R:::::   189

GIRK1   ETLMFSEHAVISMRDGKLTLMFRVGNLRNSHMVSAQIRCKLLKSRQTPEG     241
IRK1    :::V::HN:::A::::::C::W:::::K::L:E:HV:AQ:::::I:S::      240
ROMK1   K:IT::KN::::K:G:::C:LI::A:::K:LLIGSHIYG::::TTI::::     239

GIRK1   EFLPLDQLELDVGFSTGADQLFLVSPLTICHVIDAKSPFYDLSQRSMQTE     291
IRK1    :YI::::IDIN:::DS:I:RI:::::I::V:E::ED::L::::KQDIDNA     290
ROMK1   :TII:::TNINFVVDA:NEN::FI:::::Y:I::HN:::FHMAAAETLSQQ    289

GIRK1   QFEVVVILEGIVETTGMTCQARTSYTEDEVLWGHRFFPVISLEE-GFFKV     340
IRK1    D::I:::::M::A:A::T:C:S::LAN:I:::::YE::LFE:K-HYY::     339
ROMK1   D::L::F:D:T::S:SA:::V::::VPE:::::Y::V:IV:KTKE:KYR:     339

GIRK1   DYSQFHATFEVPTPPYSVKEQEEMLLMSSPLIAPAITNSKERHNSVECLD     390
IRK1    :::R::K:Y:::NT:LCSARD----:AEKKYILSNANSF--------:YE     377
ROMK1   :FHN:GK:V:::-ET:HCAM---------------------------::Y     360

GIRK1   GLDDISTKLPSKLQKITGREDFPKKLLRMSSTTSEKAYSLGDLPMKLQRI     440
IRK1    --NEVA--:T:::EEEEDSENGV:E-------::STDS--PP:---ID:HNQ   412
ROMK1   NEK:ARARMK---------------------------RG:DNPNFVL-----   380

GIRK1   SSVPGNSEEKLVSKTTKMLSDPMSQSVADLPPKLQKMAGGPTRMEGNLPA     490
IRK1    A:::---------------------------:E:RR------:L:R:SEI--   428
ROMK1   :E:DETDDTQM-----------------------------------         391

GIRK1   KLRKMNSDRFT     501
IRK1
ROMK1
```

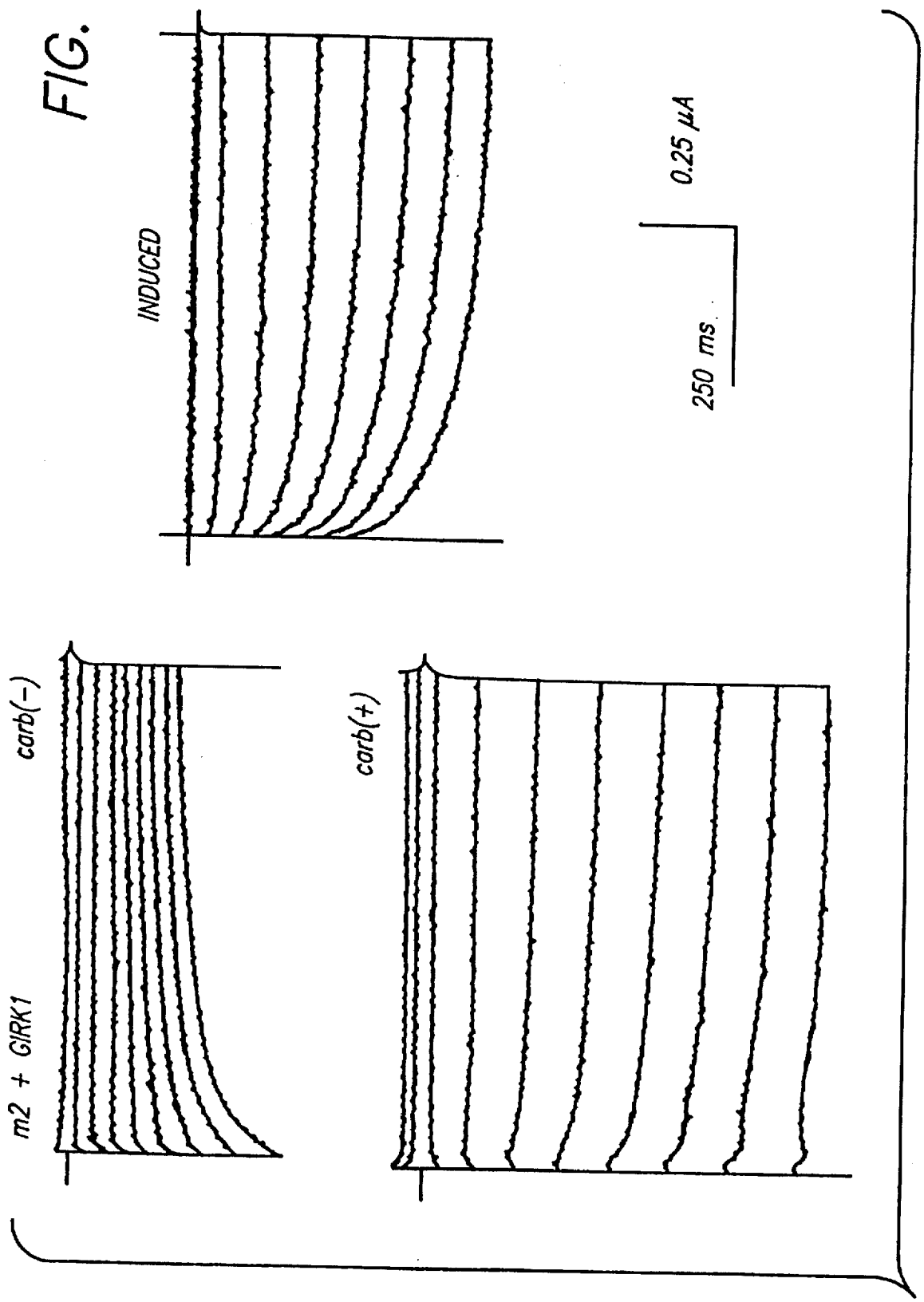

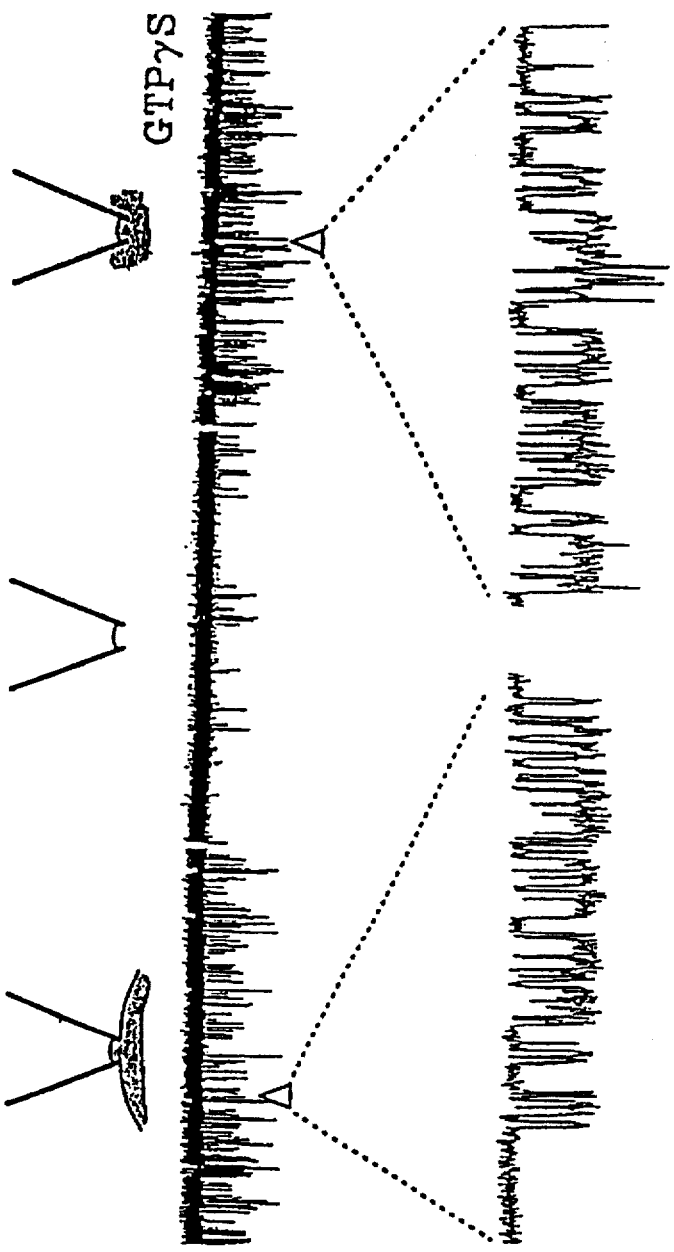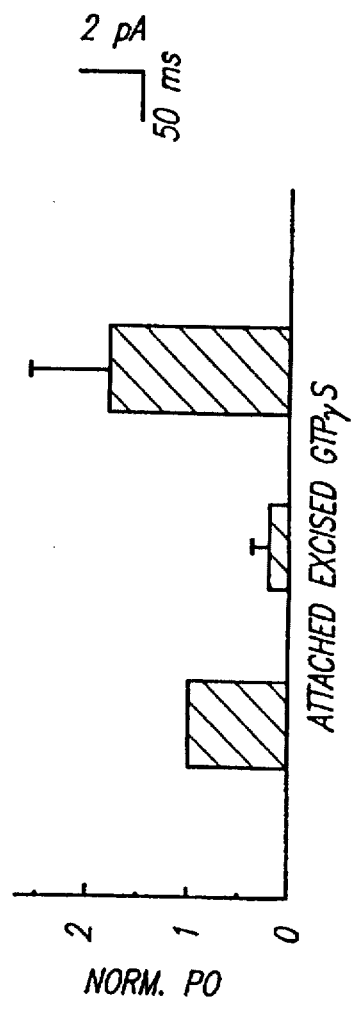
FIG. 9a
FIG. 9b

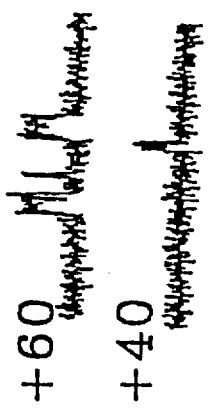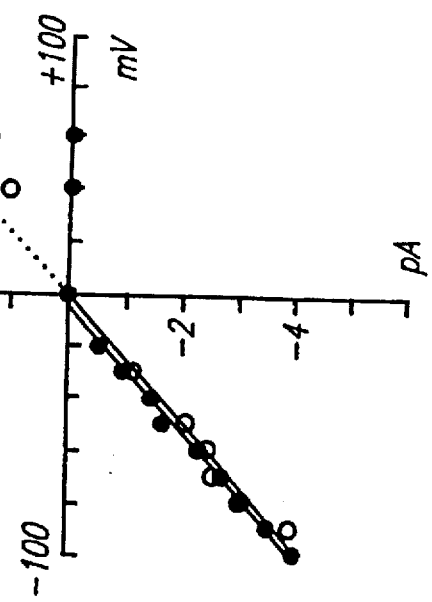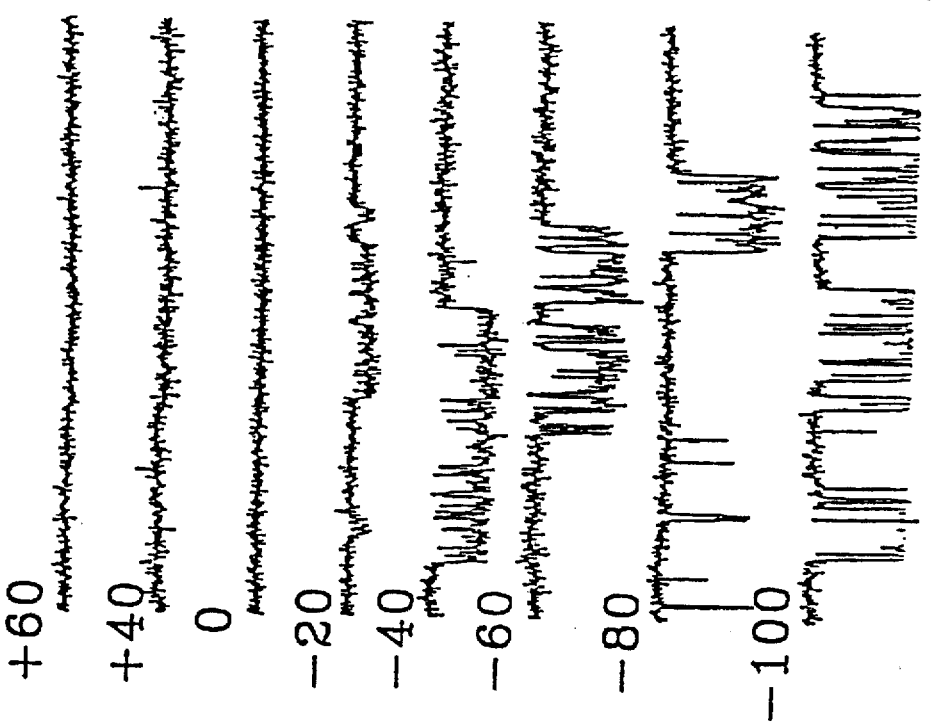

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2310 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS -continued ( B ) LOCATION: 338..1624

( i x ) FEATURE:
( A ) NAME/KEY: misc_feature
( B ) LOCATION: 596..661
( D ) OTHER INFORMATION: /note="Region encoding M1 segment."

( i x ) FEATURE:
( A ) NAME/KEY: misc_feature
( B ) LOCATION: 731..781
( D ) OTHER INFORMATION: /note="Region encoding H5 segment."

( i x ) FEATURE:
( A ) NAME/KEY: misc_feature
( B ) LOCATION: 806..871
( D ) OTHER INFORMATION: /note="Region encoding M2 segment."

( i x ) FEATURE:
( A ) NAME/KEY: misc_feature
( B ) LOCATION: 2131..2132
( D ) OTHER INFORMATION: /note="The 'N'occurring at this position represents an 'F'."

( x i ) SEQUENCE DESCRIPTION: SEQ ID NO:1:

```
TTGCTTCGGC TCATTCTCTT TCACAAAAAC CACTGGATCT TACATGCTTC TGTAATCCCC      60

ACTTCCACTC CATGTCCCCA TGATCCTGTA CCAGCAACAG GACAAGTTCT CTGGATGTCA     120

GCTGAGTTAC TAAGGTAACT TTGCTGGTCA AAAGAACCCC AAGGTTCTCG GAAGCATCCA     180

TCTCTCCTCA TTAATAAATA TATATATTAA TTATATATAT ATATATAATT TTTTTTGGTG     240

TGTCTTCACC GAACATTCAA AACTGTTTCT TCTAAGGGTT TTGCAAAAAC TCAGACTGTT     300

TTCTAAAGCA GAAACACTGG CGTCCCCAGC GGAAGCA ATG GGC AGT GTG AGA ACC     355
                                         Met Gly Ser Val Arg Thr
                                           1               5

AAC CGC TAC AGC ATC GTC TCT TCG GAG GAA GAT GGC ATG AAG CTG GCC     403
Asn Arg Tyr Ser Ile Val Ser Ser Glu Glu Asp Gly Met Lys Leu Ala
             10                  15                  20

ACT ATG GCA GTT GCC AAT GGC TTT GGG AAT GGC AAG AGT AAA GTC CAT     451
Thr Met Ala Val Ala Asn Gly Phe Gly Asn Gly Lys Ser Lys Val His
         25                  30                  35

ACC CGA CAA CAG TGC AGG AGC CGC TTT GTG AAG AAA GAT GGT CAT TGC     499
Thr Arg Gln Gln Cys Arg Ser Arg Phe Val Lys Lys Asp Gly His Cys
     40                  45                  50

AAT GTT CAG TTT ATC AAC GTG GGT GAG AAG GGA CAG AGG TAC CTG GCA     547
Asn Val Gln Phe Ile Asn Val Gly Glu Lys Gly Gln Arg Tyr Leu Ala
 55                  60                  65                  70

GAC ATC TTT ACT ACC TGT GTC GAC ATC CGC TGG AGG TGG ATG CTG GTT     595
Asp Ile Phe Thr Thr Cys Val Asp Ile Arg Trp Arg Trp Met Leu Val
                 75                  80                  85

ATC TTC TGT CTT GCC TTC GTG CTC TCC TGG CTG TTC TTT GGC TGT GTG     643
Ile Phe Cys Leu Ala Phe Val Leu Ser Trp Leu Phe Phe Gly Cys Val
             90                  95                 100

TTT TGG TTG ATA GCC CTG CTC CAT GGG GAT CTA GAT ACT TCT AAA GTG     691
Phe Trp Leu Ile Ala Leu Leu His Gly Asp Leu Asp Thr Ser Lys Val
        105                 110                 115

AGC AAA GCA TGC GTG TCG GAG GTC AAC AGC TTC ACG GCT GCC TTC CTC     739
Ser Lys Ala Cys Val Ser Glu Val Asn Ser Phe Thr Ala Ala Phe Leu
    120                 125                 130

TTC TCC ATC GAG ACC CAG ACA ACC ATT GGC TAT GGT TTC AGG TGT GTG     787
Phe Ser Ile Glu Thr Gln Thr Thr Ile Gly Tyr Gly Phe Arg Cys Val
135                 140                 145                 150

ACA GAC GAG TGC CCA ATT GCT GTC TTC ATG GTG GTA TTC CAG TCA ATT     835
Thr Asp Glu Cys Pro Ile Ala Val Phe Met Val Val Phe Gln Ser Ile
```

|     |     |
| --- | --- |
| GTA GGC TGC ATC ATT GAC GCC TTC ATC ATT GGT GCA GTC ATG GCG AAG<br>Val Gly Cys Ile Ile Asp Ala Phe Ile Ile Gly Ala Val Met Ala Lys<br>170                                              175                              180 | 883 |
| ATG GCA AAG CCA AAG AAG AGA AAT GAG ACT CTT GTC TTC AGT CAC AAT<br>Met Ala Lys Pro Lys Lys Arg Asn Glu Thr Leu Val Phe Ser His Asn<br>185                                     190                                 195 | 931 |
| GCT GTG ATT GCC ATG AGG GAT GGC AAA CTC TGC TTG ATG TGG AGA GTG<br>Ala Val Ile Ala Met Arg Asp Gly Lys Leu Cys Leu Met Trp Arg Val<br>200                                205                               210 | 979 |
| GGT AAC CTT CGA AAG AGC CAC CTT GTG GAA GCT CAT GTC CGG GCA CAG<br>Gly Asn Leu Arg Lys Ser His Leu Val Glu Ala His Val Arg Ala Gln<br>215                          220                      225                          230 | 1027 |
| CTT CTC AAA TCT AGG ATC ACT TCA GAA GGG GAG TAT ATC CCT TTG GAC<br>Leu Leu Lys Ser Arg Ile Thr Ser Glu Gly Glu Tyr Ile Pro Leu Asp<br>235                                 240                               245 | 1075 |
| CAG ATA GAC ATC AAT GTT GGT TTT GAT AGT GGA ATT GAC CGC ATA TTT<br>Gln Ile Asp Ile Asn Val Gly Phe Asp Ser Gly Ile Asp Arg Ile Phe<br>250                            255                            260 | 1123 |
| CTA GTG TCC CCC ATC ACT ATC GTT CAC GAA ATA GAT GAA GAC AGC CCT<br>Leu Val Ser Pro Ile Thr Ile Val His Glu Ile Asp Glu Asp Ser Pro<br>265                            270                          275 | 1171 |
| TTA TAT GAC TTG AGT AAG CAG GAC ATT GAC AAT GCA GAC TTT GAA ATT<br>Leu Tyr Asp Leu Ser Lys Gln Asp Ile Asp Asn Ala Asp Phe Glu Ile<br>280                           285                        290 | 1219 |
| GTT GTC ATA CTG GAA GGC ATG GTG GAG GCG ACT GCC ATG ACA ACT CAA<br>Val Val Ile Leu Glu Gly Met Val Glu Ala Thr Ala Met Thr Thr Gln<br>295                            300                        305                  310 | 1267 |
| TGC CGG AGT TCG TAT CTG GCC AAT GAA ATT CTC TGG GGT CAC CGC TAT<br>Cys Arg Ser Ser Tyr Leu Ala Asn Glu Ile Leu Trp Gly His Arg Tyr<br>               315                          320                        325 | 1315 |
| GAG CCA GTG CTC TTT GAA GAG AAA CAC TAC TAT AAA GTA GAC TAT TCA<br>Glu Pro Val Leu Phe Glu Glu Lys His Tyr Tyr Lys Val Asp Tyr Ser<br>330                                 335                            340 | 1363 |
| AGA TTC CAT AAG ACT TAT GAA GTA CCT AAC ACC CCC CTT TGT AGT GCC<br>Arg Phe His Lys Thr Tyr Glu Val Pro Asn Thr Pro Leu Cys Ser Ala<br>               345                          350                        355 | 1411 |
| AGA GAC TTA GCA GAG AAG AAA TAC ATC CTT TCA AAT GCA AAT TCA TTT<br>Arg Asp Leu Ala Glu Lys Lys Tyr Ile Leu Ser Asn Ala Asn Ser Phe<br>360                                 365                           370 | 1459 |
| TGC TAT GAA AAT GAA GTT GCC CTA ACA AGC AAA GAG GAA GAG GAG GAT<br>Cys Tyr Glu Asn Glu Val Ala Leu Thr Ser Lys Glu Glu Glu Glu Asp<br>375                                 380                        385                  390 | 1507 |
| AGT GAG AAC GGA GTC CCA GAG AGC ACA AGC ACA GAC TCA CCT CCT GGC<br>Ser Glu Asn Gly Val Pro Glu Ser Thr Ser Thr Asp Ser Pro Pro Gly<br>                                 395                        400                        405 | 1555 |
| ATA GAT CTC CAC AAC CAG GCA AGC GTA CCT CTA GAG CCC AGG CCC TTA<br>Ile Asp Leu His Asn Gln Ala Ser Val Pro Leu Glu Pro Arg Pro Leu<br>               410                          415                        420 | 1603 |
| AGG CGA GAA TCG GAG ATA TGA CTGGCTGATT CCGTCTTTGG AATACTTACT<br>Arg Arg Glu Ser Glu Ile *<br>               425 | 1654 |
| TTGCTACACA GCCTGACGTT GTCAGAGGTC CGAGACAGTT ATACAGACCA TGGTACTGGT | 1714 |
| CGAGAGGTGG GTGAAAGCAA GCAGCCACAA GAGACTAAGG CTAGCACAAA GGTTTCAAGG | 1774 |
| AAAGACTAAG CTGGATGACT GATGTAAAGA GCTTTGCAGG CCTCCAAGAG ACATGATGGC | 1834 |
| ACATATCTGT TGTAGTATAA GTTATGGGGT TTTTAATGTA TTGTTTTGTG TTTTTACAAA | 1894 |
| ACTTGAATAT GCAGGCAAGC CTCAGTTTGG GTACATGACT TACCTGGAAT GCTTCTCTTT | 1954 |

-continued

```
AGGGGAACAA GAGTGATTTT AATGGCATAA CACAGGCAAG ACTCTGCCTT AATTTTTTGA  2014
AAAGCTGCTA ACTACATGAA CACGAACTGT ATTTTATTG CAGTGTAGTT TATCTTTTAC   2074
ATAACGTTAA GACGTCAGTG TTGAGCATTG TTGAAAGCGC AACACAGGCA AGACTCNTGC  2134
CTTAATTTTT TGAAAAGCTG CTAACTACAT GAACACGAAC TGTATTTTTA TTGCAGTGTA  2194
GTTTATTTAC ATAACGTTAA GACGTCAGTG TTGAGCATTG TTGAAAGCGC ACAGTGTGCT  2254
TTAAAGCATC AAGTATTTGG CTATTAACTG CCAAAAATGA AACTGATTTT CTGAGG      2310
```

( 2 ) INFORMATION FOR SEQ ID NO:2:

( i ) SEQUENCE CHARACTERISTICS:
        ( A ) LENGTH: 428 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Ser Val Arg Thr Asn Arg Tyr Ser Ile Val Ser Ser Glu Glu
  1               5                  10                  15

Asp Gly Met Lys Leu Ala Thr Met Ala Val Ala Asn Gly Phe Gly Asn
             20                  25                  30

Gly Lys Ser Lys Val His Thr Arg Gln Gln Cys Arg Ser Arg Phe Val
         35                  40                  45

Lys Lys Asp Gly His Cys Asn Val Gln Phe Ile Asn Val Gly Glu Lys
     50                  55                  60

Gly Gln Arg Tyr Leu Ala Asp Ile Phe Thr Thr Cys Val Asp Ile Arg
 65                  70                  75                  80

Trp Arg Trp Met Leu Val Ile Phe Cys Leu Ala Phe Val Leu Ser Trp
                 85                  90                  95

Leu Phe Phe Gly Cys Val Phe Trp Leu Ile Ala Leu Leu His Gly Asp
                100                 105                 110

Leu Asp Thr Ser Lys Val Ser Lys Ala Cys Val Ser Glu Val Asn Ser
            115                 120                 125

Phe Thr Ala Ala Phe Leu Phe Ser Ile Glu Thr Gln Thr Thr Ile Gly
130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
                180                 185                 190

Leu Val Phe Ser His Asn Ala Val Ile Ala Met Arg Asp Gly Lys Leu
            195                 200                 205

Cys Leu Met Trp Arg Val Gly Asn Leu Arg Lys Ser His Leu Val Glu
210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
            260                 265                 270

Ile Asp Glu Asp Ser Pro Leu Tyr Asp Leu Ser Lys Gln Asp Ile Asp
        275                 280                 285

Asn Ala Asp Phe Glu Ile Val Val Ile Leu Glu Gly Met Val Glu Ala
290                 295                 300
```

```
Thr  Ala  Met  Thr  Thr  Gln  Cys  Arg  Ser  Ser  Tyr  Leu  Ala  Asn  Glu  Ile
305                 310                      315                      320

Leu  Trp  Gly  His  Arg  Tyr  Glu  Pro  Val  Leu  Phe  Glu  Glu  Lys  His  Tyr
                325                      330                      335

Tyr  Lys  Val  Asp  Tyr  Ser  Arg  Phe  His  Lys  Thr  Tyr  Glu  Val  Pro  Asn
               340                      345                 350

Thr  Pro  Leu  Cys  Ser  Ala  Arg  Asp  Leu  Ala  Glu  Lys  Lys  Tyr  Ile  Leu
               355                 360                      365

Ser  Asn  Ala  Asn  Ser  Phe  Cys  Tyr  Glu  Asn  Glu  Val  Ala  Leu  Thr  Ser
          370                 375                      380

Lys  Glu  Glu  Glu  Glu  Asp  Ser  Glu  Asn  Gly  Val  Pro  Glu  Ser  Thr  Ser
385                      390                      395                      400

Thr  Asp  Ser  Pro  Pro  Gly  Ile  Asp  Leu  His  Asn  Gln  Ala  Ser  Val  Pro
               405                      410                      415

Leu  Glu  Pro  Arg  Pro  Leu  Arg  Arg  Glu  Ser  Glu  Ile
               420                      425
```

( 2 ) INFORMATION FOR SEQ ID NO:3:

( i ) SEQUENCE CHARACTERISTICS:
        ( A ) LENGTH: 1827 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 59..1561

( i x ) FEATURE:
        ( A ) NAME/KEY: misc_feature
        ( B ) LOCATION: 314..379
        ( D ) OTHER INFORMATION: /note="Region encoding M1
            segment."

( i x ) FEATURE:
        ( A ) NAME/KEY: misc_feature
        ( B ) LOCATION: 455..505
        ( D ) OTHER INFORMATION: /note="Region encoding H5
            segment."

( i x ) FEATURE:
        ( A ) NAME/KEY: misc_feature
        ( B ) LOCATION: 530..595

( x i ) SEQUENCE DESCRIPTION: SEQ ID NO:3:

CAGCGCTTGG CTCCTGCGCC TCCGCTTCGT GTTTGAATCT GGATCTCCCC TCCGTATT 58

ATG TCT GCA CTC CGA AGG AAA TTT GGG GAC GAT TAC CAG GTA GTG ACC 106
Met Ser Ala Leu Arg Arg Lys Phe Gly Asp Asp Tyr Gln Val Val Thr
1 5 10 15

ACT TCG TCC AGC GGT TCG GGC TTG CAG CCC CAG GGG CCA GGA CAG GGC 154
Thr Ser Ser Ser Gly Ser Gly Leu Gln Pro Gln Gly Pro Gly Gln Gly
20 25 30

CCA CAG CAG CAG CTT GTA CCC AAG AAG AAA CGG CAG CGG TTC GTG GAC 202
Pro Gln Gln Gln Leu Val Pro Lys Lys Lys Arg Gln Arg Phe Val Asp
35 40 45

AAG AAC GGT CGG TGC AAT GTG CAG CAC GGC AAC CTG GGC AGC GAG ACC 250
Lys Asn Gly Arg Cys Asn Val Gln His Gly Asn Leu Gly Ser Glu Thr
50 55 60

AGT CGC TAC CTT TCC GAC CTC TTC ACT ACC CTG GTG GAT CTC AAG TGG 298
Ser Arg Tyr Leu Ser Asp Leu Phe Thr Thr Leu Val Asp Leu Lys Trp
65 70 75 80

```
CGT TGG AAC CTC TTT ATC TTC ATC CTC ACC TAC ACC GTG GCC TGG CTC      346
Arg Trp Asn Leu Phe Ile Phe Ile Leu Thr Tyr Thr Val Ala Trp Leu
             85                  90                      95

TTC ATG GCG TCC ATG TGG TGG GTG ATC GCT TAT ACC CGG GGC GAC CTG      394
Phe Met Ala Ser Met Trp Trp Val Ile Ala Tyr Thr Arg Gly Asp Leu
                100                 105                 110

AAC AAA GCC CAT GTC GGC AAC TAC ACT CCC TGT GTG GCC AAT GTC TAT      442
Asn Lys Ala His Val Gly Asn Tyr Thr Pro Cys Val Ala Asn Val Tyr
         115                 120                 125

AAC TTC CCC TCT GCC TTC CTT TTC TTC ATC GAG ACC GAG GCC ACC ATC      490
Asn Phe Pro Ser Ala Phe Leu Phe Phe Ile Glu Thr Glu Ala Thr Ile
     130                 135                 140

GGC TAT GGC TAC CGC TAC ATC ACC GAC AAG TGC CCC GAG GGC ATC ATC      538
Gly Tyr Gly Tyr Arg Tyr Ile Thr Asp Lys Cys Pro Glu Gly Ile Ile
145                 150                 155                 160

CTT TTC CTT TTC CAG TCC ATC CTT GGC TCC ATC GTG GAC GCT TTC CTC      586
Leu Phe Leu Phe Gln Ser Ile Leu Gly Ser Ile Val Asp Ala Phe Leu
                165                 170                 175

ATC GGC TGC ATG TTC ATC AAG ATG TCC CAG CCC AAA AAG CGC GCC GAG      634
Ile Gly Cys Met Phe Ile Lys Met Ser Gln Pro Lys Lys Arg Ala Glu
             180                 185                 190

ACC CTC ATG TTT AGC GAG CAT GCG GTT ATT TCC ATG AGG GAC GGA AAA      682
Thr Leu Met Phe Ser Glu His Ala Val Ile Ser Met Arg Asp Gly Lys
         195                 200                 205

CTC ACT CTC ATG TTC CGG GTG GGC AAC CTG CGC AAC AGC CAC ATG GTC      730
Leu Thr Leu Met Phe Arg Val Gly Asn Leu Arg Asn Ser His Met Val
     210                 215                 220

TCC GCG CAG ATC CGC TGC AAG CTG CTC AAA TCT CGG CAG ACA CCT GAG      778
Ser Ala Gln Ile Arg Cys Lys Leu Leu Lys Ser Arg Gln Thr Pro Glu
225                 230                 235                 240

GGT GAG TTT CTA CCC CTT GAC CAA CTT GAA CTG GAT GTA GGT TTT AGT      826
Gly Glu Phe Leu Pro Leu Asp Gln Leu Glu Leu Asp Val Gly Phe Ser
                245                 250                 255

ACA GGG GCA GAT CAA CTT TTT CTT GTG TCC CCT CTC ACC ATT TGC CAC      874
Thr Gly Ala Asp Gln Leu Phe Leu Val Ser Pro Leu Thr Ile Cys His
             260                 265                 270

GTG ATT GAT GCC AAA AGC CCC TTT TAT GAC CTA TCC CAG CGA AGC ATG      922
Val Ile Asp Ala Lys Ser Pro Phe Tyr Asp Leu Ser Gln Arg Ser Met
         275                 280                 285

CAA ACT GAA CAG TTC GAG GTG GTC GTC ATC CTG GAA GGC ATC GTG GAA      970
Gln Thr Glu Gln Phe Glu Val Val Val Ile Leu Glu Gly Ile Val Glu
     290                 295                 300

ACC ACA GGG ATG ACT TGT CAA GCT CGA ACA TCA TAC ACC GAA GAT GAA     1018
Thr Thr Gly Met Thr Cys Gln Ala Arg Thr Ser Tyr Thr Glu Asp Glu
305                 310                 315                 320

GTT CTT TGG GGT CAT CGT TTT TTC CCT GTA ATT TCT TTA GAA GAA GGA     1066
Val Leu Trp Gly His Arg Phe Phe Pro Val Ile Ser Leu Glu Glu Gly
                325                 330                 335

TTC TTT AAA GTC GAT TAC TCC CAG TTC CAT GCA ACC TTT GAA GTC CCC     1114
Phe Phe Lys Val Asp Tyr Ser Gln Phe His Ala Thr Phe Glu Val Pro
             340                 345                 350

ACC CCT CCG TAC AGT GTG AAA GAG CAG GAA GAA ATG CTT CTC ATG TCT     1162
Thr Pro Pro Tyr Ser Val Lys Glu Gln Glu Glu Met Leu Leu Met Ser
         355                 360                 365

TCC CCT TTA ATA GCA CCA GCC ATA ACC AAC AGC AAA GAA AGA CAC AAT     1210
Ser Pro Leu Ile Ala Pro Ala Ile Thr Asn Ser Lys Glu Arg His Asn
     370                 375                 380

TCT GTG GAG TGC TTA GAT GGA CTA GAT GAC ATT AGC ACA AAA CTT CCA     1258
Ser Val Glu Cys Leu Asp Gly Leu Asp Asp Ile Ser Thr Lys Leu Pro
385                 390                 395                 400
```

| | |
|---|---|
| TCG AAG CTG CAG AAA ATT ACG GGG AGA GAA GAC TTT CCC AAA AAA CTC<br>Ser Lys Leu Gln Lys Ile Thr Gly Arg Glu Asp Phe Pro Lys Lys Leu<br>     405                   410                   415 | 1306 |
| CTG AGG ATG AGT TCT ACA ACT TCA GAA AAA GCC TAT AGT TTG GGT GAT<br>Leu Arg Met Ser Ser Thr Thr Ser Glu Lys Ala Tyr Ser Leu Gly Asp<br>            420                   425                430 | 1354 |
| TTG CCC ATG AAA CTC CAA CGA ATA AGT TCG GTT CCT GGC AAC TCT GAA<br>Leu Pro Met Lys Leu Gln Arg Ile Ser Ser Val Pro Gly Asn Ser Glu<br>         435                   440                 445 | 1402 |
| GAA AAA CTG GTA TCT AAA ACC ACC AAG ATG TTA TCA GAT CCC ATG AGC<br>Glu Lys Leu Val Ser Lys Thr Thr Lys Met Leu Ser Asp Pro Met Ser<br>450                   455                 460 | 1450 |
| CAG TCT GTG GCC GAT TTG CCA CCG AAG CTT CAA AAG ATG GCT GGA GGA<br>Gln Ser Val Ala Asp Leu Pro Pro Lys Leu Gln Lys Met Ala Gly Gly<br>465                   470                 475               480 | 1498 |
| CCT ACC AGG ATG GAA GGG AAT CTT CCA GCC AAA CTA AGA AAA ATG AAC<br>Pro Thr Arg Met Glu Gly Asn Leu Pro Ala Lys Leu Arg Lys Met Asn<br>             485                   490                 495 | 1546 |
| TCT GAC CGC TTC ACA TAGCAAAACA CCCCATTAGG CATTATTTCA TGTTTTGATT<br>Ser Asp Arg Phe Thr<br>             500 | 1601 |
| TAGTTTTAGT CCAATATTTG GCTGATAAGA TAATCCTCCC CGGGAAATCT GAGAGGTCTA | 1661 |
| TCCCAGTCTG GCAAATTCAT CAGAGGACTC TTCATTGAAG TGTTGTTACT GTGTTGAACA | 1721 |
| TGAGTTACAA AGGGAGGACA TCATAAGAAA GCTAATAGTT GGCATGTATT ATCACATCAA | 1781 |
| GCATGCAATA ATGTGCAAAT TTTGCATTTA GTTTCTGGC ATGATT | 1827 |

( 2 ) INFORMATION FOR SEQ ID NO:4:

( i ) SEQUENCE CHARACTERISTICS:
        ( A ) LENGTH: 501 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ser  Ala  Leu  Arg  Arg  Lys  Phe  Gly  Asp  Asp  Tyr  Gln  Val  Val  Thr
 1               5                   10                  15

Thr  Ser  Ser  Ser  Gly  Ser  Gly  Leu  Gln  Pro  Gln  Gly  Pro  Gly  Gln  Gly
              20                  25                  30

Pro  Gln  Gln  Gln  Leu  Val  Pro  Lys  Lys  Lys  Arg  Gln  Arg  Phe  Val  Asp
         35                  40                  45

Lys  Asn  Gly  Arg  Cys  Asn  Val  Gln  His  Gly  Asn  Leu  Gly  Ser  Glu  Thr
     50                  55                  60

Ser  Arg  Tyr  Leu  Ser  Asp  Leu  Phe  Thr  Thr  Leu  Val  Asp  Leu  Lys  Trp
65                  70                  75                  80

Arg  Trp  Asn  Leu  Phe  Ile  Phe  Ile  Leu  Thr  Tyr  Thr  Val  Ala  Trp  Leu
                 85                  90                  95

Phe  Met  Ala  Ser  Met  Trp  Trp  Val  Ile  Ala  Tyr  Thr  Arg  Gly  Asp  Leu
             100                 105                 110

Asn  Lys  Ala  His  Val  Gly  Asn  Tyr  Thr  Pro  Cys  Val  Ala  Asn  Val  Tyr
         115                 120                 125

Asn  Phe  Pro  Ser  Ala  Phe  Leu  Phe  Phe  Ile  Glu  Thr  Glu  Ala  Thr  Ile
     130                 135                 140

Gly  Tyr  Gly  Tyr  Arg  Tyr  Ile  Thr  Asp  Lys  Cys  Pro  Glu  Gly  Ile  Ile
145                 150                 155                 160

Leu  Phe  Leu  Phe  Gln  Ser  Ile  Leu  Gly  Ser  Ile  Val  Asp  Ala  Phe  Leu
                 165                 170                 175
```

| | | | | | | | | | | | | | | |
|---|---|---|---|---|---|---|---|---|---|---|---|---|---|---|
| Ile | Gly | Cys | Met<br>180 | Phe | Ile | Lys | Met | Ser<br>185 | Gln | Pro | Lys | Lys | Arg<br>190 | Ala | Glu |
| Thr | Leu | Met<br>195 | Phe | Ser | Glu | His | Ala<br>200 | Val | Ile | Ser | Met | Arg<br>205 | Asp | Gly | Lys |
| Leu | Thr<br>210 | Leu | Met | Phe | Arg | Val<br>215 | Gly | Asn | Leu | Arg | Asn<br>220 | Ser | His | Met | Val |
| Ser<br>225 | Ala | Gln | Ile | Arg | Cys<br>230 | Lys | Leu | Leu | Lys | Ser<br>235 | Arg | Gln | Thr | Pro | Glu<br>240 |
| Gly | Glu | Phe | Leu | Pro<br>245 | Leu | Asp | Gln | Leu | Glu<br>250 | Leu | Asp | Val | Gly | Phe<br>255 | Ser |
| Thr | Gly | Ala | Asp<br>260 | Gln | Leu | Phe | Leu | Val<br>265 | Ser | Pro | Leu | Thr | Ile<br>270 | Cys | His |
| Val | Ile | Asp<br>275 | Ala | Lys | Ser | Pro | Phe<br>280 | Tyr | Asp | Leu | Ser | Gln<br>285 | Arg | Ser | Met |
| Gln | Thr<br>290 | Glu | Gln | Phe | Glu | Val<br>295 | Val | Val | Ile | Leu | Glu<br>300 | Gly | Ile | Val | Glu |
| Thr<br>305 | Thr | Gly | Met | Thr | Cys<br>310 | Gln | Ala | Arg | Thr | Ser<br>315 | Tyr | Thr | Glu | Asp | Glu<br>320 |
| Val | Leu | Trp | Gly | His<br>325 | Arg | Phe | Phe | Pro | Val<br>330 | Ile | Ser | Leu | Glu | Glu<br>335 | Gly |
| Phe | Phe | Lys | Val<br>340 | Asp | Tyr | Ser | Gln | Phe<br>345 | His | Ala | Thr | Phe | Glu<br>350 | Val | Pro |
| Thr | Pro | Pro<br>355 | Tyr | Ser | Val | Lys | Glu<br>360 | Gln | Glu | Glu | Met | Leu<br>365 | Leu | Met | Ser |
| Ser | Pro<br>370 | Leu | Ile | Ala | Pro | Ala<br>375 | Ile | Thr | Asn | Ser | Lys<br>380 | Glu | Arg | His | Asn |
| Ser<br>385 | Val | Glu | Cys | Leu | Asp<br>390 | Gly | Leu | Asp | Asp | Ile<br>395 | Ser | Thr | Lys | Leu | Pro<br>400 |
| Ser | Lys | Leu | Gln | Lys<br>405 | Ile | Thr | Gly | Arg | Glu<br>410 | Asp | Phe | Pro | Lys | Lys<br>415 | Leu |
| Leu | Arg | Met | Ser<br>420 | Ser | Thr | Thr | Ser | Glu<br>425 | Lys | Ala | Tyr | Ser | Leu<br>430 | Gly | Asp |
| Leu | Pro | Met<br>435 | Lys | Leu | Gln | Arg | Ile<br>440 | Ser | Ser | Val | Pro | Gly<br>445 | Asn | Ser | Glu |
| Glu | Lys<br>450 | Leu | Val | Ser | Lys | Thr<br>455 | Thr | Lys | Met | Leu | Ser<br>460 | Asp | Pro | Met | Ser |
| Gln<br>465 | Ser | Val | Ala | Asp | Leu<br>470 | Pro | Pro | Lys | Leu | Gln<br>475 | Lys | Met | Ala | Gly | Gly<br>480 |
| Pro | Thr | Arg | Met | Glu<br>485 | Gly | Asn | Leu | Pro | Ala<br>490 | Lys | Leu | Arg | Lys | Met<br>495 | Asn |
| Ser | Asp | Arg | Phe | Thr<br>500 | | | | | | | | | | | |

( 2 ) INFORMATION FOR SEQ ID NO:5:

( i ) SEQUENCE CHARACTERISTICS:
( A ) LENGTH: 391 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met<br>1 | Gly | Ala | Ser | Glu<br>5 | Arg | Ser | Val | Phe | Arg<br>10 | Val | Leu | Ile | Arg | Ala<br>15 | Leu |

```
Thr  Glu  Arg  Met  Phe  Lys  His  Leu  Arg  Arg  Trp  Phe  Ile  Thr  His  Ile
               20                  25                       30

Phe  Gly  Arg  Ser  Arg  Gln  Arg  Ala  Arg  Leu  Val  Ser  Lys  Glu  Gly  Arg
                35                  40                       45

Cys  Asn  Ile  Glu  Phe  Gly  Asn  Val  Asp  Ala  Gln  Ser  Arg  Phe  Ile  Phe
          50                  55                       60

Phe  Val  Asp  Ile  Trp  Thr  Thr  Val  Leu  Asp  Leu  Lys  Trp  Arg  Tyr  Lys
65                       70                  75                            80

Met  Thr  Val  Phe  Ile  Thr  Ala  Phe  Leu  Gly  Ser  Trp  Phe  Leu  Phe  Gly
                    85                  90                            95

Leu  Leu  Trp  Tyr  Val  Val  Ala  Tyr  Val  His  Lys  Asp  Leu  Pro  Glu  Phe
               100                 105                      110

Tyr  Pro  Pro  Asp  Asn  Arg  Thr  Pro  Cys  Val  Glu  Asn  Ile  Asn  Gly  Met
          115                      120                      125

Thr  Ser  Ala  Phe  Leu  Phe  Ser  Leu  Glu  Thr  Gln  Val  Thr  Ile  Gly  Tyr
     130                      135                  140

Gly  Phe  Arg  Phe  Val  Thr  Glu  Gln  Cys  Ala  Thr  Ala  Ile  Phe  Leu  Leu
145                      150                 155                           160

Ile  Phe  Gln  Ser  Ile  Leu  Gly  Val  Ile  Ile  Asn  Ser  Phe  Met  Cys  Gly
                    165                 170                           175

Ala  Ile  Leu  Ala  Lys  Ile  Ser  Arg  Pro  Lys  Lys  Arg  Ala  Lys  Thr  Ile
               180                 185                      190

Thr  Phe  Ser  Lys  Asn  Ala  Val  Ile  Ser  Lys  Arg  Gly  Gly  Lys  Leu  Cys
     195                      200                 205

Leu  Leu  Ile  Arg  Val  Ala  Asn  Leu  Arg  Lys  Ser  Leu  Leu  Ile  Gly  Ser
     210                      215                 220

His  Ile  Tyr  Gly  Lys  Leu  Leu  Lys  Thr  Thr  Ile  Thr  Pro  Glu  Gly  Glu
225                      230                 235                           240

Thr  Ile  Ile  Leu  Asp  Gln  Thr  Asn  Ile  Asn  Phe  Val  Val  Asp  Ala  Gly
               245                 250                      255

Asn  Glu  Asn  Leu  Phe  Phe  Ile  Ser  Pro  Leu  Thr  Ile  Tyr  His  Ile  Ile
          260                      265                      270

Asp  His  Asn  Ser  Pro  Phe  Phe  His  Met  Ala  Ala  Glu  Thr  Leu  Ser  Gln
     275                      280                      285

Gln  Asp  Phe  Glu  Leu  Val  Val  Phe  Leu  Asp  Gly  Thr  Val  Glu  Ser  Thr
290                      295                      300

Ser  Ala  Thr  Cys  Gln  Val  Arg  Thr  Ser  Tyr  Val  Pro  Glu  Glu  Val  Leu
305                 310                      315                           320

Trp  Gly  Tyr  Arg  Phe  Val  Pro  Ile  Val  Ser  Lys  Thr  Lys  Glu  Gly  Lys
               325                      330                           335

Tyr  Arg  Val  Asp  Phe  His  Asn  Phe  Gly  Lys  Thr  Val  Glu  Val  Glu  Thr
               340                      345                 350

Pro  His  Cys  Ala  Met  Cys  Leu  Tyr  Asn  Glu  Lys  Asp  Ala  Arg  Ala  Arg
          355                 360                      365

Met  Lys  Arg  Gly  Tyr  Asp  Asn  Pro  Asn  Phe  Val  Leu  Ser  Glu  Val  Asp
     370                 375                      380

Glu  Thr  Asp  Asp  Thr  Gln  Met
385                 390
```

( 2 ) INFORMATION FOR SEQ ID NO:6:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear -continued ( i i ) MOLECULE TYPE: peptide ( x i ) SEQUENCE DESCRIPTION: SEQ ID NO:6:

```
Ala Phe Trp Trp Ala Val Val Ser Met Thr Val Gly Tyr Gly Asp
 1               5                   10                  15
Met
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ser Phe Trp Trp Ala Thr Ile Thr Met Thr Thr Val Gly Tyr Gly Asp
 1               5                   10                  15
Ile
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Gly Phe Trp Trp Ala Val Val Thr Met Thr Thr Leu Gly Tyr Gly Asp
 1               5                   10                  15
Met
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ala Phe Trp Tyr Thr Ile Val Thr Met Thr Thr Leu Gly Tyr Gly Asp
 1               5                   10                  15
Met
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Cys Val Tyr Phe Leu Ile Val Thr Met Ser Thr Val Gly Tyr Gly Asp
 1               5                   10                  15
```

Val ( 2 ) INFORMATION FOR SEQ ID NO:11:

( i ) SEQUENCE CHARACTERISTICS:
       ( A ) LENGTH: 17 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:11:

Ala Leu Tyr Trp Ser Ile Thr Thr Leu Thr Thr Thr Gly Tyr Gly Asp
 1               5                  10                 15

Phe ( 2 ) INFORMATION FOR SEQ ID NO:12:

( i ) SEQUENCE CHARACTERISTICS:
       ( A ) LENGTH: 22 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:12:

Leu Gly Leu Leu Ile Phe Phe Leu Phe Ile Gly Val Ile Leu Phe Ser
 1               5                  10                 15

Ser Ala Val Tyr Phe Ala
                20

( 2 ) INFORMATION FOR SEQ ID NO:13:

( i ) SEQUENCE CHARACTERISTICS:
       ( A ) LENGTH: 22 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:13:

Leu Gly Leu Leu Ile Leu Phe Leu Ala Met Gly Ile Met Ile Phe Ser
 1               5                  10                 15

Ser Leu Val Phe Phe Ala
                20

( 2 ) INFORMATION FOR SEQ ID NO:14:

( i ) SEQUENCE CHARACTERISTICS:
       ( A ) LENGTH: 22 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:14:

Phe Leu Leu Leu Ile Ile Phe Leu Ala Leu Gly Val Leu Ile Phe Ala
 1               5                  10                 15

Thr Met Ile Tyr Tyr Ala
                20

( 2 ) INFORMATION FOR SEQ ID NO:15:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

```
Leu Gly Phe Leu Leu Phe Ser Leu Thr Met Ala Ile Ile Ile Phe Ala
 1               5                  10                  15
Thr Val Met Phe Tyr Ala
            20
```

( 2 ) INFORMATION FOR SEQ ID NO:16:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Leu Ala Gln Leu Val Ser Ile Phe Ile Ser Val Trp Leu Thr Ala Ala
 1               5                  10                  15
Gly Ile Ile His Leu Leu
            20
```

( 2 ) INFORMATION FOR SEQ ID NO:17:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Cys Thr Lys Leu Ile Ser Val Thr Leu Phe Ala Ile His Cys Ala Gly
 1               5                  10                  15
Cys Phe Asn Tyr Leu Ile
            20
```

( 2 ) INFORMATION FOR SEQ ID NO:18:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Gly Lys Ile Val Gly Ser Leu Cys Ala Ile Ala Gly Val Leu Thr Ile
 1               5                  10                  15
Ala Leu Pro Val Pro Val Ile Val
            20
```

( 2 ) INFORMATION FOR SEQ ID NO:19:

( i ) SEQUENCE CHARACTERISTICS:
        ( A ) LENGTH: 24 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:19:

```
Gly Lys Ile Val Gly Gly Leu Cys Cys Ile Ala Gly Val Leu Val Ile
1               5                   10                  15
Ala Leu Pro Ile Pro Ile Ile Val
                20
```

(2) INFORMATION FOR SEQ ID NO:20:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Gly Met Leu Val Gly Ala Leu Cys Ala Leu Ala Gly Val Leu Thr Ile
1               5                   10                  15
Ala Met Pro Val Pro Val Ile Val
                20
```

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Gly Lys Ile Phe Gly Ser Ile Cys Ser Leu Ser Gly Val Leu Val Ile
1               5                   10                  15
Ala Leu Pro Val Pro Val Ile Val
                20
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Gly Arg Thr Phe Leu Val Phe Phe Leu Leu Val Gly Leu Ala Met Phe
1               5                   10                  15
Ala Ser Ser Ile Pro Glu Ile Ile
                20
```

(2) INFORMATION FOR SEQ ID NO:23:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (x i) SEQUENCE DESCRIPTION: SEQ ID NO:23:

Asp Ile Phe Phe Met Met Phe Asn Leu Gly Leu Thr Ala Tyr Leu Ile
1               5                   10                  15
Gly Asn Met Thr Asn Leu Val Val
            20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 1..20
        (D) OTHER INFORMATION: /note="Nucleotides indicated as
            "N"are inosine."

(x i) SEQUENCE DESCRIPTION: SEQ ID NO:24:

AARGANGGNC GNTGYAAYMT                                                                   20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 1..20
        (D) OTHER INFORMATION: /note="Nucleotides indicated as
            "N"are inosine."

(x i) SEQUENCE DESCRIPTION: SEQ ID NO:25:

NCCNACNATN GAYTGRAANA                                                                   20

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:26:

CCTTATTGGT GCTGGTTTG                                                                    19

1

MAMMALIAN INWARD RECTIFIER POTASSSIUM CHANNEL CDNAS, HOST CELLS EXPRESSING THEM, AND SCREENING ASSAYS USING SUCH CELLS

This application is a continuation of U.S. patent application Ser. No. 08/103,445, filed Aug. 6, 1993, now U.S. Pat. No. 5,492,825.

ACKNOWLEDGEMENT

This invention was made with Government support under Grant No. P50MH48200 awarded by the National Institute of Health. The Government has certain rights in this invention. This invention was also made with support from the Muscular Dystrophy Association, Inc.

FIELD OF THE INVENTION

The invention relates generally to advances in the field of cell physiology, specifically, physiologic and recombinant methods useful to characterize cell function and physiology. Particularly, the invention relates to the molecular identity of two particular and distinct trans-membrane ion channels, the definition of the biophysical properties of these channels, the expression products of the genes which encode these channels and uses of the same. More particularly, the invention arises in part from the determination that the DNA sequence of the IRK1 gene (SEQ ID NO:1) encodes an inward rectifier potassium channel and the DNA sequence of the GIRK1 gene (SEQ ID NO:3) encodes a G protein coupled muscarinic potassium channel.

BACKGROUND OF THE INVENTION

The membranes found at the surface of mammalian cells perform functions of great importance relating to the integrity and activities of cells and tissues. Of particular interest is the study of ion channel biochemistry, physiology, pharmacology and biokinetics. These ion channels, which include sodium ($Na^+$), potassium ($K^+$) and calcium ($Ca^{2+}$) channels are present in all mammalian cells and control a variety of physiological and pharmacological processes.

Potassium channels are implicated in a broad spectrum of processes in excitable and non-excitable cells. These physiologic processes include regulation of heartbeat (Breitwieser, G. E. and Szabo, G. (1985) Nature 317:538, Logothetis, D. E. et al. (1987) Nature 325:321, Yatani, A. et al. (1987) Science 235:207, Yatani, A. et al. (1988) Nature 336:680, Brown, A. M. and Birnbaumer, L. (1990) Annu. Rev. Physiol. 52:197 and Kurachi, Y. et al. (1992) Progress in Neurobiol. 39:229), dilation of arteries (Nelson, M. T. et al. (1990) Nature 344:770), release of insulin (Rorsman, P. et al. (1991) Nature 349:77), excitability of nerve cells (Stanfield, P. R. et al. (1985) Nature 315:498, Williams, J. T. et al. (1988) J. Neurosci. 8:3499) and regulation of renal electrolyte transport (Wang, W. et al. (1992) Annu. Rev. Physiol. 54:81).

Several classes of $K^+$ channels have been identified based on their pharmacological and electrophysiological properties; these include voltage-gated, ATP-sensitive, muscarinic-activated, S type, SK $Ca^{2+}$-activated, $Na^+$-activated and inward rectifier types of $K^+$ channels (For review see Hille, B. *Ionic Channels of Excitable Membranes* 2d ed., Sinauer, Sunderland, Mass., 1992).

The best characterized class of $K^+$ channels are the voltage-gated $K^+$ channels. The prototypical member of this class is the protein encoded by the Shaker gene in *Drosophila melanogaster* (Papazian, D. M. et al. (1987) Science 237:749, Tempel, B. L. et al. (1987) Science 237:770 and Baumann, A. et al. (1987) EMBO J. 6:3419). Mammalian homologues of the Drosophila Shaker and related Shal, Shab and Shaw genes have been cloned (Wei, A. et al. (1990) Science 248:599, Tempel, B. L., Jan, Y. N. and Jan, L. Y. (1988) Nature 332:837, Baumann, A. et al. (1988) EMBO J. 7:2457, Frech, G. C. et al. (1989) Nature 340:642, Yokoyama, S. et al. (1989) FEBS Lett. 259:37, Cristie, M. J. et al. (1989) Science 244:221, Stuhmer, W. et al. (1989) EMBO J. 8:3235, Swanson, R. et al. (1990) Neuron 4:929 and Luneau, C. J. et al. (1991) Proc. Natl. Acad. Sci. USA 88:3932). Voltage-gated $K^+$ channels belong to the superfamily of voltage-gated and second messenger-gated cation channels (Jan L. Y. and Jan, Y. N. (1992) Cell 69:715 and Jan, L. Y. and Jan, Y. N. (1990) Nature 345:672). The proteins in this gene family contain one or four copies of an underlying structural motif characterized by six membrane-spanning segments (S1–S6), a putative voltage sensor (S4) and an S5–S6 linker (H5 or P region) involved in ion conduction. The vast majority of cloned $K^+$ channels share a structural organization to the above motif, thereby placing most of the cloned $K^+$ channels in the same $K^+$ channel superfamily. Only two cloned $K^+$ channels do not share the above structural organization. These are the minK channel (Takumi, T. et al. (1988) Science 242:1042) and the ROMK1 channel, an ATP-regulated $K^+$ channel (Ho, K. et al. (1993) Nature 362:31). Attempts to isolate inward rectifier $K^+$ channels using sequences derived from members of the voltage-gated $K^+$ channel gene family as probes have been unsuccessful. This suggests that the structural organization of the inward rectifier channels differs significantly from that of the voltage-gated $K^+$ channels.

The molecular features of the proteins which comprise the classes of $K^+$ channels which are not voltage-gated are, for the most part, unknown although pharmacological and physiological characteristics have been elucidated. Of particular interest are the inward rectifier $K^+$ channels.

Inward rectifier $K^+$ channels allow primarily $K^+$ influx but little $K^+$ outflux. These $K^+$ channels have been found in a variety of cell types including skeletal (Katz, B. (1949) Arch. Sci. Physiol. 2:285 and Starden, N. B. and Stanfield, P. R. (1978) J. Physiol. 67:621) and cardiac (Sakmann, B. and Trube, G. (1984) J. Physiol. 347:641) muscle cells, starfish and tunicate oocytes (Hagiwara, S. et al. (1976) J. Gen. Physiol. 67:621 and Okamoto, H. et al. (1976) J. Physiol. 254:607), neurons (Mayer, M. L. & Westbrook, G. L. (1983) J. Physiol. 340:19, Mihara, S. et al. (1987) J. Physiol. 390:335, Inoue, M. et al. (1988) J. Physiol. 407:177 and Williams, J. T. et al. (1988) J. Neurosci. 8:3499), glial cells (Barres, B. A. (1991) Current Opinion in Neurobiol. 1:354), blood cells (McKinney, L. C. and Gallin, E. K. (1988) J. Memb. Biol. 103:41 and Lewis, D. L. et al. (1991) FEBS Lett. 290:17) and endothelial cells (Silver M. R. & DeCoursey T. E. (1990) J. Gen. Physiol. 96:109).

The inward rectifier $K^+$ channels have significant roles in maintaining the resting potential and in controlling excitability of a cell. The physiological functions of the inward rectifier $K^+$ channels stem from their unique rectification property and consist of three parts (Hille, B. Ionic Channels of Excitable membranes, 2d ed., Sinauer, Sunderland, Mass., 1992). First, the absence of outward conductance at highly depolarized membrane potentials allows a cell that expresses predominantly the inward rectifier to maintain prolonged depolarization. This is important for the generation of prolonged action potentials in heart ventricular cells, and for the prevention of double fertilization of oocytes (Hagiwara, S.

and Jaffe, L. A. (1979) Annu. Rev. Biophys. Bioeng. 8:385). Second, the large inward conductance at membrane potentials below the $K^+$ equilibrium potential ($E_K$) prevents excessive hyperpolarization, which may be caused by the electrogenic $Na^+$ pump (Hille, B., supra). Third, the slight outward conductance of inward rectifier $K^+$ channels at membrane potentials just above $E_K$ helps to keep the resting membrane potential close to $E_K$. Modulation of this conductance level changes the resting potential and alters the excitability of the cell. For example, it is well known that the activation of a particular type of inward rectifier $K^+$ channel, the muscarinic $K^+$ channel, by acetylcholine causes hyperpolarization of the cardiac pacemaker cells and slows the heartbeat (Noma, A. et al. (1979) Pflugers Arch. 381:255).

The inward rectification properties essential for the physiological functions of these $K^+$ channels have been characterized at the mechanistic level. These channels are permeable to an inward flow of $K^+$ ions at membrane potentials below $E_K$, which may be varied by changing the extracellular $K^+$ ion concentration (Hagiwara, S. et al. (1976) J. Gen. Physiol. 67:621). Therefore, the inward rectifier $K^+$ channels do not activate over a fixed range of membrane potentials, unlike voltage-gated $K^+$ channels. The inward rectification has been shown to be mainly due to the blockade of outward current by internal $Mg^{2+}$; in the absence of $Mg^{2+}$, inward rectifier $K^+$ channels exhibit a linear current-voltage relation (Matsuda, K. et al. (1987) Nature 325:156, Vandenberg, C. A. (1987) Proc. Natl. Acad. Sci. USA 84:2560 and Matsuda, H. (1988) J. Physiol. 397:237).

The extensive interaction of the inward rectifier $K^+$ channel pore with permeant ions and blocking ions has been well documented. These studies reveal that the inward rectifier $K^+$ channel has a long-pore with multiple binding sites; permeant ions enter the pore in single file and exhibit discernible interactions with other ions that either permeate or block the pore (Hille, B., supra, Hagiwara, S. et al. (1977) J. Gen. Physiol. 70:269 and Ohmori, H. (1980) J. Memb. Biol. 53:143). Interactions between permeant ions are manifested by the fact that $K^+$ conductance of the inward rectifier does not increase linearly with $K^+$ concentration (Sakmann, B. and Trube, G., supra). Extracellular cations such as barium ($Ba^{2+}$) and cesium ($Cs^+$) block the inward rectifier in a manner that depends both on the voltage and on the time elapsed following channel activation. This suggests that these blocking ions enter the open channel pore so that they sense part of the voltage drop across the membrane (Hagiwara, S. et al. (1976) J. Gen. Physiol. 67:621). The steepness of this voltage dependence of the block further indicates that there are multiple binding sites for $Cs^+$ in the channel pore (Hagiwara, S. et al. (1976) J. Gen. Physiol. 67:621 and Hille, B., supra).

Ion channel function can be regulated by various substances, such as hormones and neurotransmitters, via specific membrane receptors. Two major categories of receptor-operated ion channels are known. One class consists of ion channels which have an intrinsic sensor; the receptor site and a channel pore are present in the same polypeptide. The other class consists of ion channels having a remote sensor; the receptor site and the ion channel are different membrane proteins. G Protein is often involved in the remote-sensing ion channel models of transmembrane signalling.

An important receptor involved in the regulation of heart rate, the muscarinic receptor, slows heart rate upon activation by parasympathetic nerve stimulation (Trautwein, W. and Dudel, J. (1958) Pflugers Arch. 266:324, Noma, A. et al. (1979) Pflugers Arch. 381:255, Sakmann, B. et al. (1983) Nature 303:250 and Soejima, M. and Noma, A. (1984) Pflugers Arch. 400:424). The heart rate is slowed by the opening of the muscarinic $K^+$ channel. This ion channel has a remote sensor as the muscarinic receptor and $K^+$ channel exist as separate protein molecules.

The muscarinic $K^+$ channels in the sinoatrial node and atrium, the pacemaker of the heart, are inward rectifying $K^+$ channels and are known to be directly coupled with G proteins (Breitwieser, G. E. and Szabo, G. (1985) Nature 317:538, Logothetis, D. E. et al. (1987) Nature 325:321, Yatani, A. et al. (1987) Science 235:207, Yatani, A. et al. (1988) Nature 336:680, Brown, A. M. and Birnbaumer, L. (1990) Annu. Rev. Physiol. 52:197 and Kurachi, Y. et al. (1992) Progress in Neurobiol. 39:229). G proteins are a class of proteins involved in intracellular signal transduction. The G protein senses when a ligand has occupied a cell surface receptor, binds GTP and activates another protein involved in the signal transduction pathway such as adenyl cyclase or an ion channel. In the case of the muscarinic receptor, the activated G protein opens the muscarinic $K^+$ channel causing an outflux of $K^+$ from the heart muscle cell.

While mechanistic studies have elucidated physiological and pharmacological properties of the muscarinic $K^+$ channel, no studies have been possible at a molecular level. The molecular cloning of the muscarinic K+ channel would allow the development of assay systems to identify compounds which selectively inhibit this ion channel thereby providing compounds useful for the regulation of heart rate in mammals.

The art needs molecular characterization of inward rectifier $K^+$ channels in order to elucidate the physiological functions and biophysical properties of these channels. An understanding of these properties will allow the regulation of the physiological functions performed by these $K^+$ channels, such as regulation of heartbeat and release of insulin. Additionally, the availability of gene sequences encoding these inward rectifier $K^+$ channels would enable assay systems which would allow the identification of materials capable of selectively blocking these channels. Presently compounds which effect $K^+$ channels are identified using a cell or a tissue in which multiple types of $K^+$ channels are present; accordingly it is not possible to determine that a given compound exerts its effect solely through its interaction with a given type of $K^+$ channel in the present assay. Indeed the $K^+$ channel modulating drugs currently used to treat physiological disorders mediated by a given class of $K^+$ channels often have undesirable side effects. The art needs a means to identify compounds which have a specific and selective effect on a single type of $K^+$ channel for the improved treatment of disease.

SUMMARY OF THE INVENTION

The present invention is grounded in the unequivocal finding that the IRK1 gene (SEQ ID NO:1) encodes an inward rectifier $K^+$ channel in mouse cells. The present invention is further grounded in the unequivocal finding that the GIRK1 gene (SEQ ID NO:3) encodes a G protein coupled muscarinic $K^+$ channel, an inward rectifier $K^+$ channel, in rat cells. Further research revealed the finding that functional inward rectifier $K^+$ channel expression products of encoding DNA of the IRK1 gene (SEQ ID NO:1), or functionally bioactive equivalents, provided the means for developing assays, methods and products for use pharmacologically in animals (including not only the rodent order), and homologously in human beings. Further research also revealed the finding that functional G protein coupled muscarinic $K^+$ channel expression products of encoding DNA of the GIRK1 gene (SEQ ID NO:3), or functionally bioactive equivalents, provided the means for developing assays, methods and products for use pharmacologically in animals (including not only the rodent order), and homologously in human beings.

Thus, the invention provides an assay for identifying materials having a modulating effect on inward rectifier $K^+$ channels, including the G protein coupled muscarinic $K^+$ channel, in a mammal which comprises the steps of: providing an expression system that produces a functional inward rectifier $K^+$ channel expression product from DNA sequences encoding a mammalian inward rectifier $K^+$ channel; contacting the expression system or the product of the expression system or its equivalent with one or more of a battery of test materials that can potentially modulate the bioactivity of the expression product or its equivalent and monitoring the effect of the test materials on the expression product or its equivalent and selecting a candidate or candidates from the battery of test materials capable of modulating the bioactivity of the inward rectifier $K^+$ channels.

The selecting step of the assay may preferably measure the capacity of the test materials to block the bioactivity of the product or its equivalent. In a preferred embodiment, the IRK1 gene (SEQ ID NO:1) may comprise a mouse inward rectifier $K^+$ channel gene. In another preferred embodiment, the GIRK1 gene (SEQ ID NO:3) may comprise a rat G protein coupled muscarinic $K^+$ channel gene. Furthermore, the functionally bioactive equivalent may preferably comprise a functional human inward rectifier or G protein coupled muscarinic $K^+$ channel expression product. This functionally active bioequivalent, in a preferred embodiment, may comprise a functional homologue of a human inward rectifier $K^+$ channel expression product, including a G protein coupled muscarinic $K^+$ channel expression product, which furthermore may comprise a product of synthetic derivation. In a preferred embodiment, the expression system may comprise a transfectant, the transfectant most preferably comprising a Xenopus oocyte harboring DNA operatively encoding the product or equivalent.

In accordance with another aspect of the invention, there is provided methods useful to regulate the release of insulin and to regulate the heartbeat in a mammal. These functions are known to be mediated by inward rectifier $K^+$ channels (Nichols, C. G. and Lederer, W. J. (1991) Am. J. Physiol. 261:H1675, Venkatesh, N. et al. (1991) Circ. Res. 69:623, and Rorsman, P. et al. (1991) Nature 349:77). These methods comprise effecting the steps outlined in the above-referenced assay and then contacting the mammalian cells with the candidates selected in the assay. The contacting step used in these methods is preferably accomplished via a composition containing the candidate as an essential component. Most preferably, the contacting is accomplished via administration to a human subject.

In another embodiment of the invention, there is provided, for the above-disclosed use, DNA (recombinant or cDNA) encoding the IRK1 (SEQ ID NO:2) and GIRK1 (SEQ ID NO:4) gene products or functionally bioactive equivalents thereof, and vectors and transfectants operatively harboring same. In a preferred embodiment, the DNA encodes the IRK1 gene product (SEQ ID NO:2). In another preferred embodiment, the DNA encodes the GIRK1 gene product (SEQ ID NO:4). In another preferred embodiment, there is provided a transfected cell comprising DNA encoding the IRK1 gene product (SEQ ID NO:2) or a functionally bioactive equivalent thereof. In yet another preferred embodiment, there is provided a transfected cell comprising DNA encoding the GIRK1 gene product (SEQ ID NO:4) or a functionally bioactive equivalent thereof.

In a particularly preferred embodiment, the transfected cell harboring either of the inward rectifier $K^+$ channel genes is a Xenopus oocyte. A further preferred embodiment provides vectors comprising the DNA encoding either the IRK1 (SEQ ID NO:2) or GIRK1 (SEQ ID NO:4) gene products or functionally bioactive equivalents thereof.

The invention is further directed to isolates of DNA encoding the IRK1 (SEQ ID NO:2) and GIRK1 (SEQ ID NO:4) gene products or functionally bioactive equivalents. It is further directed to expression vectors harboring such DNA comprising expression control elements operative in the recombinant host selected for the expression of such DNA and preferably comprising appropriate initiation (i.e., promoter and enhancer elements), termination, replication, and other sequences that functionally assist the integration of the expression vector into a recombinant host by transfection, optionally coupled with actual integration into the host's genome.

In respect of the recombinant DNA aspects of the invention, the technology is applicable directly in all of its aspects, for example: DNA isolate production; including DNA isolates capable of hybridizing to IRK1 (SEQ ID NO:2) or GIRK1 (SEQ ID NO:3) gene sequences under low stringency conditions; devising expression vectors for them; and producing transfected hosts.

Further, the invention is directed to the foregoing aspects and all of their associated embodiments as will be represented as equivalents within the skill of those in the art.

BRIEF DESCRIPTION OF THE DRAWINGS

FIG. 1b depicts the current-voltage (I–V) curve of the data shown in FIG. 1a.

FIGS. 2a, 2c, 2e and 2g depict traces elicited by steps to +50, +20, −10, −40, −70, −100, −130 and −160 mV in the presence various concentrations of the following ions: $K^{+(2a)}$, $Na^+$ (2c) $Ba^{2+}$ (2e) and $Cs^+$ (2g).

FIGS. 2b, 2d, 2f and 2h depict I–V plots of the data shown in FIGS. 2a, 2c, 2e and 2g, respectively.

FIG. 3b depicts I–V plot of the data shown in FIG. 3a.

FIGS. 4a(1)–(3) shows the nucleotide and deduced amino acid sequence of IRK1 (SEQ ID NOS:1 and 2).

FIG. 4b shows the alignment of the amino acid sequences of IRK1 (SEQ ID NO:2) and the ATP-regulated $K^+$ channel (ROMK1) (SEQ ID NO:5).

FIGS. 4c–4e depict the alignment of the amino sequences of IRK1 (SEQ ID NO:2) and other $K^+$ channel sequences in the H5 (4c)(SEQ ID NOS:6–11), S5 (4d) (SEQ ID NO:12–17) and S6 (4e) (SEQ ID NOS:18–23) (4e) regions.

FIGS. 7a(1)–(2) depict the nucleotide and deduced amino acid sequence of GIRK1 (SEQ ID NOS:3–4).

FIG. 7b depicts the alignment of the amino acid sequences of GIRK1 (SEQ ID NO:4), IRK1 (SEQ ID NO:2) and ROMK1 (SEQ ID NO:5).

FIG. 8a depicts current traces from oocytes injected with m2 muscarinic receptor and GIRK1 cDNA before and after application of carbachol. The carbachol-induced currents depicted are the difference between the former two sets of traces.

FIG. 8b depicts a I–V plot of the carbachol-induced traces shown in FIG. 8a.

FIG. 9a depicts single channel recordings from oocytes injected with GIRK1 and $G\alpha_{i2}$, $\beta_1$, $\gamma_2$ cDNA; one minute segments of continuous recordings are shown from a membrane in the cell-attached configuration (left panel), inside-out configuration in the absence of GTP (middle panel) and inside-out in the presence of GTP$_\gamma$S (right panel). Expanded traces from the segments indicated by the triangles are shown below.

FIG. 9b depicts the open probability measured from the traces shown in FIG. 9a.

FIG. 9c depicts single channel activity in the presence of cytoplasmic $Mg^{2+}$ in oocytes injected with GIRK1 and $G\alpha_{i2}$, $\beta_1$, $\gamma_2$ cDNA.

FIG. 9d depicts single channel activity of oocytes injected with GIRK1 and $G\alpha_{i2}$, $\beta_1$, $\gamma_2$ cDNA in cytoplasmic $Mg^{2+}$-free cytoplasmic solution.

FIG. 9e depicts I–V plots of single channel current from the data shown in FIG. 9c (●) and 9d (○).

DETAILED DESCRIPTION OF THE INVENTION

A. Definitions

Figure 1A:
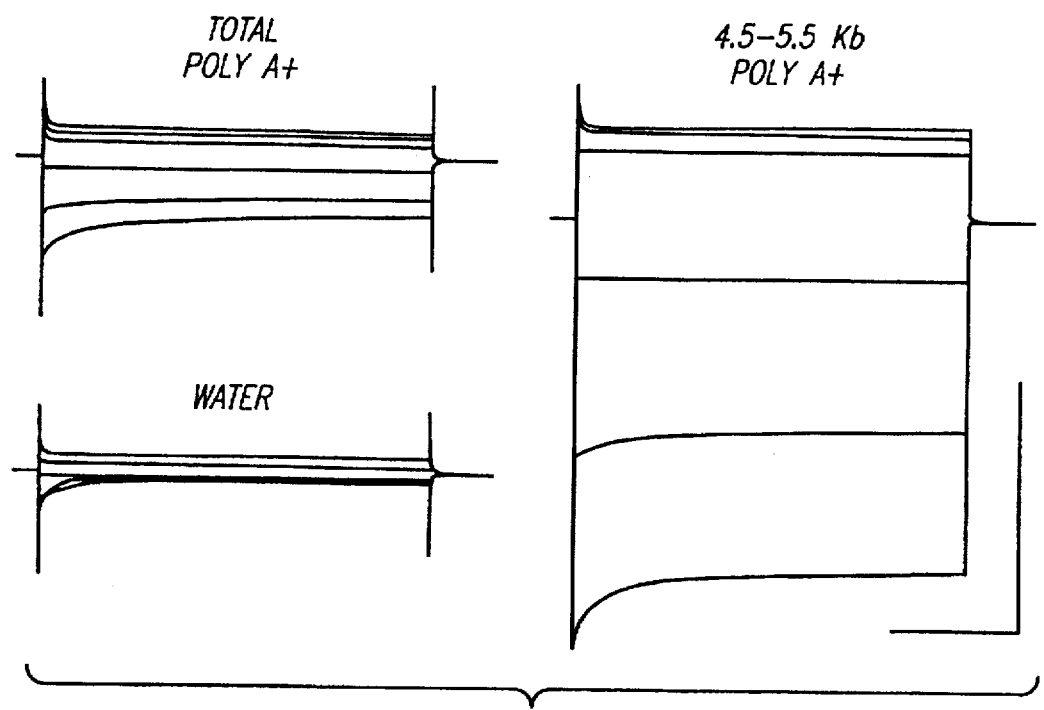
FIG. 1a depicts the inward rectifying currents induced in Xenopus oocytes by injection of total poly $A^+$ RNA from J774 cells, size fractionated RNA and water.

By the term "material" herein is meant any entity that is not ordinarily present or functional with respect to inward rectifier $K^+$ channels, including G protein coupled muscarinic $K^+$ channels, and that effects same. Thus, the term has a functional definition and includes known, and particularly, unknown entities that are identified and shown herein to have a modulating effect on inward rectifier $K^+$ channel expression, including G protein coupled muscarinic $K^+$ channel expression.

By the term "modulating effect", or grammatical equivalents, herein is meant both active and passive impact on inward rectifier $K^+$ channels, including G protein coupled muscarinic $K^+$ channels. These include, but shall not be construed as limited to, blocking the channel or the function of the channel protein(s), reducing the number of ion channels per cell and use of secondary cell(s) or channel(s) to impact on a primary abnormal cell.

By the term "measuring" in respect of effect of materials on inward rectifier $K^+$ channels, including G protein coupled muscarinic $K^+$ channels herein is meant any method known or devised for measuring the impact of a material on said channels/cells. These include, but shall not be construed as limited to, measuring current, measuring membrane potential, measuring $K^+$ flux, such as with radioactive tracers, measuring $K^+$ concentration and measurements of indirect consequences to other receptors, second messengers and/or channels.

By the term "functional" in respect of an inward rectifier $K^+$ channel expression product, including a G protein coupled muscarinic $K^+$ channel expression product, herein is meant that product works for its intended purpose, to wit, that it is bioreactive equivalently as is the direct product of either the IRK1 (SEQ ID NO:1) or GIRK1 (SEQ ID NO:3) gene as such.

The term "functionally bioactive equivalent" or "bioreactive equivalently" or grammatical equivalents thereof refers to mammalian proteins which perform the functions of the expression product encoded by either the IRK1 (SEQ ID NO:1) or GIRK1 (SEQ ID NO:3) gene. These bioactive mammalian proteins or homologues are capable of producing an expression product which functions as an inward rectifier $K^+$ channel of the type encoded by either the IRK1 (SEQ ID NO:1) or GIRK1 (SEQ ID NO:3) gene.

In a preferred embodiment, the inward rectifier $K^+$ channel expression product comprises an amino acid sequence encoded by a nucleotide sequence able to hybridize under low stringency conditions to the complement of a nucleotide sequence encoding the protein having the amino acid sequence shown in either FIG. 4a (SEQ ID NO:2) or FIG. 7a (SEQ ID NO:4).

The amino acid sequence encoded by the cross-hybridizable nucleotide sequence is preferably greater than about 40% homologous, more preferably greater than about 60% homologous, still more preferably greater than 70% homologous, even more preferably greater than about 80%, and most preferably at least about 90% homologous with the amino acid sequence shown in either FIGS. 4a(1)–(3) (SEQ ID NO:2) or FIGS. 7a(1)–(2).

"Homologous" is defined as the percentage of residues in the candidate amino acid sequence that are identical with the residues in the amino acid sequence shown in FIGS. 4a (SEQ ID NO:2) or FIGS. 7a(1)–(2) (SEQ ID NO:4) after aligning the sequences and introducing gaps, if necessary, to achieve the maximum percent homology.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "a DNA isolate" that is identified and separated from at least one contaminant nucleic acid with which it is ordinarily associated in its natural source. Isolated nucleic acid is such present in a form or setting that is different from that in which it is found in nature. However, isolated nucleic acid encoding a mammalian inward rectifier $K^+$ channel includes such nucleic acid in cells ordinarily expressing an inward rectifier $K^+$ channel where the nucleic acid is in a chromosomal location different from that of natural cells, or is otherwise flanked by a different DNA sequence than that found in nature.

"Low stringency conditions" are overnight incubation at 37° C. in a solution comprising: 20% formamide, 5× SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 1× SSC at about 50° C.

By the term "expression system" herein is meant matter capable of producing a functional inward rectifier $K^+$ channel expression product, including a G protein coupled muscarinic $K^+$ channel expression product. In preferred embodiments, such systems are micro-organisms, Xenopus oocytes or cell cultures harboring operatively DNA encoding such functional inward rectifier $K^+$ channel expression products, including G protein coupled muscarinic $K^+$ channel expression products. "Operative," or grammatical equivalents, means that the respective DNA sequences are operational, that is, work for their intended purposes. Thus, the DNA is preferably contained within expression vectors that are used to transfect recombinantly suitable host cells. The vectors and methods disclosed herein are suitable for use in host cells over a wide range of prokaryotic and eukaryotic organisms. "Transfectants" refers to cells and viruses which have been transfected or transformed with vectors constructed using recombinant DNA techniques, including expression systems including but not limited to, Xenopus and vaccina.

In general, prokaryotes are preferred for cloning of DNA sequences in constructing the vectors useful in the invention. For example, E. coli DH10B (Gibco BRL) is particularly useful. Other microbial strains which may be used include E. coli strains such as E. coli K12 strain 294 (ATCC No. 31446), E. coli B, and E. coli X1776 (ATCC No. 31537). These examples are, of course, intended to be illustrative rather than limiting.

Prokaryotes may also be used for expression. The aforementioned strains, as well as E. coli W3110 (F-, lambda-, prototrophic, ATCC No. 27235), bacilli such as Bacillus subtilus, and other enterobacteriaceae such as Salmonella typhimurium or Serratia marcestens, and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transfected cells. For example, E. coli is typically transformed using pBR322 or derivatives thereof. pBR322 is a plasmid derived from an E. coli species [Bolivar, et al., Gene 2, 95 (1977)]. pBR322 contains genes for ampicillin and tetracycline resistance and thus provides easy means for identifying transfected cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems [Chang, et al., Nature 275, 617 (1978), Itakura, et al., Science 198, 1056 (1977)], Goeddel, et al., Nature 281, 544 (1970)] and a tryptophan (trp) promoter system [Goeddel, et al., Nucleic Acids Res. 8 4057 (1980); EPO Appl Publ No. 0036776]. While these are the most commonly used, other microbial promoters have been discovered and utilized, and details concerning their nucleotide sequence have been published, enabling a skilled worker to ligate them functionally with plasmid vectors [Siebenlist, et al., Cell 20, 269 (1980)].

Additionally, phage vectors may be utilized in place of plasmid vectors. Examples of suitable phage vectors are provided in Sambrook, et al., Molecular Cloning: A Laboratory Manual, 2d ed., Cold Spring Harbor Laboratory, New York, 1989.

In addition to prokaryotes, eukaryotic microbes, such as yeast cultures may also be used. Saccharomyces cerevisiae, or common baker's yeast is commonly used among eukaryotic microorganisms, although a number of other strains are commonly available, such as Pichia strains, for example.

Suitable promoting sequences in yeast vectors include the promoters for 3-phosphoglycerate kinase [Hitzeman, et al., J. Biol. Chem. 255, 12073 (1980)] or other glycolytic enzymes [Hess, et al., J. Adv. Enzyme Reg. 7, 149 (1968) and Holland, et al., Biochemistry 17, 4000 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequences desired to be expressed to provide polyadenylation of the mRNA and termination. Other promoters, which have the additional advantage of transcription controlled by growth conditions are the promoter regions for the methanol-regulated alcohol oxidase I (AOX1) gene of Pichia pastoris (see EPA Publn. No. 183071), alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast compatible promoter, origin of replication and termination sequences is suitable.

In addition to microorganisms, cultures of cells derived from multicellular organisms may also be workable, whether from vertebrate or invertebrate culture. Examples of useful invertebrate cell lines include the Sf9 cell line (ATCC CRL 1711). However interest has been greatest in vertebrate cells, and propagation of vertebrate cells in culture (tissue culture) has become a common procedure in recent years [Tissue Culture, Academic Press, Kruse and Patterson, editors (1973)]. Examples of such useful host cell lines are VERO and HeLa cells, Chinese hamster ovary (CHO) cell lines, and 293, W138, BHK, COS-7 and MDCK cell lines. One such useful cell line is a CHO line, CHO-K1 ATCC No. CCL 61. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For invertebrate cells, the control functions on the expression vectors are often provided by viral material derived from Baculovirus. For mammalian cells, the control functions on the expression vectors are also often provided by viral material. For example, commonly used promoters are derived from polyoma, Adenovirus 2, Rous sarcoma virus, cytomegalovirus, and most frequently Simian Virus 40 (SV40). The early and late promoters of SV40 virus are particularly useful because both are obtained easily from the virus as a fragment which also contains the SV40 viral origin of replication [Fiers, et al., Nature 273,113 (1978)]. Smaller or larger SV40 fragments may also be used, provided there is included the approximately 250 bp sequence extending from the Hind III site toward the Bgl I site located in the viral origin of replication. Further it is also possible, and often desirable, to utilize promoter or control sequences ordinarily associated with the desired gene sequence, provided such sequences are compatible with host cell systems.

An origin of replication may be provided either by construction of the vector to include an exogenous origin, such as may be derived from SV40 or other viral (e.g., Polyoma, Adeno, VSV, BPV, etc.) source, or may be provided by the host cell chromosomal replication mechanism. If the vector is integrated into the host cell chromosomes, the latter is often sufficient.

If cells without formidable cell membrane barriers are used as host cells, transfection is carried out by the calcium phosphate precipitation method as described by Graham and Van der Eb, [Virology 52, 456 (1973)]. However, other methods for introducing DNA into cells such as by DEAE-dextran mediated transfection, microinjection, electroporation, retroviral infection, lipofection, biolistics or by protoplast fusion may also be used.

If prokaryotic cells or cells which contain substantial cell wall constructions are used, the preferred method of transfection is calcium treatment using calcium chloride as described by Cohen, F. N., et al., [Proc. Natl. Acad. Sci. (USA) 69, 2110 (1972)] or alternatively, electroporation.

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in a suitable buffer. In general, about 1 μl plasmid or DNA fragment is used with about 1 unit of enzyme in about 10–20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

Size separation of the cleaved fragments is performed using, for example, 6 percent polyacrylamide gel described by Goeddel, D., et al., Nucleic Acids Res. 8, 4057 (1980).

For ligation, approximately equimolar amounts of the desired components, suitable ends tailored to provide correct matching are treated with about 10 units T4 DNA ligase per 0.5 μg DNA. (When cleaved vectors are used as components, it may be useful to prevent religation of the cleaved vector by pretreatment with bacterial alkaline or calf intestinal phosphatase.)

For analysis to confirm correct sequences in plasmids constructed, the ligation mixture may be used to transform E. coli DH10B strain (Gibco BRL) or K12 strain 294 (ATCC No. 31446), and successful transformants selected by ampicillin, or tetracycline resistance where appropriate. Plasmids from the transformants are prepared, analyzed by restriction and/or sequenced by the method of Messing, et al., Nucleic Acids Res. 9, 309 (1981) or by the method of Maxam, et al., Methods of Enzymology 65, 499 (1980).

In addition to the above discussion and the various references to existing literature teachings, reference is made to standard textbooks of molecular biology that contain definitions and methods and means for carrying out basic techniques encompassed by the present invention. See, for example, Sambrook, et al., Molecular Cloning: A Laboratory Manual, 2d ed., Cold Spring Harbor Laboratory, New York, 1989 and the various references cited therein. All of the herein-cited publications are by this reference hereby expressly incorporated herein.

The present invention is thus directed to the identification, management, diagnosis and/or control of a disease state including:

(1) selectively screening for preferably selective modulators and/or blocking materials of inward rectifier $K^+$ channels, including G protein coupled muscarinic $K^+$ channels, for use as a diagnostic, and/or (2) blocking, retarding, modulating or eliminating selectively inward rectifier $K^+$ channels, including G protein coupled muscarinic $K^+$ channels for use as a therapeutic.

B. Preferred Embodiment

The foregoing description and following experimental details set forth the methodology employed initially by the present researchers in identifying, isolating, characterizing and determining the significance of the IRK1 (SEQ ID NO:2) and GIRK1 (SEQ ID NO:4) gene products in respect of physiological functions mediated via these inward rectifier $K^+$ channels. The art-skilled will recognize that by supplying such information for the IRK1 (SEQ ID NO:1) and GIRK1 (SEQ ID NO:3) genes, as detailed herein, it is not necessary, or perhaps even scientifically advisable, to repeat those details in their endeavors to reproduce this work. Instead, they may choose to employ alternative, reliable and known methods. Thus, they may identify related polypeptides via immuno cross-reactivity to antibodies raised to, for example, its reactive determinant(s). They may synthesize the underlying DNA sequence for deployment within similar or other suitable, operative expression vectors and culture systems. They may use the sequences herein to create probes, preferably from regions at both the N-terminus and C-terminus, to screen genomic libraries in isolating total encoding DNA for deployment as described above. They may Use the sequence information herein in crosshybridization procedures to isolate, characterize and deploy, as described above, DNA encoding related gene products of other species, or DNA encoding related (e.g., gene family) gene products of the same or other species, or to devise DNA for such characterization, use and deployment encoding functionally equivalent gene products of all of the above differing in one or more amino acids from the IRK1 (SEQ ID NO:2) or GIRK1 (SEQ ID NO:4) gene products or in glycosylation patterns or in bounded conformational structure.

Alternatively, DNA encoding related gene products of other species, or DNA encoding related (e.g., gene family) gene products of the same or other species may be isolated using the technique of the polymerase chain reaction (PCR). A pair of primers corresponding to two separate stretches of 7 or more highly conserved amino acids from the IRK1

(SEQ ID NO:1) or GIRK1 (SEQ ID NO:3) gene are synthesized and used in a PCR to isolate gene sequences corresponding to the IRK1 (SEQ ID NO:1) or GIRK1 (SEQ ID NO:5) genes from other species or to isolate gene sequences corresponding to other members of the inward rectifier gene family.

Thus, in addition to supplying details actually employed, the present disclosure serves to enable reproduction of the IRK1 (SEQ ID NO:2) and GIRK1 (SEQ ID NO:4) gene products disclosed and functionally bioactive equivalents, using means within the skill of the art having benefit of the present disclosure. All of such means are included within the enablement and scope of the invention.

EXAMPLES

1. Cloning of an Inward Rectifier $K^+$ Channel

Figure 1B:
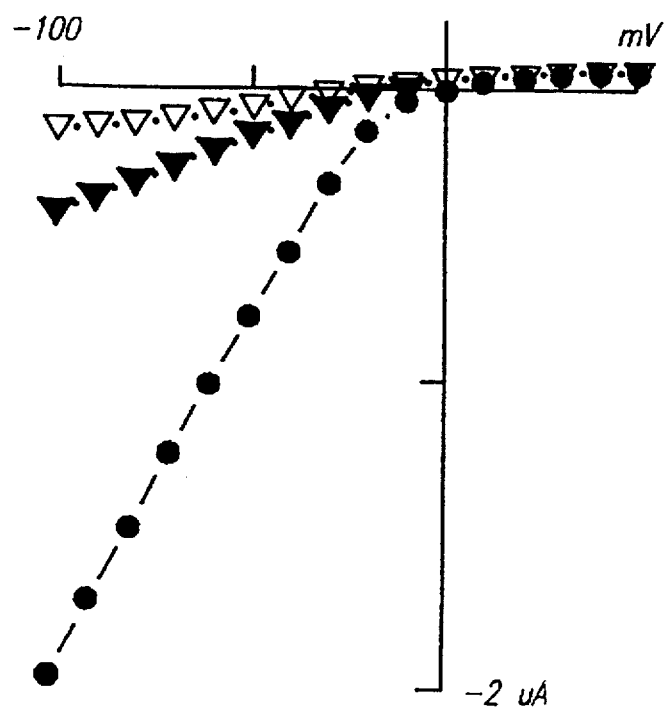

To identify a source for messenger RNA suitable for expression cloning of the inward rectifier, poly A+ RNA was isolated from various tissues (rat brain and skeletal muscle, rat and guinea pig heart, and cultured bovine aortic endothelial cells), and from various cell lines [C2C12 and L6 (myoblast), GH3 (pituitary), GT1-1 (neuroendocrine) and J774 (macrophage)]. Xenopus oocytes were injected with about 50 ng of poly $A^+$ RNA from various sources and membrane currents were recorded under two electrode voltage clamp in a 90 mM $K^+$ solution, which optimizes the detection of inward rectifier $K^+$ currents. As shown in FIGS. 1a and 1b, poly $A^+$ RNA from rat brain, GT1-1 cells and J774 cells induced detectable expression of an inward rectifier K+ current.

The J774 mouse macrophage cells were chosen for the subsequent studies, because the expressed current was large and highly susceptible to block by external $Ba^{2+}$. The sensitivity of the expressed current to the block by 100 μM external $Ba^{2+}$ enables it to be distinguished from the variable endogenous inward rectifying currents of the Xenopus oocytes (FIGS. 1a and 1b), which were unaffected by 100 μM external $Ba^{2+}$.

After size fractionation, poly $A^+$ RNA of 4.5–5.5 kb induced the largest current (FIGS. 1a and 1b), and was used for the construction of an unidirectional cDNA library.

Poly A+ RNA was isolated from J774 mouse macrophage cells using a Fast Track RNA isolation kit (Invitrogen) and fractionated as described (Meyuhas, O. and Perry, R. P. (1979) Cell 16:139). Briefly, 140 μg poly $A^+$ RNA was loaded on a 5–20% sucrose gradient and centrifuged at 21,000 rpm for 15.5 hours at 22° C. Thirty fractions were collected and analyzed electrophysiologically. The size range of RNA in each fraction was determined by electrophoresis on a formaldehyde agarose gel; poly $A^+$ RNA was detected with an oligo(dT) probe on the Nytran (S&S) RNA blot.

A cDNA library was constructed essentially as described (Aruffo, A. and Seed, B. (1987) Proc. Natl. Acad. Sci. USA 84:8573). Briefly, the 4.5–5.5 Kb enriched RNA fraction was reverse transcribed using MMV Superscript (BRL) at 42° C. by priming with Not1-oligo(dT) primer adaptors. After ligating a BstX1 adaptor and digestion with Not1, cDNA was size fractionated on a $K^+$ acetate gradient. cDNAs larger than 3 kb were ligated to a BstX1-Not1 digested pcDNA1/Amp plasmid (Invitrogen). Recombinant plasmids were electroporated into DH10B bacteria (BRL). The initial library was composed of 120,000 independent recombinants. This primary library was further size selected by digesting plasmids with Not1, selecting DNA fragments larger than 9 kb (about one quarter of the total library), then religating and transforming bacteria. Sixteen pools of 5,000 recombinants were screened. RNA was transcribed from Not1 digested DNA using methylated cap analogue and T7 polymerase as described (Baldwin, T. J. et al. (1991) Neuron 7:471),except that the reaction products were not treated with DNase. Subdivision of a positive pool was repeated until a single clone was obtained.

Figure 1C:
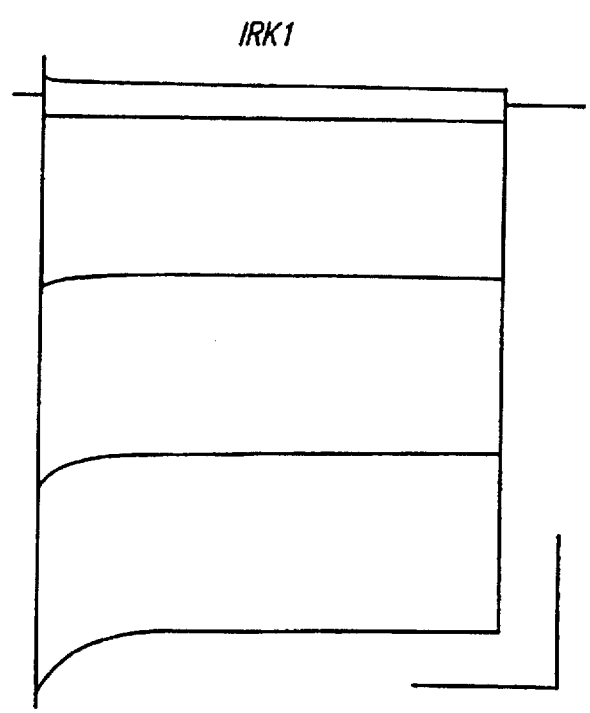
FIG. 1c depicts the inward rectifying currents induced in Xenopus oocytes by injection of RNA transcribed from the IRK1 cDNA clone.
Figure 1D:
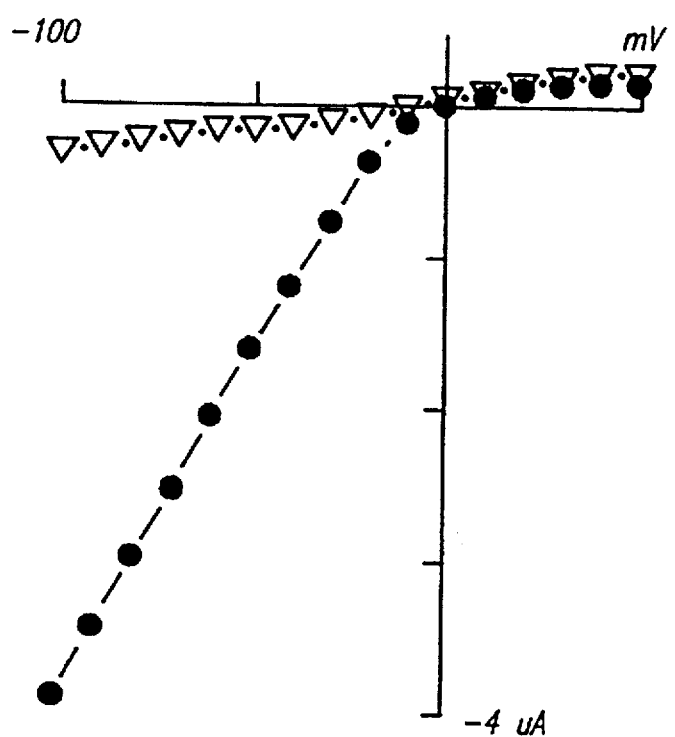
FIG. 1d depicts the I–V plot of the data shown in FIG. 1c.

A single clone (IRK1) (SEQ ID NO:1) isolated from this library, carrying a cDNA of 5.5 Kb, was sufficient to give rise to inward rectifier $K^+$ current in oocytes (FIGS. 1c and 1d). This K+ current resembles the current induced by total poly $A^+$ RNA from J774 cells in its rapid activation below $E_K$.

The electrophysiological studies shown in FIG. 1 were carried out as follows. Oocytes were injected with 50 nL RNA (1 μg/μl), and treated with collagenase for (2 mg/ml) for 2 h at room temperature. Electrophysiological recordings were carried out 48–96 h later at 22±2° C. by two-electrode voltage clamp (Baldwin, T. J. et al., supra). Data acquisition and analysis were done on an 80386-based microcomputer using pclamp program and TL–1A/D converter (Axon Instruments). Microelectrodes were filled with 3M KCl; the resistance was 0.7–1.4 Mohm. Bath solution contained 90 mM KCl, 3 mM $MgCl_2$, 5 mM HEPES (pH 7.4) (the 90 mM $K^+$ solution) with 300 μM niflumic acid to block $Cl^-$ channels.

The inward rectifying currents induced in oocytes injected with poly A+ RNA from the J774 cell line (FIG. 1a), water (FIG. 1a), size-fractionated poly $A^+$ RNA (FIG. 1a) and transcribed RNA from the IRK1 cDNA clone (SEQ ID NO:1) (FIG. 1c) are shown. Currents were recorded under two-electrode voltage clamp in 90 mM $K^+$ solution from injected oocytes. The holding potential was –30 mV (FIG. 1a), or 0 mV (FIG. 1c). Steps to +50, +20, –10, –40, –70 and –100 mV are shown. Scale bars indicate 500 ms and 1 μA. FIGS. 1b and 1d show I–V curve of the data shown in FIGS. 1a and 1c, respectively; Current amplitudes just after the capacitive transient (10 ms from the beginning of the voltage step) were plotted. Symbols in FIG. 1b represent total poly $A^+$ RNA (▼), 4.5–5.5 kb poly $A^+$ RNA (●);water (∇); and in FIG. 1d, IRK1 RNA (●); water (∇).

2. Electrophysiology of the IRK1 Current

The channel encoded by the IRK 1 cDNA clone (SEQ ID NO:1) is an authentic inward rectifier $K^+$ channel, because (1) the expressed current always activates at membrane potentials below $E_K$, (2) the slope conductance does not increase linearly with external K+ concentration; and (3) the current is blocked by external $Na^+$, $Ba^{2+}$ and $Cs^+$. The single channel conductance (21 pS) and inward rectification of the IRK1 single channel current are also characteristic of inward rectifier $K^+$ channels.

Figure 2A:
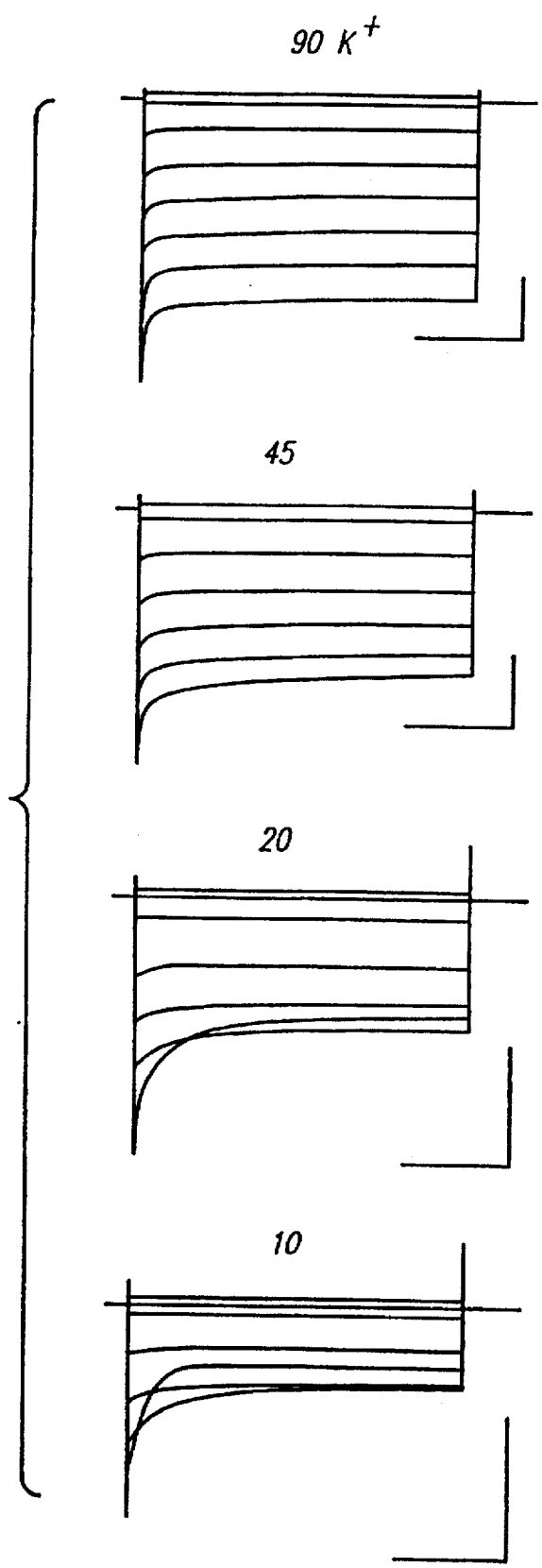
FIG. 2a–2h depict the inward rectifying currents induced in Xenopus oocytes by the IRK1 encoded $K^+$ channel and the response to the addition of external $Na^+$, $Ba^{2+}$ and $Cs^+$.
Figure 2B:
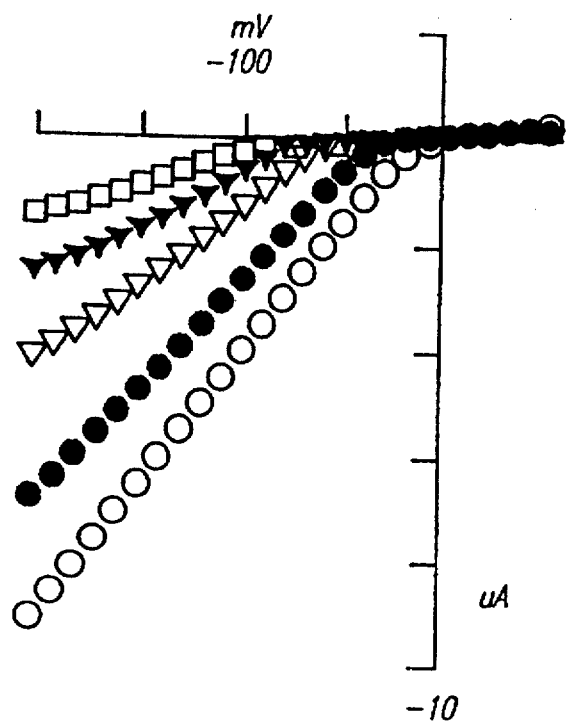

The salient feature of an inward rectifier is its ability to pass large inward $K^+$ current below $E_K$ but only minimal outward $K^+$ current (Hagiwara, S. et al. (1976) J. Gen. Physiol. 67:621). To investigate this feature, we varied $E_K$ by changing the $K^+$ concentration of the external solution and measured the activation potential of the IRK1 current, which showed strong inward rectification (FIGS. 2a and 2b). The activation potential is defined as the potential at which the slope conductance changes noticeably; the slope conductance is small at potentials more depolarized than the activation potential and begins to increase at the activation potential, reaching a high level at more hyperpolarized potentials. The activation potentials measured in three experiments were 0±2 mV (90 mM $K^+$), –17±2 mV (45 mM $K^+$), –41±2 mV (20 mM $K^+$), –56±2 mV (10 mM $K^+$) and –75±3 mV (4 mM $K^+$), which are in good agreement with $E_K$ in these solutions as predicted by the Nernst equation. These results show that the IRK1 channels are K+ channels which activate at membrane potentials below $E_K$ and pass inward $K^+$ currents.

Another characteristic feature of inward rectifiers is the non-linear dependence of conductance on $K^+$ concentration: the slope conductance varies with the square root of the external $K^+$ concentration (Sakmann, B. and Trube, G. (1984) J. Gen. Physiol. 347:641). Indeed, the double-logarithmic plot of the slope conductance versus extracellular $K^+$ concentration (4–20 mM) was fitted with a straight line of slope 0.47 ±0.03 (n=3). Thus, the IRK1 current mimics the inward rectifier currents in its deviation from the independence principle, thereby revealing interactions between $K^+$ ions as they go through the channel.

Figure 2D:
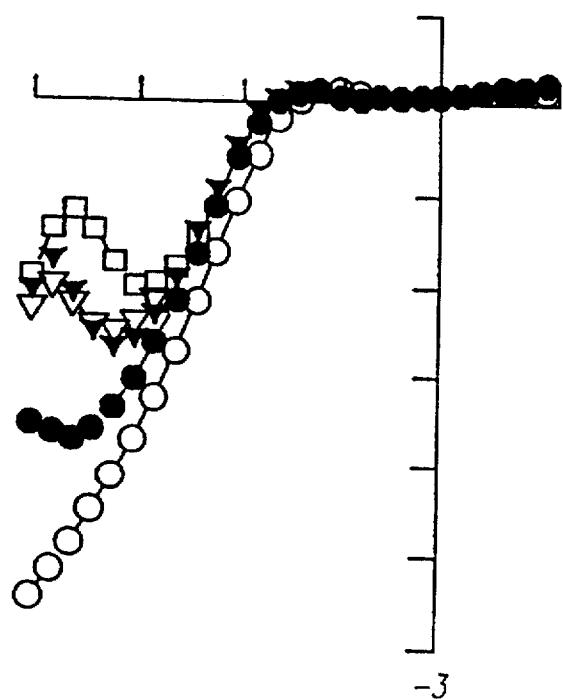
Figure 2C:
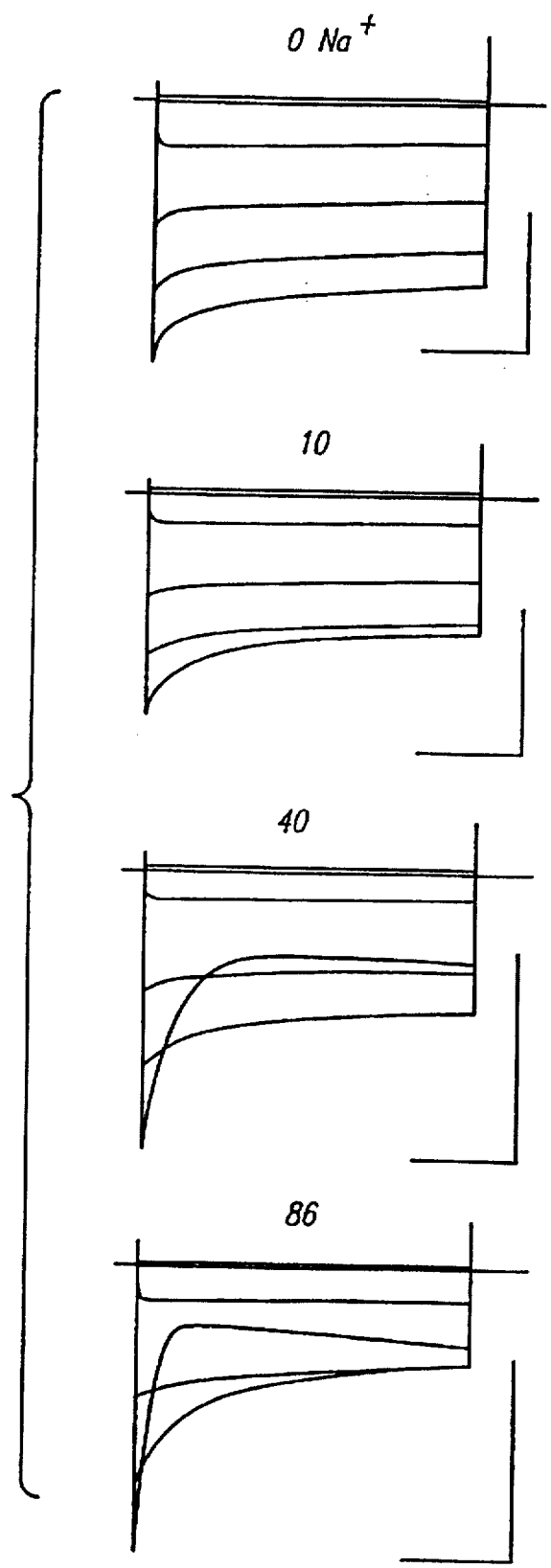

A third characteristic feature of inward rectifiers is their susceptibility to the block of the channel pore by extracellular cations (Standen, N. B. and Stanfield, P. R. (1978) J. Physiol. 280:169, Hagiwara, s. et al. (1976) J. Gen. Physiol. 67:621 and Sakmann, B. and Trube, G. (1984) J. Gen. Physiol. 70:269). Such a block was indicated by a prominent inactivation of the IRK1 current in solutions containing 20, 10 (FIG. 2a) or 4 mM $K^+$ and increased $Na^+$ concentrations. Indeed, in external solutions of varying Na+ concentrations (N-methylglucamine was used to maintain the ionic strength as the $Na^+$ concentration was varied, and the $K^+$ concentration was fixed at 4 mM), the inactivation increased with the external $Na^+$ concentration and was both voltage- and time-dependent (FIGS. 2c and 2d). In addition to this $Na^+$ block, the IRK1 channel was blocked in a voltage- and time-dependent manner by external $Ba^{2+}$ (FIGS. 2e and 2f) or $Cs^+$ (FIGS. 2g and 2h), suggesting that all three ions act as open channel pore blockers. The steep voltage dependence of $Cs^+$ block was quantitated by first plotting the ratios of steady-state current levels in the presence and absence of $Cs^+$ as a function of external $Cs^+$ concentration (to obtain $K_i$ for the $Cs^+$ block at each membrane potential), and then fitting the double logarithmic plot of $K_i$ versus membrane potential with a straight line. A tenfold change in $K_i$ corresponded to a change in membrane potential of 38.1 mV. This implies that the fractional distance of the $Cs^+$ binding site in the membrane electric field is 1.53, if we assume that only one $Cs^+$ enters the pore and blocks $K^+$ permeation. This apparent anomaly indicates that several $Cs^+$ ions reside in a single channel pore, as shown previously for inward rectifiers (Hagiwara, S. et al., supra, Hille, B., supra).

Figure 2E:
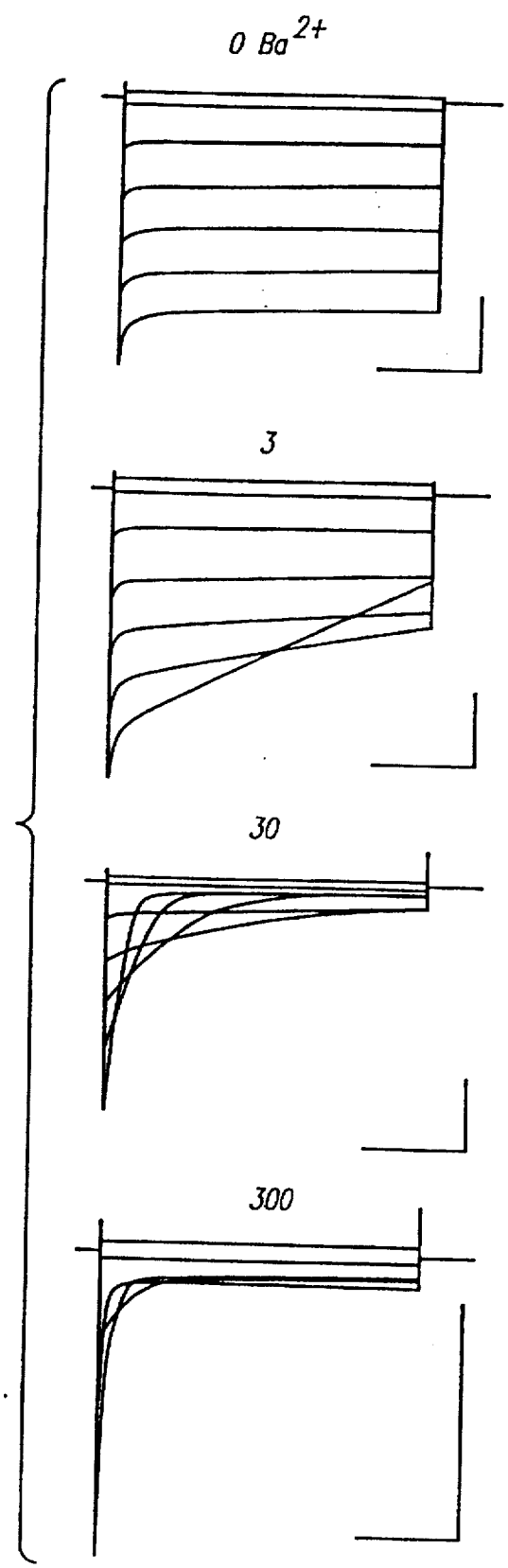
Figure 2F:
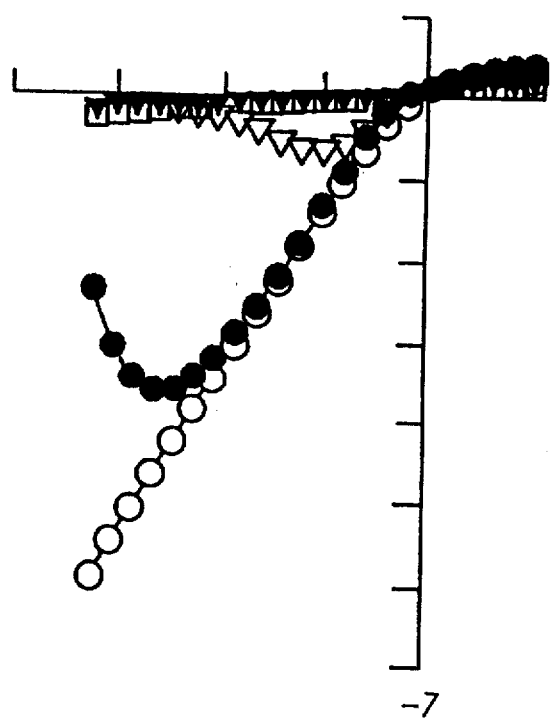
Figure 2H:
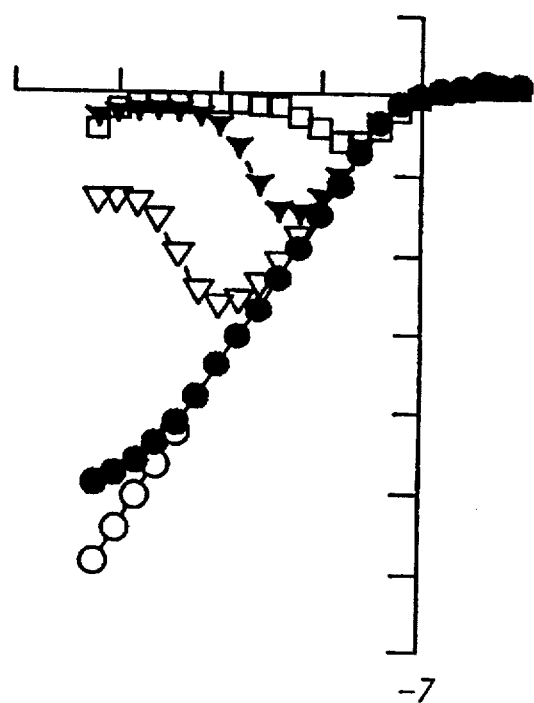
Figure 2G:
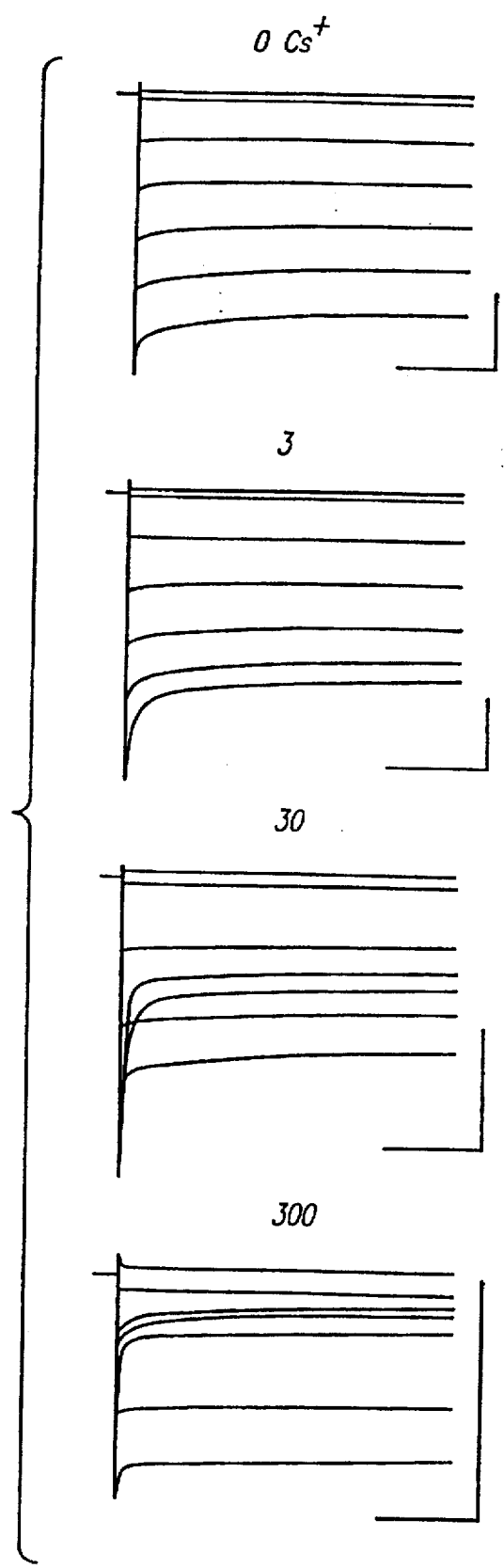

The data showing that the IRK1 $K^+$ current exhibits characteristic inward rectification properties and open channel block by external $Na^+$, $Ba^{2+}$, and $Cs^+$ (FIGS. 2a–2h) was generated as follows. Current recordings under voltage clamp are shown in FIGS. 2a, 2c, 2e and 2g. Holding potential was 0 mV. Traces elicited by steps to 50, +20, −10, −40, −70, −100, −130 and −160 mV are shown. An additional trace elicited by hyperpolarization to −190 mV is shown in FIGS. 2a and 2c. Scale bars indicate 500 ms and 2 µA (FIGS. 2a, 2c, 2e), 100 ms and 2 µA (FIG. 2g). Voltage- and time-dependent block of the IRK1 current is evident in 40 and 86 mM $Na^+$ (FIG. 2c), 30 µM $Ba^{2+}$(FIG. 2e) and 30 µM $Cs^+$ (FIG. 2g).

FIGS. 2b, 2d, 2f and 2h depict the I–V relations of the data shown in FIGS. 2a, 2c, 2e, 2g, respectively. Current amplitudes just after the capacitive transient (10 ms from the start of voltage pulses) are plotted in FIG. 2b, and current amplitudes at the end of the 1,600-ms voltage pulses are plotted in FIGS. 2d, 2f and 2h. For the experiments shown in FIGS. 2a and 2b, current recordings were performed in solutions of 90 mM (○), 45 mM (●), 20 mM(▽), 10 mM (▼) and 4 mM $K^+$ (□)(data not shown in 2a). $K^+$ was substituted with $Na^+$. $E_K$ values in these solutions, as predicted by the Nernst equation, were 0 mV (90 mM $K^+$), −17.4 mV (45 mM $K^+$), −37.9 mV (20 mM $K^+$), −55.3 mV (10 mM $K^+$) and −78.4 mV (4 mM $K^+$). (The intracellular $K^+$ concentration of oocytes was assumed to be 90 mM, according to previous description in Dascal, N. (1987) Crit. Rev. Biochem. 22:317). IRK1 current in 90 mM $K^+$ solution showed slight inactivation shortly after channel activation (within 200 ms), which could be due to block by certain extracellular ions such as $Mg^{2+}$ (Biermans, G. et al. (1987) Pflugers Arch. 410:604).

In FIGS. 2c and 2d current recordings were performed in solutions of 0 mM (○), 10 mM (●), 20 mM (▽) (data not shown in 2c), 40 mM (▼) and 86 mM $Na^+$ (□)solution. All solutions contained 4 mM K+, 3 mM $Mg^{2+}$, 5 mM HEPES (pH 7.4). $Na^+$ was replaced with N-methylglucamine. The sum of $Na^+$ and N-methylglucamine was 86 mM. In FIGS. 2e and 2f current recordings were performed in solutions of 0 µM(○), 3 µM (●), 30 µM (▽), 300 µM (▼) and 3 mM $Ba^{2+}$(□) (data not shown in 2e). $BaCl_2$ was added to 90 mM $K^+$ solution without correcting the ionic strength. For FIGS. 2g and 2 h current recordings were performed in solutions of 0 µM (○), 3 µM (●), 30 µM (▽), 300 µM (▼) and 3 mM $Cs^+$ (□) (data not shown in 2g). CsCl was added to 90 mM $K^+$ solution without correcting the ionic strength.

By demonstrating $K^+$ selectivity, inward rectification and interactions between permeant ions and blocking ions, the results show that the IRK1 channel is an inward rectifier K+ channel. Apart from the inward rectifier $K^+$ channels, cardiac muscarinic $K^+$ channels and ATP-sensitive $K^+$ channels also show moderate inward rectification (Matsuda, H. (1991) J. Physiol. 53:289, Horie, M. and Irisawa, H. (1989) J. Physiol. 408:313 and Horie, M. et al. (1987) J. Gen. Physiol. 387:251). The outward $K^+$ conductances of these two types of channels are much larger than that of the IRK1 channel. In addition, the single channel conductance of IRK1 channels in cell attached patches was 21±2 pS (n=4) (140 mM external K+/−90 mM intracellular $K^+$, at 21±2° C.) (FIGS. 3a and 3b), which is similar to that of inward rectifiers (20–30 pS, McKinney, L. C. and Gallin, E. K. (1988) J. Memb. Biol. 103:41 and Matsuda, H. (1988) J. Physiol. 397:237) but smaller than those of muscarinic K+ channels (45 pS, Horie, M. and Irisawa, H. (1989) J. Physiol. 408:313) or ATP-sensitive channels (80 pS, Horie, M. et al. (1987) J. Physiol. 387:251). The relatively long open time of the IRK1 channel, and the tendency of the open time to shorten and of the open probability to decrease with increasing hyperpolarization (FIG. 3a), are also characteristic of the inward rectifiers (Matsuda, H., supra and Ohmori, H. (1980) J. Memb. Biol. 53:143).

IRK1 channels in excised inside-out patches rapidly became inactive (within 0.5–15 min; n=7), which resembles the reported run-down of inward rectifiers (McCloskey, M. A. and Cahalan, M. D. (1990) J. Gen. Physiol. 95:205, muscarinic $K^+$ channels (Ito, H. et al. (1991) J. Gen. Physiol. 95:205 and Kurachi, Y. et al. (1992) Prog. Neurobiol. 39;229) and ATP-sensitive $K^+$ channels (Horie, M. et al. (1987) supra and Kurachi, Y. et al. (1992), supra). Unlike the muscarinic K+ channels (Ito, H. et al. (1991), supra and Kurachi, Y. et al. (1992), supra), however, the IRK1 channel activity is not restored by 100 µM internal GTP-γS. In contrast to ATP-sensitive $K^+$ channels, which require micromolar concentrations of internal Mg-ATP to prevent run-down, but which are blocked by internal ATP at millimolar concentrations (Horie, M. et al. (1987) supra and Kurachi, Y. et al. (1992), supra), the IRK1 channel exhibited run-down in solutions containing 2.5 mM or 25 μM ATP. Finally, a specific blocker of ATP-sensitive K⁺ channel, tolbutamide (100 μM, Trube, G. et al. (1986) Pflugers Arch. 407:493) did not affect the IRK1 current.

The experiments shown in FIGS. 3a and 3b were carried out as follows. Single channel recordings were made in the cell attached or the inside-out excised patch configuration of the patch clamp, using an EPC7 amplifier (List) at 22°–25° C. The pipette solution was 140 mM KCl, 3 mM $MgCl_2$, 5 mM HEPES (pH 7.4). The bath solution was 110 mM KCl, 10 mM $MgCl_2$, 2 mM $K_2ATP$, 5 mM EDTA, 5 mM HEPES, 25 mM KOH (pH 7.2). Total K⁺ concentration was 140 mM, and the free $Mg^{2+}$ concentration was calculated to be 3 mM. Data were filtered at 1 kHz by an 8-pole bessel filter, sampled at 2–8 kHz through an A/D converter TL1, and stored in 80386-based computer. Single channel current amplitudes were determined by fitting lines to recordings at each potential. The slope conductance was determined from a straight line fitted by eye.

Figure 3A:
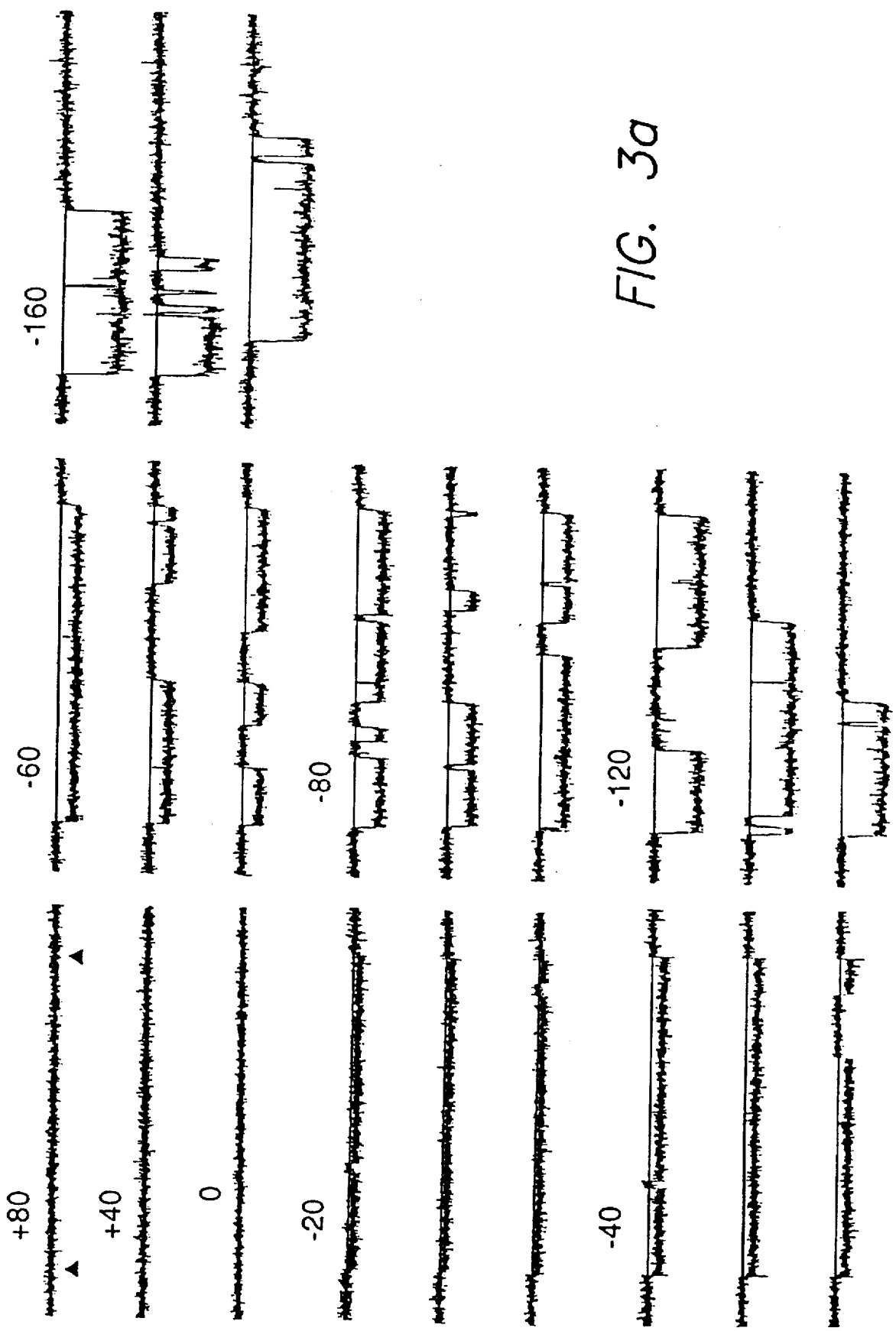
FIG. 3a depicts single channel activities of the IRK1 $K^+$ channel. Current recordings are shown at the voltages indicated.
Figure 3B:
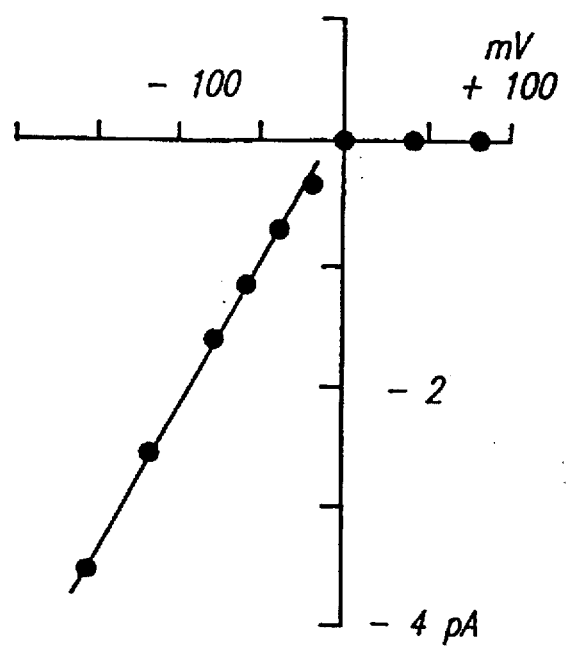

FIG. 3a shows current recordings of single channel activities elicited by voltage steps to various potentials from 0 mV in the cell attached mode. The linear leakage and capacitive components were subtracted using averaged blank records. At −40 mV, as there were no blank traces recorded, records at +40 mV were used as leak templates. The potentials shown represent the pipette potential, the difference between the membrane potential and the pipette potential is the resting potential of the oocyte, which could range between 0 and −10 mV in the high K⁺ solution. Scale bars indicate 200 ms and 2.5 pA. Triangles show beginning and end of voltage steps. FIG. 3b shows a I–V plot of the single channel current shown in FIG. 3a. V axis shows the pipette potential; the straight line was fitted by eye. The slope conductance was 23 pS.

Thus the properties of the IRK1 channel resemble closely those of inward rectifier K+ channels but differ from ATP-sensitive K⁺ channels or muscarinic K⁺ channels. A plant K⁺ channel (KAT1 from Arabidopsis) has been found to be inwardly rectifying, but it activates at a hyperpolarized membrane potential (−80 mV) regardless of $E_K$ (Schachtman, D. P. et al (1992) Science 258:1654). This plant K⁺ channel, thus, differs from IRK1 and classical inward rectifier K+ channels in the mechanism of inward rectification.

3. Primary Structure of the IRK1 Channel

The nucleotide and deduced amino acid sequence of IRK1 (SEQ ID NOS:1 and 2) is shown in FIG. 4a(1)–(3). The IRK1 (SEQ ID NO:1) cDNA was sequenced on both strands using Sequenase (USB Corp.). The deduced amino acid sequence (SEQ ID NO:2) is displayed above the nucleotide sequence (SEQ ID NO:1) of the coding strand of the IRK1 cDNA (SEQ ID NO:1). Nucleotide A of the initiation codon (ATG) is assigned as +1. The IRK1 clone (SEQ ID NO:1) is approximately 5.5 kb long and has only one long open reading frame which predicts a protein of 428 amino acids (SEQ ID NO:2). Only part of the 3' untranslated sequence is shown. The transmembrane segments M1 and M2 are boxed. Also boxed is a segment with sequence similarity to the H5 region of the voltage-gated K⁺ channel. There is one potential cAMP and cGMP-dependent protein kinase phosphorylation site (Ser 426), four potential protein kinase C phosphorylation sites (Ser 3, Thr 6, Ser 357, Thr 383), and two tyrosine kinase phosphorylation sites (Tyr 242, Tyr 366).

Sequence analysis reveals that the structure of IRK1 (SEQ ID NO:2) is similar to that of an ATP-regulated K⁺ channel, ROMK1 (SEQ ID NO:5) (40% amino acid identity, Ho, K. et al. (1993) Nature 362:31). The amino acid sequences of IRK1 (SEQ ID NO:2) and ROMK1 (SEQ ID NO:5) are aligned in FIG. 4b. A vertical line indicates amino acid identity; a period indicates amino acid similarity. Amino acids within each of the following groups were classified as similar (one letter code): A, S and T; D and E; N and Q; R and K; I, L, M and V; F, Y and W. Dashes indicate gaps introduced into the sequence to improve alignment. The proposed transmembrane regions M1 and M2 and the H5 like segments are boxed. The ATP binding site in ROMK1 (SEQ ID NO:5) is doubly underlined. By use of Monte Carlo and Needleman-Wunch statistical analysis, these two sequences were determined to be significantly related. No other sequences with significant similarity to the IRK1 amino acid sequence (SEQ ID NO:2) were detected in the GenBank or EMBL data bases.

FIGS. 4c, 4d and 4e show the alignment of the IRK1 (SEQ ID NO:2) and other K⁺ channel sequences in the H5 (FIG. 4c) (SEQ ID NOS:6–11), S5 (FIG. 4d) (SEQ ID NOS:12–17) and S6 (FIG. 4e) (SEQ ID NOS:18–23) region. Boxed residues are identical to those of the IRK1 at the corresponding positions. The K⁺ channels included in these alignments are: voltage-gated K⁺ channels of the Shaker subfamily (Kv1.1/RCK1, Stuhmer, W. et al. (1989) EMBO J. 8:3235), the Shab subfamily (Kv2.1/drk1, Frech, G. C. et al (1989) Nature 340:642) the Shaw subfamily (Kv3.1/NGK2, Yokoyama, S. et al. (1989) FEBS Lett. 259:37) and the Shal subfamily (Kv4.1/mouse Shal, Pak, M. D. et al. (1991) Proc. Natl. Acad. Sci. USA 88:4386), a $Ca^{2+}$-dependent K⁺ channel (slo, Atkinson, N. S. et al. (1991) Science 253:551) and a plant K⁺ channel (KAT1, Anderson, J. A. et al. (1992) Proc. Natl. Acad. Sci. USA 89:3736).

The nucleotide and deduced amino acid sequences of the IRK1 cDNA clone (SEQ ID NOS:1 and 2) (FIGS. 4a(1)–(3)) reveal that the structure of IRK1 (SEQ ID NO:2) is similar to that of ATP-sensitive K⁺ channel (FIG. 4b), but different from that of voltage-gated K⁺ channels. Hydrophobicity analysis indicates the presence of only two potentially membrane-spanning hydrophobic segments (M1, M2). Although IRK1 has fewer hydrophobic segments than voltage-gated K⁺ channel polypeptides, extensive similarity to the H5 pore region of voltage-gated K⁺ channels (Miller, C. (1991) Science 252:1092) was found for a segment between M1 and M2 (FIG. 4c). Several residues of M1 and M2 are also identical to corresponding residues in S5 and S6 respectively, which are highly conserved among voltage-gated K⁺ channels (FIGS. 4d and 4e). The IRK1 sequence contains no hydrophobic segments that correspond to S1, S2 or S3 of voltage-gated K⁺ channels, and only limited sequence similarity to S4 could be detected in the N-terminal region of IRK1 (SEQ ID NO:2). As no N-terminal signal sequence was detected, the amino-terminus is proposed to be on the cytoplasmic side of the membrane.

Figure 6:
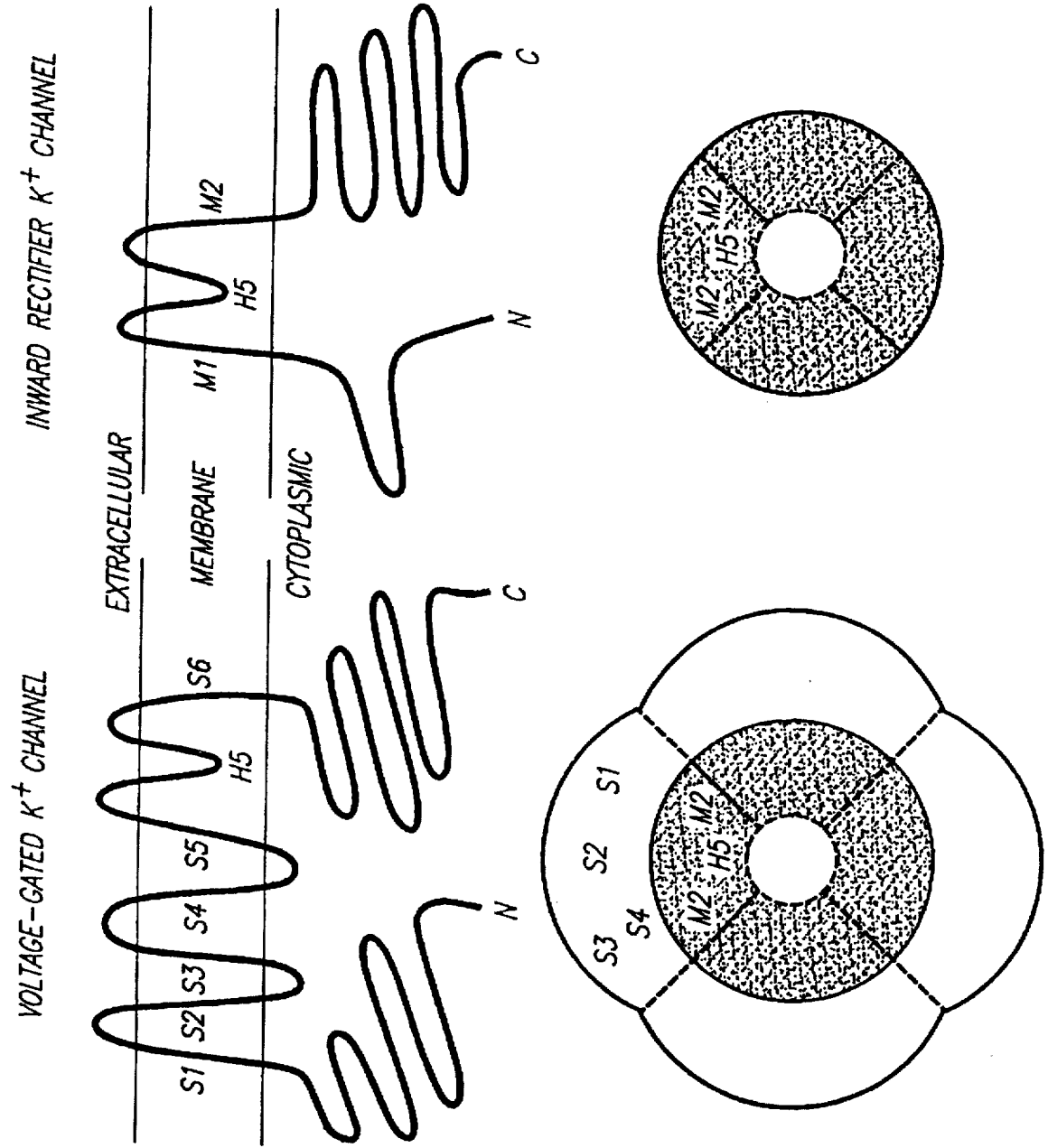
FIG. 6 depicts the proposed membrane topology of the IRK1 encoded inward rectifier $K^+$ channel (right) and proposed membrane topology of the voltage-gated $K^+$ channel (left).

The membrane topology of the IRK1 channel and the ATP-sensitive K⁺ channel is likely to resemble that of the S5, H5 and S6 segments of the voltage-gated K⁺ channel (see FIG. 6, discussed infra). Thus, these two K⁺ channels belong to a new family which is related to, but distinct from, the superfamily of voltage-gated K⁺ channels.

4. Distribution of IRK1 mRNA in Mouse Tissues

Figure 5:
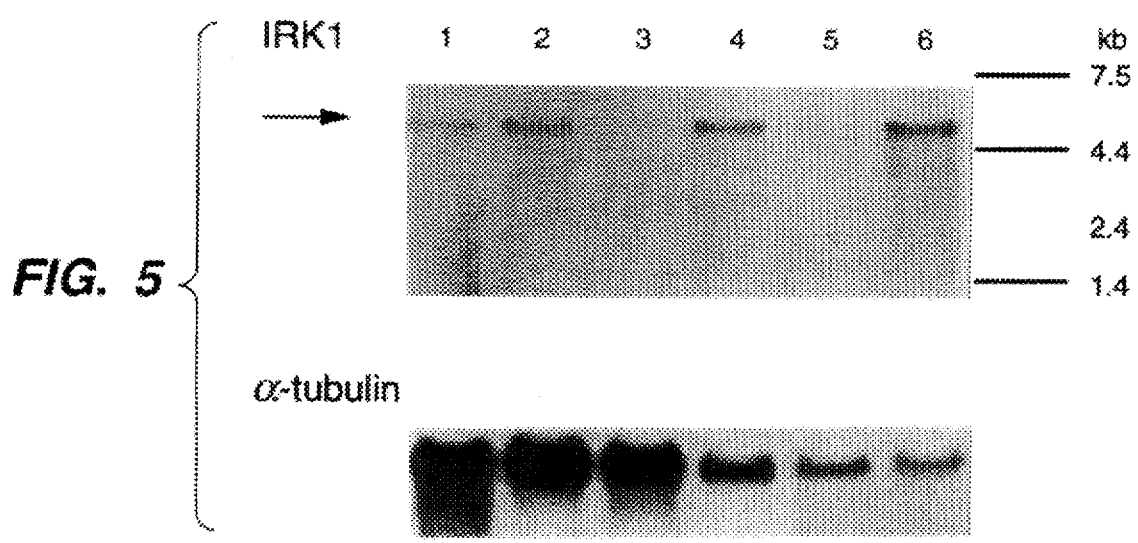
FIG. 5 depicts the distribution of IRK1 mRNA in mouse tissues (upper panel) and the presence of α-tublin in the same samples as a control for the integrity of the RNA (lower panel).

The expression of IRK1 mRNA in various tissues of the mouse was examined by Northern blot analysis (FIG. 5, upper panel). A 5.5 Kb mRNA for IRK1 was detected in J774 cells, forebrain, cerebellum, heart and skeletal muscle, but not in kidney. The abundance of this 5.5 Kb mRNA was much higher in skeletal muscle, heart and forebrain than in cerebellum.

The Northern blot analysis shown in FIG. 5 was performed as follows. Poly A$^+$ RNA was isolated using a Fast Track RNA isolation kit (Invitrogen) from J774 cells or tissues of 10 week old male Balb/c mice, from which the J774 cell line was established. RNA sample concentrations were determined by absorbance at 260 nm and 3 µg poly A$^+$ RNA was fractionated on 0.7% agarose-formaldehyde gel and transferred to a nylon membrane. A 3.7 Kb BstX1-Not1 fragment from the 3' end of IRK1 (SEQ ID NO:2) was labeled with $^{32}$P by random priming (Feinberg, A. B. and Vogelstein, B. (1983) Anal. Biochem. 132:6 and Addendum (1984) ibid., 137:266). Hybridizations were performed as described (Baldwin, T. J. et al. (1991), supra). Filters were washed with 0.1× SSC, 1.0% SDS at 65° C. for 15 min and autoradiographed. A RNA size marker (BRL) was probed separately with $^{32}$P labeled lambda DNA.

The lanes shown in FIG. 5 represent poly A$^+$ RNA from J774 cells (1), mouse forebrain (2), cerebellum (3), heart (4), kidney (5) and leg skeletal muscle (6). Forebrain includes cerebral cortex, hippocampus, basal ganglia, thalamus, hypothalamus and olfactory posit The positions of RNA size markers are shown on the right of the blot. A major band of 5.5 Kb RNA hybridizing to the IRK1 cDNA (SEQ ID NO:1) is indicated with an arrow.

To control for the integrity of RNA, the same blot was reprobed with a probe for α-tubulin (FIG. 5, lower panel). The α-tubulin probe hybridized to a 1.6 kb RNA.

5. Proposed Membrane Topology of the IRK1 Inward Rectifier K$^+$ Channel

By analogy with the proposed membrane topology of voltage-gated K$^+$ channels, the M1 and M2 segments of the IRK1 channel are proposed to be membrane-spanning and the H5 sequence in between extends from the extracellular surface into the membrane. A similar membrane topology has been proposed for the ATP-regulated K$^+$ channel (Ho, K. et al. (1993) Nature 362:31). Compared with the voltage-gated K$^+$ channel, which may contain an outer shell of S1, S2 and S3 segments in contact with the lipid environment (Tempel, B. et al. (1988) Nature 322:837), the inward rectifier K+ channel represents a more reduced structure corresponding to the inner core of the voltage-gated K$^+$ channel.

6. Cloning of a Rat G Protein Coupled Muscarinic Potassium Channel

Because the muscarinic K$^+$ channel is expressed in the heart and shows inward rectification properties similar to those of the inward rectifier K$^+$ channels encoded by ROMK1 (SEQ ID NO:5) and IRK1 (SEQ ID NO:2), a publicly available rat heart cDNA library (Roberds, S. L. and Tamkun, M. M. (1991) Proc. Natl. Acad. Sci. USA 88:1798) was screened to identify clones having homology to these two cDNA clones. Two degenerative primers were designed using the published amino acid sequences KDGRCNVQ (IRK1 amino acids 50–57) (SEQ ID NO:2) and VFQSIVG (IRK1 amino acids 162–168) (SEQ ID NO:2). The sequences of the primers are AA(A or G)GAIGGICGITG(C or T)AA(C or T)(C or A)T (SEQ ID NO:24) and ICCIACIATIGA(T or C)TG(G or A)AAIA (SEQ ID NO:25). PCR and screening of the cDNA library was carried out as described (Baldwin, T. J. et al. (1991) Neuron 7:471). Briefly, total poly A$^+$ RNA was isolated from either rat heart or rat brain as described supra. 2 µg poly A$^+$ RNA was copied into first strand cDNA using oligo(dT) priming and reverse transcriptase. The degenerate primers listed above (SEQ ID NO:24 and 25) were used to amplify the first-strand cDNA from either rat heart or brain. The PCR conditions were 94° C. for 30s, 50° C. for 30s and 72° C. for 90s for 40 cycles; AmpliTaq DNA polymerase (Perkin Elmer Cetus) was used. The resulting PCR products were run on an agarose gel and fragments approximately 350 bp in size were isolated. These fragments were cloned into the SmaI site of Bluescript SK+ (Stratagene) for sequence analysis. Identical PCR products were isolated from the heart and brain. These cloned PCR fragments were then used to screen the rat heart cDNA library to isolate the corresponding full length cDNAs.

The rat heart cDNA library was screened using standard hybridization techniques. The hybridization conditions were 50% formamide, 5× SSC, 1× Denhardt's solution, 20 mM sodium phosphate (pH 7.0), 1% SDS, 100 µg/ml salmon sperm DNA at 42° C. for 16 hours. The filters were washed in 0.1× SSC, 0.1% SDS at 65° C.

A 4.2 kb clone, named GIRK1(SEQ ID NO:3), was isolated and found to encode a protein that is structurally similar to the proteins encoded by ROMK1 (SEQ ID NO:5) and IRK1(SEQ ID NO:2).

The nucleotide sequence of GIRK1 (SEQ ID NO:3) was determined by the chain termination method using Sequenase (U.S. Biological Corp.) The nucleotide sequence of GIRK1 (SEQ ID NO:3) is shown in FIGS. 7a(1)–(2). Nucleotide A of the first methionine codon (ATG) is assigned as position +1. Only part of the 3' untranslated sequence is shown. The GIRK1 clone (SEQ ID NO:3) comprises approximately 4.2 kilobase pairs. There is a single long open reading frame which predicts a protein of 501 amino acids (SEQ ID NO:4).

The deduced amino acid sequence of GIRK1 (SEQ ID NO:4) is shown above the coding strand of the GIRK1 (SEQ ID NO:3) cDNA in FIGS. 7a(1)–(2). Although the first methionine in the GIRK1 cDNA sequence (SEQ ID NO:3) is at a position corresponding to the first methionine of ROMK1 (SEQ ID NO:5) and IRK1(SEQ ID NO:2), no stop codons are present in the same reading frame in the nucleotide sequence (SEQ ID NO:3) upstream of this methionine codon. This raised the possibility that additional amino acid sequences might exist at the amino terminus of GIRK1. To address this question, five independent cDNA clones from one heart and two brain cDNA libraries and more than 20 RACE PCR (rapid amplification of cDNA ends polymerase chain reaction, Frohman, M. A. (1990) PCR Protocols, Academic Press, San Diego, pp.28–38) products generated using two different reverse transcriptases (Invitrogen and Gibco BRL) were analyzed. This analysis resulted in an extension of only 19 bases (5' CCTTATTGGTGCTG-GTTTG 3') (SEQ ID NO:26) at the 5' end of the GIRK1 cDNA (SEQ ID NO:3). Nonetheless, when the GIRK1 cDNA (SEQ ID NO:3) is injected into Xenopus oocytes, functional K$^+$ channels are produced which have electrophysiological properties that closely resemble those of the G protein coupled muscarinic K$^+$ channel from the heart (Shown in FIGS. 8a–8g and discussed infra).

Further support for the assignment of the first methionine shown in FIG. 7a(1) (SEQ ID NO:3) as the start of the coding region was obtained by the isolation of a hamster GIRK1 cDNA clone (SEQ ID NO:3) from a cDNA library made with RNA isolated from a publicly available hamster HIT cell line (German, M. S. et al. (1991) Mol. Endocrinol. 5:292). This hamster cDNA contains additional sequences upstream of the first methionine shown in FIG. 7a(1) (SEQ ID NO:3). Multiple stop codons are present about 230 bp upstream of the methionine at position +1 and no other methionine codons appear in this region. This data confirms that the entire protein coding sequence is present on the GIRK1 clone (SEQ ID NO:3) shown in FIGS. 7a(1)–(2).

The proposed transmembrane segments M1 and M2 are boxed. Also boxed is a segment with sequence similarity to the H5 region of voltage-gated $K^+$ channels. There are 9 potential protein kinase C phosphorylation sites (Thr64, Ser203, Ser284, Ser357, Ser396, Thr407, Ser424, Thr455 and Ser497).

FIG. 7b shows an alignment of the amino acid sequences from GIRK1, (SEQ ID NO:4) the G protein coupled muscarinic $K^+$ channel, IRK1(SEQ ID NO:2), the inward rectifier $K^+$ channel and ROMK1 (SEQ ID NO:5), the ATP-regulated $K^+$ channel. For IRK1(SEQ ID NO:2) (SEQ ID NO:5) and ROMK1, only the amino acid sequences which differ from GIRK1 (SEQ ID NO:4) are given in single letter code. (:) indicates amino acids that are identical to those in GIRK1(SEQ ID NO:4). (–) indicates gaps introduced into the sequence to improve alignment. The proposed transmembrane regions M1 and M2 and the H5-like segment are boxed. GIRK1 (SEQ ID NO:4) shares 43% identity with IRK1 (SEQ ID NO:2) and 39% identity with ROMK1 (SEQ ID NO:5) over the total amino acid sequence.

7. The GIRK1 cDNA (SEQ ID NO:3) cDNA Directs the Synthesis of a $K^+$ Channel

FIGS. 8a–8g shows that the GIRK1 (SEQ ID NO:3) cDNA encodes a functional $K^+$ channel which has electrophysiological properties which closely resemble those of G protein coupled muscarinic $K^+$ channels from the heart. Inwardly rectifying $K^+$ currents recorded by two electrode voltage clamp from Xenopus oocytes injected with GIRK1 cRNA are shown in FIG. 8a–8g.

Oocytes were injected with 50 nl of cRNA solution, which contains approximately 300 ng/ml GIRK1 cRNA and 300 ng/ml m2 muscarinic receptor cRNA (FIG. 8a and 8b), or either, or both 500 ng/ml GIRK1 cRNA and 15 ng/ml each of $G\alpha_{i2}$, $\beta_1$ and $\gamma_2$ cRNA (FIG. 8c, 8d, 8e, 8f and 8g). Eletrophysiological recordings were carried out 48–96 hours later at 22°–25° C. using the two electrode voltage clamp technique (Baldwin, T. J. et al. (1991) Neuron 7:471). Data acquisition and analysis were done on an 80386-based microcomputer using the p-Clamp program and a TL-1 A/D converter (Axon Instruments). Microelectrodes were filled with 3M KCl and the resistances were 0.7–1.5 M ohm. The bath solution contained 90 mM KCl, 3 mM $MgCl_2$, 5 mM Hepes (pH7.4) (the 90 mM $K^+$ solution). In solutions with reduced $K^+$ concentration, $K^+$ was replaced with N-methylglucamine.

As is the case with the muscarinic $K^+$ channel in the heart, the GIRK1 channel could be activated by muscarinic receptor activation. FIG. 8a shows current traces recorded in 90 mM $K^+$ solution from oocytes injected with m2 muscarinic receptor and GIRK1 cRNA before and after application of 1 µM carbachol. The carbachol-induced currents are the difference of the former two sets of traces. The holding potential was 0 mV, and current traces elicited by steps to +50, +20, –10, –40, –70, –100 and –130 mV are shown. The amplitude of carbachol-induced current at –150 mV ranged from 290–760 nA (n=8).

Figure 8G:
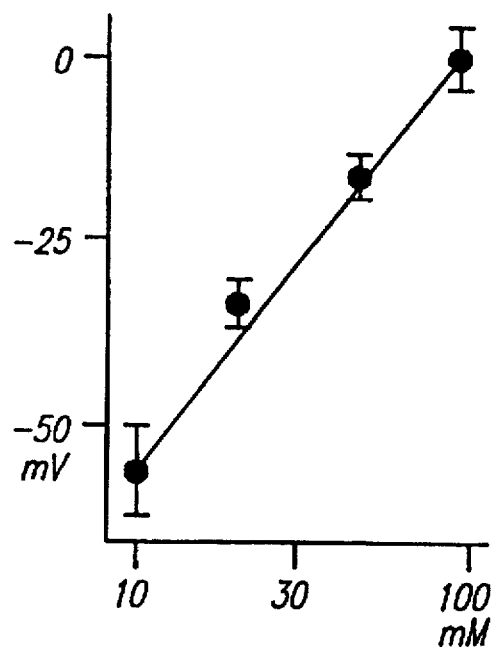
FIG. 8g depicts a logarithmic plot of extracellular $K^+$ concentration versus activation potential.
Figure 8B:
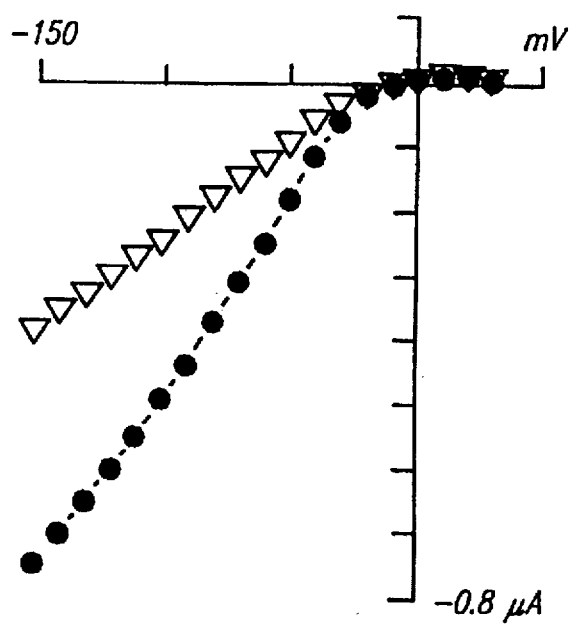

FIG. 8b depicts the current-voltage (I–V) plot of the carbachol-induced current traces shown in FIG. 8a. Current amplitude at the beginning (▽) and at the end (●) of the steps were plotted. Following co-injection of m2 muscarinic receptor cRNA (Bonner, T. I. et al. (1987) Science 237:527) and GIRK1 cRNA, bath application of 1 µM carbachol induced an inwardly rectifying current (FIG. 8a and 8b). The time course of the induced currents, obtained by subtracting the currents before from those after bath application of carbachol, showed slow activation at the beginning of voltage pulses (FIG. 8a and 8b), a characteristic property of muscarinic $K^+$ channels (Sakmann, B. et al. (1983) Nature 303:250). This carbachol-induced inwardly rectifying current was not observed when either the m2 muscarinic receptor (n=4) or GIRK1 (n=4) cRNA alone was injected. As the m2 muscarinic receptor is known to activate G proteins (Gilman, A. G. (1984) Cell 36:577), the activation of GIRK1 channel was most likely mediated by endogenous oocyte G proteins (Dascal, N. (1987) Crit. Rev. Biochem. 22:317) that were coupled with the m2 receptor.

Because the identity of the endogenous G proteins that coupled m2 muscarinic receptors to GIRK1 channels could not be readily determined, the effect of an exogenously introduced G protein trimer composed of $\alpha_{i2}$ (Jones, D. T. and Reed, R. R. (1987) J. Biol. Chem. 262:14241), $\beta_1$ (Fong, H. K. W. et al. (1986) Proc. Natl. Acad. Sci. USA 83:2162) and $\gamma_2$ (Gautman, N. et al. (1989) Science 244:971) subunits, on the GIRK1 channel was investigated.

Figure 8D:
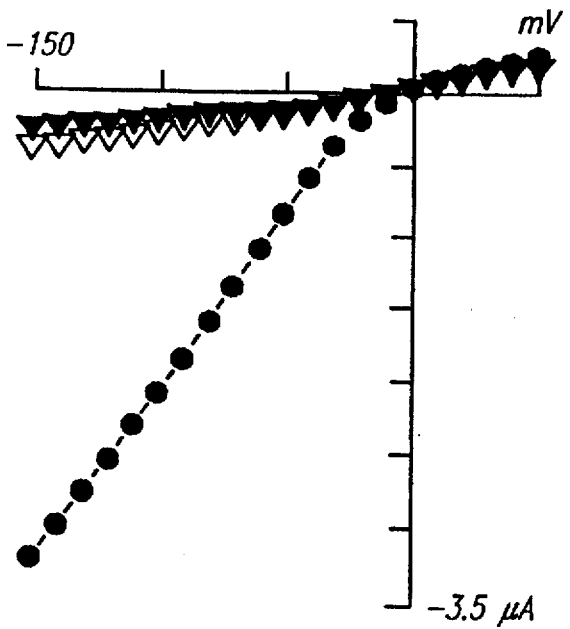
FIG. 8d depicts a I–V plot of the data shown in FIG. 8c.
Figure 8C:
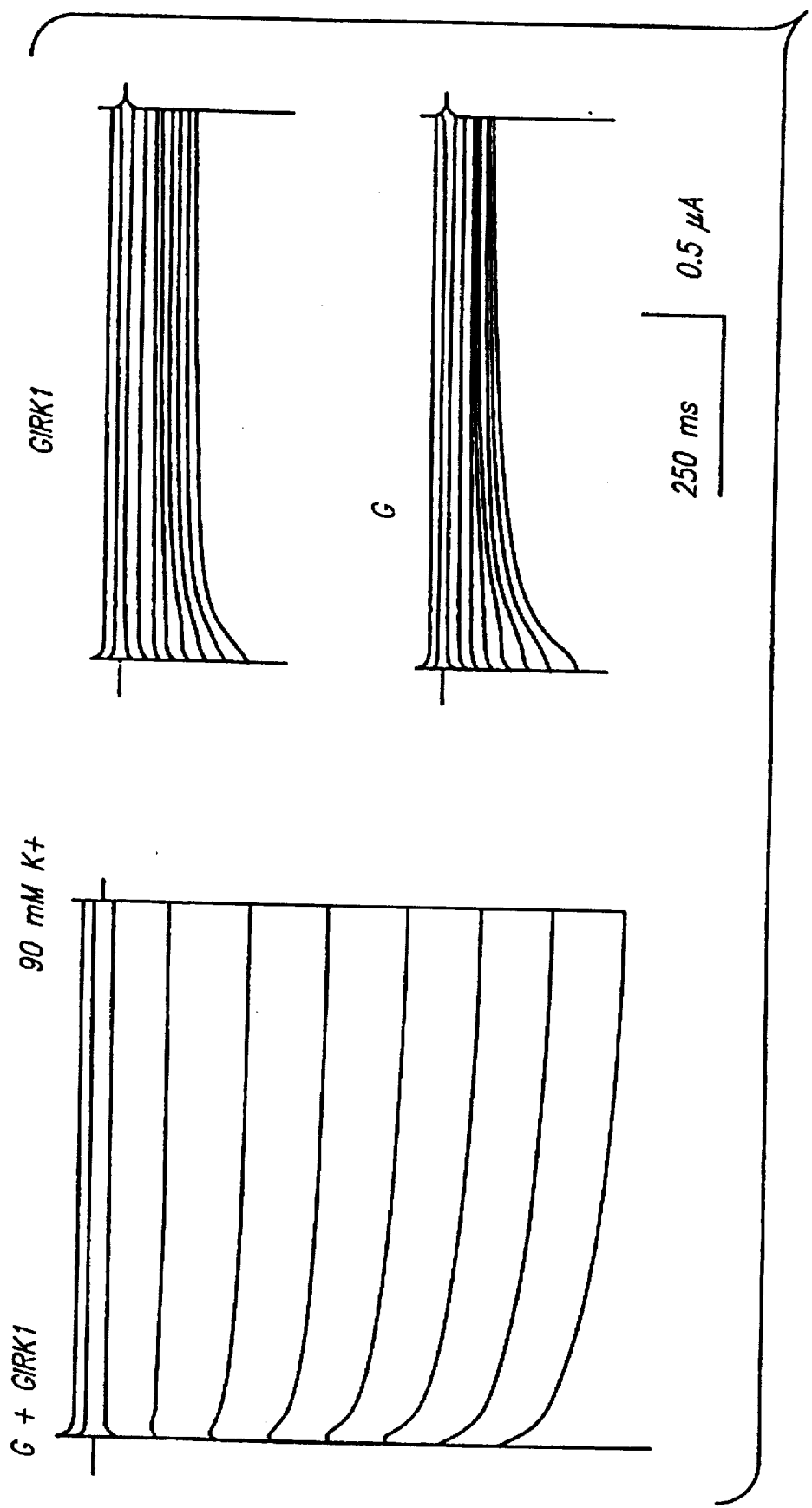
FIG. 8c depicts current traces from oocytes injected with both GIRK1 and $G\alpha_{i2}$, $\beta_1$, $\gamma_2$ cDNA, or with either GIRK1 or $G\alpha_{i2}$, $\beta_1$, $\gamma_2$ cDNA alone.

Previous studies suggested that muscarinic $K^+$ channels are coupled with $G\alpha_i$ (Yanti, A. et al. (1987) Science 235:207, Yanti, A. et al. (1988) Nature 336:680, and Brown, A. M. and Birnbaumer, L. (1990) Annu. Rev. Physiol. 52:197) and/or $\beta_\gamma$ subunits (Logothetis, D. E. et al. (1987) Nature 325:321 and Kurachi, Y. et al. (1992) Progress in Neurobiol. 39:229), and that a basal level of muscarinic $K^+$ channel activation can be observed without activating muscarinic receptors in the atrial cell (Ito, H. et al (1991) J. Gen. Physiol. 98:517). When cRNA for m2 receptor, $G\alpha_{i2}$, $\beta_1$, $\gamma_2$ and GIRK1 were coinjected into oocytes, an inwardly rectifying current, similar to the carbachol-induced current, was observed without activating the m2 muscarinic receptor. Activation of m2 receptor did not significantly increase this current. The large basal activity and the lack of coupling between the exogenously introduced muscarinic receptors and $G\alpha_{i2}$, $\beta_1$, $\gamma_2$ might be explained by the inappropriate combination or ratio of the injected G protein subunits in a heterologous expression system. The inwardly rectifying current was also observed in oocytes injected with $G\alpha_{i2}$, $\beta_1$, $\gamma_2$ and GIRK1 cRNA, but not with either $G\alpha_{i2}$, $\beta_1$, $\gamma_2$ or GIRK1 cRNA alone (FIGS. 8c & 8d). These results suggest that GIRK1 channels are activated by exogenously introduced G protein subunits.

FIG. 8c shows current traces recorded in 90 mM $K^+$ solution from oocytes injected with both GIRK1 and $G\alpha_{i2}$, $\beta_1$, $\gamma_2$ cRNA or with either GIRK1 or $G\alpha_{i2}$, $\beta_1$, $\gamma_2$ cRNA alone. The holding potential and the depolarization steps are as in FIG. 8a. The amplitude of the GIRK1 current at –150 mV after linear-leak subtraction ranged from 600–2700 nA (n=35).

FIG. 8d depicts the I–V plot of the current traces as shown in FIG. 8c. Current amplitude at the end of the steps were plotted. Symbols are (●) both GIRK1 and $G\alpha_{i2}$, $\beta_1$, $\gamma_2$ cRNA, (▽) only GIRK1 cRNA and (▼) only $G\alpha_{i2}$, $\gamma_2$ cRNA.

As expected for a $K^+$ selective inwardly rectifying channel (Sakmann, B. et al. (1983) Nature 303:250), the activation potential of GIRK1 channel (see FIG. 8g) shifted to hyperpolarized potential upon reduction of extracellular $K^+$ concentration (FIGS. 8e and 8f) and the amount of shift follows the change in the $K^+$ equilibrium potential ($E_K$) as predicted by the Nernst equation (FIG. 8g).

Figure 8E:
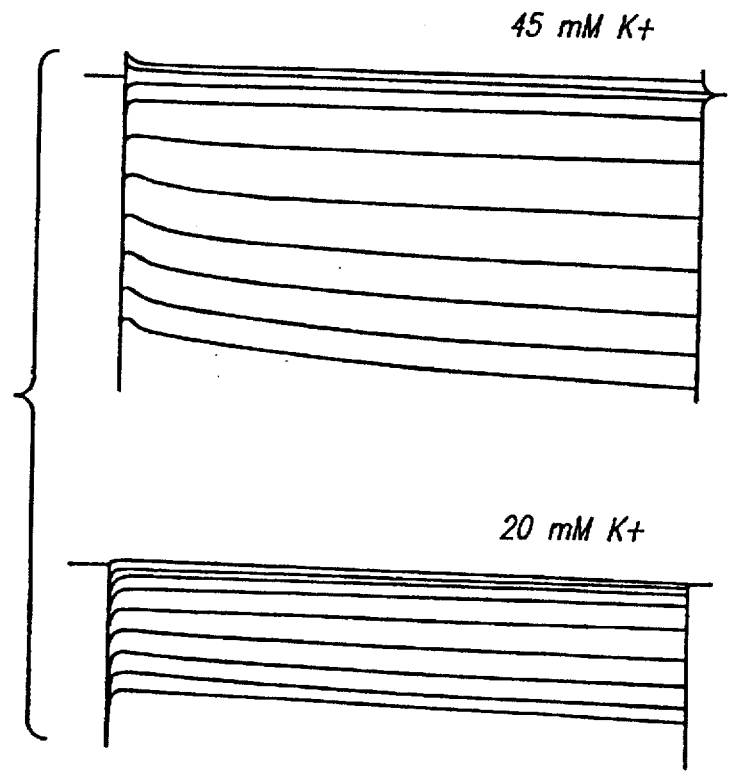
FIG. 8e depicts current traces recorded in 45 mM or 20 mM $K^+$ solution from the same oocytes injected with both GIRK1 and $G\alpha_{i2}$, $\beta_1$, $\gamma_2$ cDNA as in FIG. 8c.

FIG. 8e shows the current traces recorded in 45 mM $K^+$ or 20 mM $K^+$ solution from the same oocytes injected with both GIRK1 and $G\alpha_{i2}$, $\beta_1$, $\gamma_2$ cRNA as in (FIG. 8c, left panel). The holding potential and the depolarization steps are as in FIG. 8a.

Figure 8F:
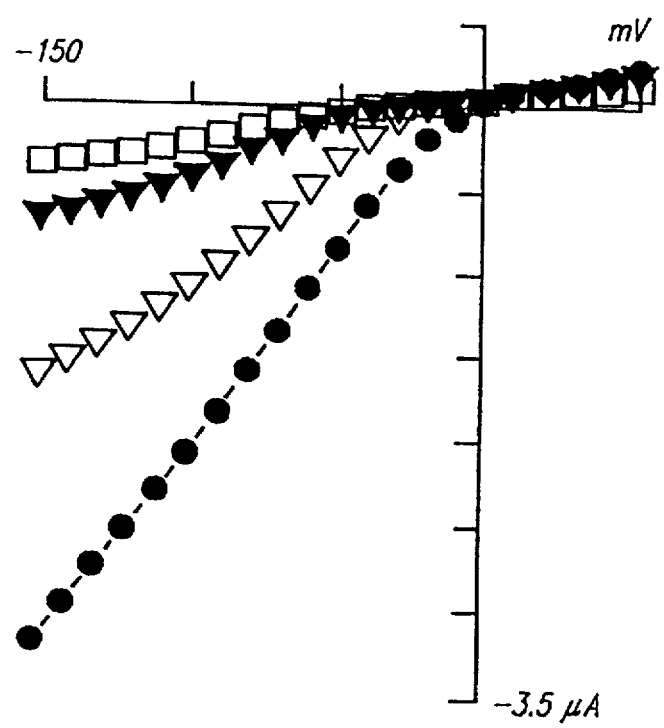
FIG. 8f depicts a I–V plot of the inwardly rectifying current from oocytes injected with GIRK1 and $G\alpha_{i2}$, $\beta_1$, $\gamma_2$ cDNA in various external $K^+$ concentrations.

FIG. 8f depicts the I–V plot of the inwardly rectifying current from oocytes injected with GIRK1 and $G\alpha_{i2}$, $\beta_1$, $\gamma_2$ in various external K$^+$ concentration. Symbols are (●):90 mM K$^+$, (▽): 45 mM K$^+$, (▼) 20 mM K$^+$ and (□) 10 mM K$^+$. Current amplitude at the end of the steps were plotted. $E_K$'s in these solutions predicted by the Nernst equation were 0 mV (90 mM K$^+$), −17 mV (45 mM K$^+$), −37 mV (20 mM K$^+$), and −55 mV (10 mM K$^+$). (The intracellular K$^+$ concentration of oocytes was assumed to be 90 mM). The small outward currents in (FIGS. 8c–f) include some endogenous currents of the oocyte.

FIG. 8g depicts a logarithmic plot of extracellular K$^+$ concentration versus activation potential (the potential where the slope of current-voltage relation starts to increase). Vertical bars show standard deviation. The mean and standard deviation values are 0±4 (n=9; 90 mM), −16±3 (n=5; 45 mM), −33±3 (n=7; 20 mM) and −56±6 (n=2; 10 mM). The straight line shows the equilibrium potential of K$^+$ predicted by the Nernst equation.

8. The GIRK1 Channel is Activated by GTP$_\gamma$S

To test whether the activation of GIRK1 is caused by direct interaction with G proteins, the effect of the non-hydrolyzable GTP analogue, GTP$_\gamma$S, applied to the cytoplasmic side of excised patches was examined.

In FIGS. 9a–9e, oocytes were injected with 50 nl of cRNA, which contains about 300 ng/ml GIRK1 channel cRNA, 300 ng/ml m2 muscarinic receptor cRNA, and 10 ng/ml each of $G\alpha_{i2}$, $\beta_1$, $\gamma_2$ cRNA, or 500 ng/ml GIRK1 channel cRNA and 15 ng/ml each of $G\alpha_{i2}$, $\beta_1$, $\gamma_2$ cRNA. The channel activities were observed in the absence of carbachol; similar results have been obtained from oocytes injected with GIRK1 and $G\alpha_{i2}$, $\beta_1$, $\gamma_2$ cRNA, with or without m2 receptor cRNA. Single channel activity was recorded in cell-attached or inside-out patches. Currents were recorded with a List EPC7 amplifier at 22°–25° C. The continuous recordings were stored on VCR, transferred to disc at 2–8 kHz through an A/D converter (Instrutech), digitally filtered at 0.5–2 kHz and analyzed by FETCHAN program. Patch pipettes had resistances of 1–4M ohm. The pipette solution (external) was 75 mM K$_2$SO$_4$, 15 mM KCl, 2 mM MgSO$_4$, 10 μM GdCl$_3$, 5 mM KOH and 10 mM Hepes (pH 7.4). GdCl$_3$ was included to suppress stretch channel activity (Yang, X.-C. and Sachs, F. (1989) Science 243:1068). GdCl$_3$ was found to have little effect on the GIRK1 current recorded by two electrode voltage clamp. The Mg$^{2+}$-containing bath solution (internal) was 72.5 mM K$_2$SO$_4$, 15 mM KCl, 4.4 mM MgSO$_4$, 2.5 mM K$_2$ATP, 5 mM KOH, 5 mM Hepes (pH7.2). Total K$^+$ concentration was 170 mM, and free Mg$^{2+}$ concentration was calculated to be 2.5 mM. The Mg$^{2+}$-free bath solution (internal) was 59 mM K$_2$SO$_4$, 15 mM KCl, 10 mM K$_2$EDTA, 12 mM KOH, 2.5 mM K$_2$ATP, 5 mM Hepes (pH 7.2). For both bath solutions, a high concentration of ATP (2.5 mM) was used to suppress ATP sensitive channels (Ashcroft, S. J. H. and Ashcroft, F. M. (1990) Cellular Signalling 2:197). In the cell attached mode, the membrane potential of the patch differs from the applied potential (the potential difference between the pipette solution and the bath solution, each containing 170 mM K$^+$) by an amount equivalent to the resting potential of the oocyte which is close to $E_K$. Under this condition the applied potential is approximately the K$^+$ driving force across the patch membrane in both the cell-attached mode and the inside-out excised patch mode, so that the same channel is expected to exhibit the same single channel current before and after excision of the membrane patch.

In cell-attached recordings from oocytes injected with GIRK1 and $G\alpha_{i2}$, $\beta_1$, $\gamma_2$ cRNA, single-channel openings were observed in the absence of activated m2 receptor, as was found for the recordings under two electrode voltage-clamp. The single-channel activity decreased after excising the membrane patch into a solution containing no GTP, but could be restored by applying 100 GTP$_\gamma$S to the cytoplasmic side of the membrane (FIG. 9a).

FIG. 9a shows one minute segments of continuous recordings from a membrane patch initially in cell-attached configuration (left panel), subsequently excised (inside-out) into solution without GTP (middle panel), and then exposed to 100 μM GTP$_\gamma$S (right panel). Expanded traces from the small segments indicated by triangles are shown below. The holding potential was −60 mV. Open time histograms were fitted by least squares with three exponentials. The mean and standard deviation (n=4) of the three time constants and percentage contributions were (cell attached) 0.26±0.11 ms (21±8%), 1.2±0.3 ms (43±9%) and 7.2±1.0 ms (36±10%); excised plus GTP$_\gamma$S, 0.45±0.35 ms (25+13%), 2.3±0.9 ms (50±11%) and 8.9±4.3 ms (25±13%). The time constant of the muscarinic K$^+$ channel was reported to be 0.96 ms (Ito, H. et al. (1992) J. Gen. Physiol. 99:961)–1.4 ms (Sakmann, B. et al. (1993) nature 303:250).

In five patches, the normalized open probability ($P_o$) decreased by 6 fold after excising into GTP free solution, and increased by 10 fold after applying GTP$_\gamma$S (FIG. 9b). FIG. 9b shows the open probability measured from continuous single channel recordings during cell-attached, excised and GTP$_\gamma$S applied periods. Because the number of channels in the patch was not known, the open probability was normalized to the $P_o$ measured in cell-attached patches. The error bars show standard deviation. The normalized $P_o$ (n=5) was 0.18 ±0.18 after excising and 1.78±0.76 with GTP$_\gamma$S (mean±standard deviation). The decrease upon excision and the increase following exposure to GTP$_\gamma$S were significant by Students' paired t-test (p<0.05).

The channel activities recorded in the cell-attached configuration and those recorded in the presence of cytoplasmic GTP$_\gamma$S appeared to come from the same channel, because the single channel conductance (42 pS) and the kinetics were similar in these two conditions (see FIG. 9a). These results imply that the activation of GIRK1 is caused by an interaction with G proteins that are associated with the patch of membrane, rather than diffusible second messengers that are activated by G proteins.

9. The GIRK1 Channel is the Muscarinic K$^+$ Channel

To see if the expressed GIRK1 channel is similar to the muscarinic K$^+$ channel in the heart (Sakmann, B. et al., supra and Horie, M. and Irisawa, H. (1991) J. Physiol. 408:313) we measured the single channel conductance and the open time and examined if the inward rectification of GIRK1 channel depended on internal Mg$^{2+}$, as has been shown for the muscarinic K$^+$ channel (Horie, M. and Irisawa, H., supra).

GIRK1 showed a single channel conductance of 42 pS in 170 mM K$^+$ (FIGS. 9c & 9e), as compared to 41 pS in 150 mM K$^+$ for the muscarinic K$^+$ channel (Horie, M. and Irisawa, H., supra). The open time distribution was similar to that reported for the muscarinic K$^+$ channel. Finally, GIRK1 channels activated by GTP$_\gamma$S showed strong inward rectification which depended on the presence of internal Mg$^{2+}$; when Mg$^{2+}$ was removed from the bath solution, outward currents were recorded from the inside-out patches (FIGS. 9d and 9e). All of the single channel recordings were obtained in the presence of 2.5 mM cytoplasmic ATP which blocks ATP-sensitive K$^+$ channels. Taken together, these results show that the GIRK1 channel corresponds to the muscarinic K$^+$ channel.

FIG. 9c shows the recording of single channel activity in the presence of cytoplasmic Mg$^{2+}$. The single channel conductance was 42±1 pS (n=5). Free $Mg^{2+}$ concentration in the cytoplasmic solution was calculated to be 2.5 mM.

FIG. 9d shows recordings in $Mg^{2+}$-free cytoplasmic solution. Only outward channel events are shown. The inward single channel conductance was 43±2 pS (n=2) in $Mg^{2+}$-free solution.

FIG. 9e depicts I–V plots of single channel current from the experiment shown in FIG. 9c: (●) and FIG. 9d: (○). Straight lines show the best fit having a slope conductance of 42 pS for $Mg^{2+}$ and 43 pS for $Mg^{2+}$-free solution. The deviation of the outward current amplitude in $Mg^{2+}$-free solution from ohmic conductance (dashed line) could be due to residual $Mg^{2+}$, which remains near the excised patch of membrane even after perfusing the bath with $Mg^{2+}$-free solution.

10. Distribution of GIRK1 mRNA in Various Tissues.

The expression of GIRK1 mRNA was examined by Northern blot analysis. $Poly(A)^+$ RNA was isolated from tissues of 12 week old rats and 6 week old guinea pigs using the Fast Track RNA isolation kit (Invitrogen). The concentration of the $poly(A)^+$ RNA samples were determined by absorbance at 260 nm. 3 μg $poly(A)^+$ RNA was fractionated on a 0.7% agarose-formaldehyde gel and transferred to a nylon membrane.

Figures 10A, 10B:
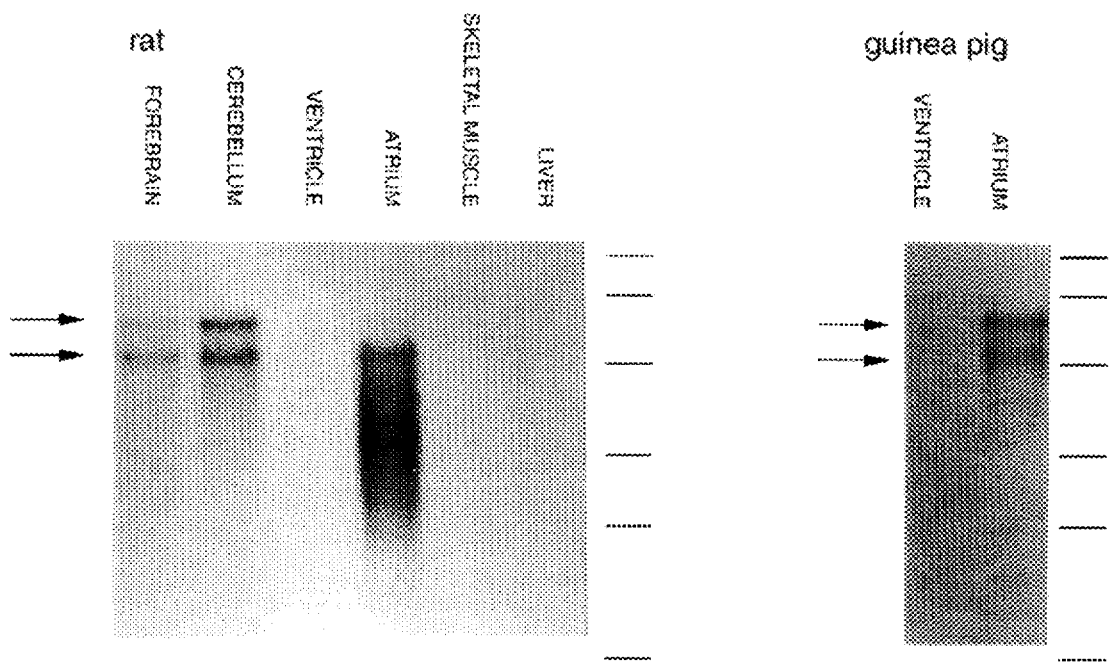
FIG. 10a shows the distribution of GIRK1 mRNA in rat tissue.
FIG. 10b shows the distribution of GIRK1 mRNA in guinea pig tissue.

In FIGS. 10a and 10b, the lanes represent poly $A^+$ RNA from rat forebrain, cerebellum, heart ventricle, atrium, skeletal muscle and liver (FIG. 10a), and from guinea pig heart ventricle and atrium (FIG. 10b). Forebrain includes cerebral cortex, hippocampus, basal ganglia, thalamus, hypothalamus and olfactory bulb. The atrium preparation includes part of the vessel stems.

The blots were probed with $^{32}$P-labelled GIRK1 cDNA (FIG. 10a) or a 363 bp PCR fragment, obtained from cDNAs reverse-transcribed from guinea-pig heart RNA, which encodes identical amino acids as those of residues 49 through 169 of GIRK1 (FIG. 10b). The probes were labeled using the random priming method (Fienberg and Vogelstein (1983) Annal. Biochem. 132:6 and addendum Annal. Biochem 137:266). Hybridizations were performed as described in FIG. 5.

Two major RNA species of approximately 4.5 and 6.0 Kb hybridized to the probes as indicated by the arrows. The positions of RNA size markers (9.5, 7.5, 4.4, 2.4, 1.4 and 0.2 Kb) are shown on the right of each blot as bars.

The integrity of the RNA samples was verified by ethidium bromide staining of the gel and by reprobing the same blot with a labeled cDNA for α-tubulin (1.6 Kb message, data not shown). These controls, however, do not rule out the possibility that the smear seen in the rat atrium lane (FIG. 10a) might be due to partial degradation of RNA; much less smearing was evident in the guinea-pig atrium lane (FIG. 10b).

FIGS. 10a and 10b show that GIRK1 mRNA (approximately 4.5 Kb and 6.0 Kb) is more abundant in the heart atrium than in the ventricle (FIG. 10a depicts RNA isolated from rat tissues and FIG. 10b depicts RNA isolated from guinea pig tissues). This finding is consistent with the distribution of the muscarinic $K^+$ channels determined by electrophysiological studies (Sakmann, B. et al., supra, Breitwieser, G. E. and Szabo, G. (1985) Nature 317:538 and Yatani, A. et al., Science, supra).

GIRK1 mRNA was also detected in forebrain and cerebellum, but not in liver or skeletal muscle in rats (FIG. 10a). G protein coupled $K^+$ channels have been found in the brain (Vandongen, A. M. J. et al. (1988) Science 242:1433 and Brown, D. A. (1990) Annu. Rev. Physiol. 52:215) and they are activated by various neurotransmitters, such as substance P (Stanfield, P. R. et al. (1985) Nature 315:498), GABA (Gahwiler, B. H. and Brown, D. A. (1985) Proc. Natl. Acad. Sci. USA 82:1558 and Williams, J. T. et al. (1988) J. Neurosci. 8:3499), somatostatin (Mihara, S. et al. (1987) J. Physiol. 390:335 and Inoue, M. et al. (1987) J. Physiol. 407:177), opioid (North, R. A. et al. (1987) Proc. Natl. Acad. Sci. USA 4:5487 and Wimpey, T. L. and Chavkin, C. (1991) Neuron 6:281) and acetylicholine (Gerber, U. et al. (1991) J. Neurosci. 11:3861). Thus, GIRK1 channel may play a role in regulating the neuronal activity in the brain as well as the excitability of the heart.

The above examples show that the GIRK1 cDNA (SEQ ID NO:3), a new member of the inwardly rectifying $K^+$ channel superfamily, encodes the muscarinic $K^+$ channel in the heart. Like the muscarinic $K^+$ channel, the GIRK1 channel is abundant in the atrium and is likely to be activated directly by G proteins. Moreover, the single-channel conductance, kinetics and inward rectification properties are all similar to those of the muscarinic $K^+$ channel of the heart.

11. IRK1 and GIRK1 Channels are Expressed in Insulin Secreting Cells

To investigate whether the IRK1 or GIRK1 $K^+$ channel, or both, were expressed in insulin secreting cells, a cDNA library made with RNA isolated from the HIT-T15 cell line (ATCC CRL 1777) was screened using the IRK1 and GIRK1 sequences as probes. The HIT-T15 cell line is a Syrian hamster insulinoma cell line which was established from a primary culture of pancreatic islet cells which ere transformed with SV40 virus (Santerre, B. F. et al. (1981) Proc. Natl. Acad. Sci. USA 78:4339. This cell line is a β cell line and secretes insulin in response to glucose and glucagon stimulation.

A publicly available HIT-T15 cDNA library (German, M. S. et al. (1991) Mol. Endocrinol. 5:292) was screened as follows. Hybridizations were carried out under high stringency conditions as follows. Briefly, the IRK1 (SEQ ID NO:1) and GIRK1 (SEQ ID NO:3) cDNAs were labeled with $^{32}$P using the random priming method and hybridized to filters containing immobilized colonies. Hybridization conditions were as described in Example 6, supra.

cDNA clones corresponding to both GIRK1 (SEQ ID NO:3) and IRK1 (SEQ ID NO:1) were isolated from the HIT-T15 library. The identity of the cDNA contained in the colony which hybridized to the rat GIRK1 cDNA probe was confirmed by DNA sequencing and was found to be a bona fide hamster GIRK1 cDNA (SEQ ID NO:3).

The finding that both the IRK1 and GIRK1 channels are expressed in an insulin secreting cell supports the assertion that both of these inward rectifier $K^+$ channels play a role in insulin release from the β cells of the pancreas. Further bolstering this hypothesis is the fact that adrenaline is known to regulate insulin release (Rorsman, P. et al. (1991) Nature 349:77); this suggests that GIRK1, the G protein coupled $K^+$ channel is involved in insulin release.

While most attention has been focused on the role of the ATP-sensitive $K^+$ channel in insulin secretion, the above results suggest that the ATP-sensitive $K^+$ channel is not the only inward rectifier $K^+$ channel involved in insulin secretion.

The finding that the mouse IRK1 (SEQ ID NO:1) cDNA and the rat GIRK1 (SEQ ID NO:3) cDNA can be used to isolate corresponding hamster homologues supports the notion that this class of inward rectifier $K^+$ channels is conserved among the mammals. The present invention's isolation of first the mouse IRK1 gene (SEQ ID NO:1) and then the rat GIRK1 gene (SEQ ID NO:3) made possible a finding of conservation among this class of mammalian inward rectifier $K^+$ channels.

12. Materials Testing

After having identified the inward rectifier potassium channel expression products, IRK1 (SEQ ID NO:1) and GIRK1(SEQ ID NO:4), extrinsic materials may be assayed. The effect of materials on these $K^+$ channel products may preferably be monitored electrophysiologically, for example, by monitoring changes of inactivation properties, kinetics, inward rectification properties, alteration in single channel conductance, etc. The same procedures may be used to screen a battery of materials on the same expression product or on other cells containing either the IRK1 or GIRK1 channels. The selectivity of a material for a given channel may be determined by testing the effect of the material on other $K^+$ channel types. For example, a material can be tested using an expression system which expresses the IRK1 channel and the results compared to that seen in an expression system in which the GIRK1 channel is expressed. In addition, a number of other types of $K^+$ channels have been cloned including voltage-gated $K^+$ channels and ATP-regulated $K^+$ channels. Expression systems expressing these other $K^+$ channels may be used for comparison to select materials which have a selective effect on either, or both, the IRK1 and GIRK1 channels. Drugs that modulate the IRK1 or GIRK1 channels selectively are identified as candidates.

A particularly useful method of screening for materials capable of modulating the activity of the inward rectifier $K^+$ channel expression products, IRK1 and GIRK1 is enabled by the following observation. Oocytes injected with either the IRK1 cRNA or the GIRK1 and G protein cRNAs died when they were exposed to external concentrations of $K^+$ of 1–10 mM. Cell death or loss of cell viability was determined by measuring the membrane resistance of the injected oocyte. A membrane resistance below 0.2 mohms indicates loss of viability. The membrane resistance of a viable oocyte is approximately 1 mohm. Alternatively, loss of viability was determined visually as Xenopus oocytes lose their characteristic pigmentation in the animal pole upon cell death. Materials which block the activity of either the IRK1 or GIRK1 $K^+$ channels prevent cell death thereby enabling a rapid and easy method to screen materials for the ability to modulate these $K^+$ channels.

This method is practiced by injecting oocytes with either the IRK1 cRNA or the GIRK1 and G protein cRNAs as described supra with the exception that the external bath in which the injected oocytes are placed contains 1–10 mM $K^+$ rather than 50–150 mM $K^+$. As discussed supra, isotonic $K^+$ for oocytes is approximately 90 mM K+. Injected oocytes are typically suspended in solutions containing 50–150 mM $K^+$, most preferably 90–100 mM $K^+$ except when one is practicing the above described screening method. A suitable control is always run in parallel with oocytes injected with either the IRK1 cRNA or the GIRK1 and G protein cRNAs to control for variations in viability between different batches of uninjected oocytes. Suitable controls include oocytes injected with water or with cRNA encoding another $K^+$ channel such as a voltage-gated $K^+$ channel.

Additionally, the above screening method may also be practiced using vertebrate or invertebrate cells transfected with DNA encoding the IRK1 gene (SEQ ID NO:1). The transfected cells which express the IRK1 channel are exposed to culture medium containing 1–10 mM $K^+$. Materials are screened for the ability to prevent cell death. Cell death is detected by the failure of the cultured cells to divide.

13. Drug Testing in Disease

Materials comprising drugs identified by the assays described supra as being candidates selective for either the IRK1 or GIRK1 $K^+$ channels may be tested in vivo for efficacy in appropriate animal models, for example, for their ability to regulate the heart beat in that animal or to control the release of insulin. The route of administration of the drugs can be oral, parental, or via the rectum, and the drug could be administered alone as principals, or in combination with other drugs, and at regular intervals or as a single bolus, or as a continuous infusion in standard pharmaceutical formulations. Drugs described supra are also tested in in vitro assays for their ability to modulate the activity of physiologic functions mediated by the IRK1 or GIRK1 $K^+$ channels.

14. A Treatment Protocol

Materials identified as a candidate by the assays described above are tested for safety in humans as per Federal guidelines. These candidates described supra are administered via standard pharmaceutical formulations to patients with diseases, again either orally, parenterally, rectally, alone or in combination, at regular intervals or as a single bolus, or as a continuous infusion, for modulating IRK1 or GIRK1 $K^+$ channels in cells, thus impacting physiological functions regulated by the activity of these channels.

Notwithstanding that reference has been made to particular preferred embodiments, it will be further understood that the present invention is not to be construed as limited to such, rather to the lawful scope of the appended claims.

---

We claim:

1. An isolated nucleic acid encoding a mammalian inward-rectifying potassium channel protein, having a nucleotide sequence selected from the group consisting of:
    (a) the sequence of a cDNA molecule isolated from a mammalian library, wherein the complementary strand of said cDNA molecule hybridizes under conditions of low stringency with a DNA molecule having a sequence identical to the IRK1 coding sequence shown in SEQ ID NO: 3, and
    (b) a sequence degenerate with the sequence of (a).

2. A nucleic acid according to claim 1, wherein said potassium channel protein has an amino acid sequence which is at least about 70% homologous with the amino acid sequence of the IRK1 gene product (SEQ ID NO:2).

3. A nucleic acid according to claim 1, wherein said potassium channel protein has an amino acid sequence which is at least about 80% homologous with the amino acid sequence of the IRK1 gene product (SEQ ID NO:2).

4. A nucleic acid according to claim 1, wherein said potassium channel protein has an amino acid sequence which is at least about 90% homologous with the amino acid sequence of the IRK1 gene product (SEQ ID NO:2).

5. A nucleic acid according to claim 1, wherein said potassium channel protein has the amino acid sequence of the IRK1 gene product (SEQ ID NO:2).

6. A vector comprising a nucleic acid according to claim 1.

7. A host cell transformed or transfected with a nucleic acid according to claim 1.

8. A screening assay for identifying materials which modulate the activity of a mammalian inward-rectifying potassium channel, comprising the steps of:
    (a) introducing a nucleic acid according to claim 1 into an expression system and causing the expression system to express the nucleic acid, whereby a potassium channel protein is produced;
    (b) contacting said potassium channel protein with one or more candidate channel-modulatory materials;
    (c) monitoring a detectable activity of the potassium channel protein; and
    (d) selecting candidate material(s) which modulate said activity relative to a control performed in their absence.

9. An assay according to claim 8, wherein said step (c) of monitoring a detectable activity comprises measuring the electrical current through said potassium channel in the presence of said candidate material.

10. An assay according to claim 9, wherein said step (d) of selecting candidate material(s) comprises selecting a material which results in an electrical current through said potassium channel which is less than is measured in said control.

11. An assay according to claim 8, wherein said step (d) of selecting candidate material(s) comprises selecting a material which induces a change in the concentration of a detectable form of a membrane potential-sensing dye relative to said control.

12. An assay according to claim 8, wherein said nucleic acid has the nucleotide sequence of a nucleic acid obtained from a mouse.

13. An assay according to claim 8, wherein said nucleic acid has the nucleotide sequence of a nucleic acid obtained from a human.

14. An assay according to claim 8, wherein said expression system comprises a cultured host cell.

15. As assay according to claim 14, wherein said host cell is a Xenopus oocyte.

16. An assay according to claim 15, wherein said step (c) of monitoring a detectable activity comprises observing the effect of said candidate material upon the viability of said oocyte in the presence of $K^+$ ions at a concentration of from 1 to 10 mM.

* * * * *

UNITED STATES PATENT AND TRADEMARK OFFICE
CERTIFICATE OF CORRECTION

PATENT NO. : 5,670,335
DATED : September 23, 1997
INVENTOR(S) : Lily Y. Jan, et al It is certified that error appears in the above-identified patent and that said Letters Patent is hereby corrected as shown below:

On the title page, item [54] and Column 1, line 1, the title should read

MAMMALIAN INWARD RECTIFIER POTASSIUM CHANNEL (IRK1) CDNAS, HOST CELLS EXPRESSING THEM, AND SCREENING ASSAYS USING SUCH CELLS

On the title page, item [75], the fourth inventor's name should read

Eitan Reuveny

Signed and Sealed this

Eighth Day of September, 1998

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,670,335

DATED : September 23, 1997

INVENTOR(S) : Lily Y. Jan, et al.

It is certified that error appears in the above-identified patent and that said Letters Patent is hereby corrected as shown below:

In the Claims:

Claim 1, column 53, line 66, "SEQ ID NO: 3", should read --SEQ ID NO: 1--.

Signed and Sealed this

Fifteenth Day of December, 1998

Attest:

BRUCE LEHMAN

Attesting Officer

Commissioner of Patents and Trademarks